US008785139B2

(12) United States Patent
Weber et al.

(10) Patent No.: US 8,785,139 B2

(45) Date of Patent: Jul. 22, 2014

(54) MODIFICATION-DEPENDENT ACTIVITY ASSAYS

(75) Inventors: Alfred Weber, Vienna (AT); Andrea Engelmaier, Vienna (AT); Hans-Peter Schwarz, Vienna (AT)

(73) Assignees: Baxter International Inc., Deerfield, IL (US); Baxter Healthcare SA, Glatipark (CH)

( * ) Notice: Subject to any disclaimer, the term of this patent is extended or adjusted under 35 U.S.C. 154(b) by 250 days.

(21) Appl. No.: 13/475,634

(22) Filed: May 18, 2012

(65) Prior Publication Data

US 2012/0329072 A1 Dec. 27, 2012

Related U.S. Application Data

(60) Provisional application No. 61/487,612, filed on May 18, 2011.

(51) Int. Cl.
*G01N 31/00* (2006.01)
*G01N 33/53* (2006.01)

(52) U.S. Cl.
USPC ........... 435/7.21; 435/7.1; 436/501; 436/518; 424/9.1; 424/130.1; 530/300; 530/350

(58) Field of Classification Search
CPC ... G01R 31/3177; G06F 3/0484; H04L 63/08; C12N 15/8247; C12N 15/8278
See application file for complete search history.

(56) References Cited

FOREIGN PATENT DOCUMENTS

WO 2009/086262 A1 7/2009

OTHER PUBLICATIONS

Koseoglu Mehmet H. et al., "Mechanism of stimulation of glucose transport in response to inhibition of oxidative phosphorylation : Analysis with myc-tagged Glut1." Apr. 1999, Molecular and Cellular Biochemistry, vol. 194, NR. 1-2, pp. 109-116.

Saenko E. L. et al., "Strategies towards a longer acting factor VIII." Haemophilia, Blackwell Science, Oxford, GB, vol. 12, No. Suppl. 3, Jan. 1, 2006, pp. 42-51.

Su Yu-Cheng et al., "Sensitive Quantification of PEGylated Compounds by Second-Generation Anti-Poly (ethylene glycol) Monoclonal Antibodies." Bioconjugate Chemistry, vol. 21, No. 7, Jul. 2010, pp. 1264-1270.

Turecek Peter L. et al., "Peg Modified RVWF Prolongs the Survival of Native RFVIII in Hemophilia A Knock-Out Mice." Blood, American Society of Hematology, US, vol. 108, No. 11, Dec. 9, 2006, p. 299A.

Van Helden Pauline M. et al., "Maintenance and break of immune tolerance against human factor VIII in a new transgenic hemophilic mouse model." Blood, vol. 118, No. 13, Sep. 2011, pp. 3698-3707.

Weber A. et al., "Hamostaseologie : Congress program, 53rd Annual Meeting-Society of Thrombosis and Haemostasis Research, Selective Measurement of Human Recombinant von Willebrand Factor (rVWF)." Haemostaseologie, Stuttgart, DE, Jan. 1, 2009, p. A23.

*Primary Examiner* — Lisa Cook
(74) *Attorney, Agent, or Firm* — K&L Gates LLP

(57) ABSTRACT

Disclosed herein are methods, systems and kits to measure the presence and/or activity of recombinant polypeptides comprising a modification.

28 Claims, 10 Drawing Sheets

MODIFICATION-DEPENDENT ACTIVITY ASSAYS

PRIORITY CLAIM

This patent application claims priority pursuant to 35 U.S.C. §119(e) to U.S. Provisional Patent Application Ser. No. 61/487,612, filed May 18, 2011, which is hereby incorporated by reference in its entirety.

FIELD OF THE DISCLOSURE

Disclosed herein are methods, systems and kits that allow modification-dependent activity assays.

BACKGROUND OF THE DISCLOSURE

A number of diseases or disorders are caused by inadequate levels of a certain polypeptide in the body or by the production of defective versions of this polypeptide. With the advent of genetic-engineering and molecular biology it is now possible to treat such diseases and disorders by replacement polypeptide therapy. For example, administration of a recombinantly-produced polypeptide can treat a disease or disorder by supplementing the low levels of the endogenous polypeptide or substituting for a defective one being produced by the body.

One factor critical to the design an effective recombinant polypeptide therapy is to increase the circulatory half-life of the polypeptide once administered to the body. The length of time a polypeptide remains active in the body can be extended, e.g., by modifying the polypeptides using a wide variety of functional groups that that increase the half-life of the polypeptide. Such modifications protect the polypeptide against proteolytic degradation, increase its stability, enhance or facilitate its interaction with another molecule, reduce its antigenicity, and/or decrease its clearance rate from the body. Exemplary modifications useful for extending the circulatory half-life of an administered recombinant polypeptide include, without limitation PEGylation, polysialylation, HESylation, Sylation, and citrullination.

An important aspect of developing recombinant polypeptide therapy for diseases or disorders is the ability to measure the polypeptide's activity following a modification and/or administration into an individual. This ability is often hampered, however, by the presence of the endogenous polypeptide that interfere with the specificity and accuracy of assays used to detect the presence or activity of the recombinant polypeptide. Thus, there is a need to develop methods for assessing the presence and/or activity of a recombinant polypeptide.

SUMMARY

Described herein are methods, systems and kits, termed modification-dependent activity assays (MDAAs). MDAAs utilize a modification-recognizing capture agent that selectively associates with polypeptides comprising the modification, even in the presence of endogenous polypeptides, non-modified versions of the same or similar polypeptides or polypeptides comprising a different pattern or degree of modification. The presence or activity of the captured polypeptide can then be measured as a way of detecting the presence of polypeptides comprising the modification.

Aspects of the present specification disclose methods for detecting the presence of a recombinant polypeptide comprising a modification. The methods may comprising the steps of incubating a sample including the recombinant polypeptide comprising the modification with a capture agent that selectively binds the modification under conditions allowing the selective binding of the capture agent to the modification, thereby forming a polypeptide-agent complex; purifying the polypeptide-agent complex from the sample; and assaying for the presence of the recombinant polypeptide, wherein detection of the recombinant polypeptide is indicative of the presence of the recombinant polypeptide comprising the modification. Alternatively or concurrently the methods may assay for a polypeptide activity, wherein detection of the polypeptide activity is indicative of the presence of the recombinant polypeptide comprising the modification. A recombinant polypeptide comprising a modification may be a PEGylated, polysialylated, HESylated or Sylated recombinant polypeptide. A capture gent may be an antibody, an aptamer, a synthetic peptide, a binding molecule, and a nucleic acid.

Other aspects of the present specification disclose methods for detecting the presence of a recombinant coagulation factor comprising a modification. The methods may comprising the steps of incubating a sample including the recombinant coagulation factor comprising the modification with a capture agent that selectively binds the modification under conditions allowing the selective binding of the capture agent to the modification, thereby forming a factor-agent complex; purifying the factor-agent complex from the sample; and assaying for the presence of the recombinant coagulation factor, wherein detection of the recombinant coagulation factor is indicative of the presence of the recombinant coagulation factor comprising the modification. Alternatively or concurrently the methods may assay for a coagulation factor activity, wherein detection of the coagulation factor activity is indicative of the presence of the recombinant coagulation factor comprising the modification. A coagulation factor comprising a modification may be a PEGylated recombinant Factor VII, a polysialylated recombinant Factor VII, a HESylated Factor VII, a sylated recombinant Factor VII, a PEGylated recombinant Factor VIII, a polysialylated recombinant Factor VIII, a HESylated Factor VIII, a sylated recombinant Factor VIII, a PEGylated recombinant Factor IX, a polysialylated recombinant Factor IX, a HESylated Factor IX, and/or a sylated recombinant Factor IX.

Other aspects of the present specification disclose kits comprising one or more components useful for practicing the methods disclosed herein and instructions for conducting the methods. A kit may comprising one or more capture agents disclosed herein, one or more solid phase supports, and/or one or more reagents necessary to detect the presence and/or an activity of a recombinant polypeptide comprising a modification disclosed herein.

DETAILED DESCRIPTION

Figure 1:
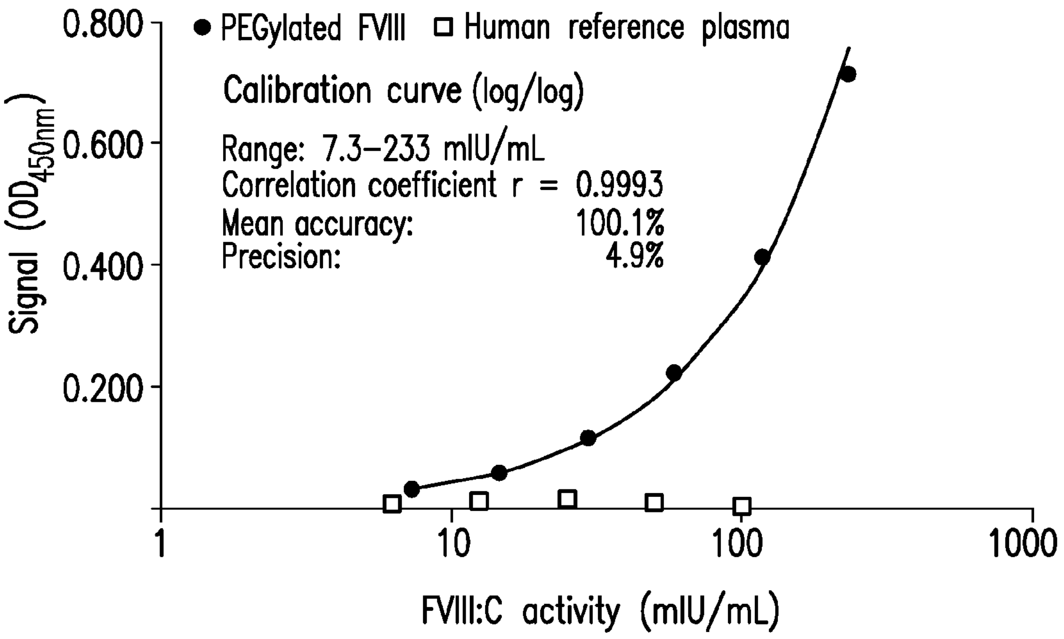
FIG. 1 shows a graph of the concentration-response curves of a MDAA for PEGylated recombinant FVIII obtained using PEGylated FVIII preparation and a human reference plasma preparation.

An important aspect of developing treatment compounds for hemophilia or other disorders is the ability to measure the treatment compound's activity following a modification and/or administration into the natural treatment environment. This ability is often hampered, however, by the presence of similar compounds in the treatment environment that interfere with the specificity and accuracy of activity assay test results.

Described herein are systems and methods, termed modification-dependent activity assays (MDAAs) that allow the separation and detection of recombinant polypeptides in the presence of non-modified versions of the same or similar polypeptides, including, e.g., the naturally-occurring or endogenous polypeptides produced from the genome of the individual being treated. As a non-limiting example, in the development of hemophilia treatments, one may need to measure the activity of a PEGylated recombinant Factor VIII compound following administration. Before the compound is administered to Factor VIII-deficient humans, it is often administered to laboratory animals that may or may not be Factor VIII deficient. Without the MDAAs of the present disclosure, it would not be possible to determine whether the presence or activity measured following administration was due to the administered PEGylated recombinant Factor VIII or to naturally-occurring Factor VIII. The MDAAs disclosed herein allow for such a distinction.

In particular embodiments the MDAAs of the present disclosure comprise a capture agent bound to a solid support. A test sample can be incubated with the solid support where the modified compound is selectively bound by the immobilized capture agent. All other compounds, including, in certain embodiments, endogenous non-modified compounds can be removed by washing. An activity assay on the captured modified compound can be performed.

Steps of the MDAAs disclosed herein can include one or more of: binding an antibody to a solid support; incubating a sample on the surface of the solid support; washing the solid support; and running a chromogenic assay on the solid support. In a particular embodiment, the methods only include the incubating step, the washing step and/or the running the chromogenic assay step. The binding step can include binding an antibody to a plate at a neutral to slightly alkaline pH.

Aspects of the present specification disclose a recombinant polypeptide. A recombinant polypeptide is one synthesized using molecular biology techniques. Any recombinantly-expressed polypeptide comprising a modification may be detected in the methods disclosed herein. The terms "polypeptide," "peptide" and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

Typically, a recombinant polypeptide is expressed from recombinant polynucleotide introduced into cell suitable for culturing. Commonly the recombinant polynucleotide comprises an expression vector that includes an open reading frame encoding the polypeptide to be expressed as well as specialized regulatory coding sequences involved in DNA replication, polypeptide expression, antibiotic resistance, genomic integration, as well as other features. For example, prokaryote expression vectors typically comprise an origin of replication, a suitable promoter and/or enhancer elements, and also sites necessary ribosome binding, polyadenylation, transcriptional termination, as well as 5' flanking non-transcribed sequences and other non-transcribed genetic elements. Exemplary prokaryotic vectors include pET and pRSET using promoters such as, e.g., a bacteriophage T7 promoter.

Eukaryotic expression vectors typically comprise an origin of replication, a suitable promoter and/or enhancer elements, and also sites necessary ribosome binding, polyadenylation, splicing, transcriptional termination, as well as 5' flanking non-transcribed sequences and other non-transcribed genetic elements. Exemplary yeast vectors include pAO, pMET, pPIC, pPICZ, and pYES using promoters such as, e.g., AOX1, AUG1, GAP, and GAL1. Exemplary insect vectors include pAc5, pBAC, pIB, pMIB, pMT using promoters such as, e.g., PH, p10, MT, Ac5, OpIE2, gp64, and polh. Exemplary mammalian vectors include pBPV, pCMV, pCMVTNT, pDNA, pDisplay, pMSG, pOG44, pQBI25, pRc/RSV, pSECTag, pSECTag2, pSG, pSV2cat, pSVK3, pSVL, pUCIG-MET, pVAX1, pWLneo, and pXT1 using promoters such as, e.g., beta-casein, beta-lactoglobulin, whey acid promoter, HSV thymidine kinase, early and late simian virus 40 (SV40), LTRs from retrovirus, and mouse metallothionein-1. Selectable markers include Ampicillin, Chloramphenicol transferase, Kanamycin, Neomycin, and Tetracycline. Suitable expression vectors are known in the art and commercially available.

Insect cells and cell lines derived from insects include cells from, e.g., *Spodoptera frugiperda, Trichoplusia ni, Drosophila melanogaster* and *Manduca sexta*. Non-limiting examples of insect cell lines include High-Five, $K_C$, Schneider's *Drosophila* line 2 (S2), SF9, and SF21 cell lines. Mammalian cells and cell lines derived from mammalian cells include cells from, e.g., mouse, rat, hamster, porcine, bovine, equine, primate and human. Non-limiting examples of mammalian cell lines include 1A3, 3T3, 6E6, 10T1/2, APRT, BALB/3T3, BE (2)-C, BHK, BT, C6, C127, CHO, CHP3, COS-1, COS-7, CPAE, ESK-4, FB2, GH1, GH3, HeLa, HEK-293, HepG2, HL-60, IMR-32, L2, LLC-PK1, L-M, MCF-7, NB4, NBL-6, NCTC, Neuro 2A, NIE-115, NG108-15, NIH3T3, PC12, PK15, SBAC, SH-SY5Y, SK-Hep, SK-N-DZ, SK-N-F1, SK-N-SH, ST, SW-13, and W-1 cell lines. Cell lines may be obtained from the American Type Culture Collection, European Collection of Cell Cultures and/or the German Collection of Microorganisms and Cell Cultures.

Various prokaryote and/or eukaryotic expression systems may be employed to recombinantly express a protein disclosed herein. Expression systems can include any of a variety of characteristics including, without limitation, inducible expression, non-inducible expression, constitutive expression, tissue-specific expression, cell-specific expression, viral-mediated expression, stably-integrated expression, and transient expression. How to make and use such expression systems are known in the art.

A recombinant polypeptide disclosed herein is typically a therapeutic polypeptide. Non-limiting examples of a thereapeutic polypeptide include Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF), ADAMTS 13 protease, IL-1 alpha, IL-1 beta, IL-3, IL-4, IL-5, IL-6, IL-11, colony stimulating factor-1 (CSF-1), M-CSF, SCF, GM-CSF, granulocyte colony stimulating factor (G-CSF), EPO, interferon-α (IFN-α), consensus interferon, IFN-β, IFN-γ, IFN-ω, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, β-endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, TNF0, TNF1, TNF2, transforming growth factor .alpha., transforming growth factor β, transforming growth factor β1, transforming growth factor β1.2, transforming growth factor β2, transforming growth factor in, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, α-galactosidase, β-galactosidase, DNAse, fetuin, leutinizing hormone, estrogen, insulin, albumin, lipoproteins, fetoprotein, transferrin, thrombopoietin, urokinase, integrin, thrombin, leptin, Humira (adalimumab), Prolia (denosumab), Enbrel (etanercept), or a biologically active fragment, derivative or variant thereof. Other therapeutic polypeptides are described in Table 1 of Siekmann, et al., Nucleophilic Catalysts for Oxime Linkage, US 2012/0035344, which I hereby incorporated by reference in its entirety.

A recombinant polypeptide disclosed herein include, without limitation, a growth factor, a cytokine, an immunomodulating agent, a hormone, an antibody, an enzyme, an enzyme inhibitor, a protease, a protease inhibitor, an esterase, a transferase, an oxidoreductase, a hydrolase, an asparaginase, an adenosine deaminase, a neurotoxin, a liver protein, a pancreatic protein, a muscle protein, a brain protein, a lung protein, and a blood protein.

In aspects of this embodiment, an esterase may include, without limitation, a butyrylcholinesterase or a acetylcholinesterase.

In aspects of this embodiment, a cytokine may include, without limitation a chemokine, a lymphokine, a tumor necrosis factor, a hematopoietic factor like a granulocyte colony-stimulating factor and a granulocyte macrophage colony-stimulating factor.

In aspects of this embodiment, an immunomodulating agent may include, without limitation, an interleukin and an interferon.

In aspects of this embodiment, a blood protein may be a erythropoiesis-stimulating agent, including, without limitation, an erythropoietin, an erythropoietin, an erthropoyetin, and a darbepoetin.

In aspects of this embodiment, a blood protein may include, without limitation, ADAMTS-13, α1-antiplasmin, α2-antiplasmin, antithrombin, antithrombin III, cancer procoagulant, erythropoietin, Factor II, Factor IIa, Factor V, Factor Va, Factor VI, Factor VIa, Factor VII, Factor VIIa, Factor VIII, Factor VIIIa, Factor IX, Factor IXa, Factor X, Factor Xa, Factor XI, Factor XIa, Factor XII, Factor XIIa, Factor XIII, Factor XIIIa, fibronectin, fibrinogen (Factor I), heparin cofactor II, high-molecular-weight kininogen (HMWK), intramuscular immunoglobulin, intravenous immunoglobulin, plasmin, plasminogen, plasminogen activator inhibitor-1 (PAI1), plasminogen activator inhibitor-2 (PAI2), prekallikrein, prostacyclin, protein C, active protein C (APC), protein S, protein Z, protein Z-related protease inhibitor, thrombomodulin, tissue factor (Factor III), Tissue factor pathway inhibitor (TFPI), tissue plasminogen activator (t-PA), urokinase, and Von Willebrand Factor.

In aspects of this embodiment, a blood protein may be a blood coagulation protein, including both its inactive and active forms. A blood coagulation factor refers to the factors of the blood coagulation pathway comprising components in the intrinsic, extrinsic and common coagulation pathways. The term embraces such factors whether they are present in a sample as endogenous components (i.e., being inherent in the blood sample), or whether they have been added as exogenous factors. Phospholipid(s) may also be included as coagulation factors when added in a method utilizing any of the intrinsic, extrinsic or common pathways for activation of coagulation. In aspects of this embodiment, a blood protein may be a blood coagulation factor, including, without limitation, Factor II, Factor VII, Factor VIII, Factor IX and Factor X.

In aspects of this embodiment, a blood protein may be a protease inhibitor, including, without limitation, α1-antitrypsin, α1-antichymotrypsin, C1-inhibitor, and α2-antiplasmin, antithrombin.

In aspects of this embodiment, a blood protein may be a protease, including, without limitation, trypsin, chymotrypsin, elastase, pepsin, and ADAMTS13.

Aspects of the present specification disclose a modification. A modification disclosed herein is one associated with a recombinant polypeptide disclosed herein. Any modification having a binding site or moiety for which a capture agent can selectively bind may be used in the methods disclosed herein. As such, any modification for which there exists a naturally occurring capture agent or for which a capture agent can be prepared would be useful in the methods disclosed herein. A modification disclosed herein includes one that occurs during or after the expression of the recombinant polypeptide disclosed herein.

In one embodiment, a modification may be a post-translational modification. A posttranslational modification is a chemical modification of a polypeptide, typically by attaching a biochemical functional group to an amino acid of the polypeptide. A recombinant polypeptide disclosed herein may be modified by linking the polypeptide to any of these biochemical functional group depending on, as is understood by one of ordinary skill, the particular modification of the polypeptide to be captured.

Examples of a modification include, without limitation, an acetate group, a phosphate group, a lipid group, or a carbohydrate group, a myristate group, a palmitate group, an isoprenoid group like a farnesol group and geranylgeraniol group, a glycosylphosphatidylinositol (GPI) group, a lipoate group, a flavin group, a heme C group, a 4'-phosphopantetheinyl group, a retinylidene group, a diphthamide group, an ethanolamine phosphoglycerol group, a hypusine group, an acetyl group, a formyl group, an alkyl group, a methyl group, an amide group, an amino acid, a butyl group, a carboxyl group, a glycosyl group, a polysialic acid (PSA) group, a hydroxyl group, a malonyl group, an iodine group, a phosphate group, an adenylyl group, a succinyl group, a sulfate group, a selenium group, a carbohydrate group, a starch group, a hydroxyl-ethyl starch (HES) group, a polysaccharide group, a sugar group, a polyethylene glycol (PEG) group, an ubiquitin group, a pullulane group, a chitosan group, a hyaluronic acid group, a chondroitin sulfate group, a dermatan sulfate group, a dextran group, a carboxymethyl-dextran group, a polyalkylene oxide (PAO) group, a polyalkylene glycol (PAG) group, a polypropylene glycol (PPG) group, a polyoxazoline group, a polyacryloylmorpholine group, a polyvinyl alcohol (PVA) group, a polycarboxylate group, a polyvinylpyrrolidone (PVP) group, a polyphosphazene group, a polyoxazoline group, a polyethylene-co-maleic acid anhydride group, a polystyrene-co-maleic acid anhydride group, a poly(1-hydroxymethylethylene hydroxymethylformal) (PHF) group, and a 2-methacryloyloxy-2'-ethyltrimethylammonium-phosphate (MPC) group.

Processes known to attach a biochemical functional group to an amino acid of the polypeptide include, without limitation, myristoylation, palmitoylation, isoprenylation (prenylation), glypiation, lipoylation, flavinylation, phosphopantetheinylation, retinylidenylation, diphthamidylation, ethanolamine phosphoglycerylation, hypusinylation, acylation, acetylation, formylation, alkylation, amidation, arginylation, polyglutamylation, polyglycylation, butyrylation, gamma-carboxylation, glycosylation, polysialylation, malonylation, hydroxylation, iodination, nucleosylation, oxidation, phosphoroesterfication, phosphoramidation, phosphorylation, adenylylation, propionylation, pyroglutamate, S-glutathionylation, S-nitrosylation, succinylation, sulfation, selenoylation, glycation, biotinylation, acylation, PEGylation, HESylation, Sylation (Starchylation), citrullination, deamidation, eliminylation, carbamylation, deimination, pupylation, neddylation, ubiquitination, SUMOylation, and ISGylation.

Aspects of the present disclosure comprise, in part, a sample comprising a recombinant polypeptide disclosed herein. A sample may be any material to be tested for the presence or activity of a recombinant polypeptide disclosed herein. A variety of samples can be assayed according to a method disclosed herein including, without limitation, purified, partially purified, or unpurified a recombinant polypeptide disclosed herein; a formulated a recombinant polypeptide product; crude, fractionated or partially purified, or purified cell lysates from, e.g., bacteria, yeast, insect, or mammalian sources; and cell, tissue, or organ samples. A sample can be from any subject individual, including but not limited to, insects or mammals such as, e.g., human, bird, porcine, equine, bovine, murine, cat, rat, dog, or sheep.

In one aspect of this embodiment, a sample may be a biological sample that contains or potentially contains a recombinant polypeptide disclosed herein. A biological sample can include any cell, tissue, or organ sample taken directly from an individual. A biological sample can also be a sample of any body fluid taken directly from an individual including, without limitation, blood, urine, sputum, semen, feces, saliva, bile, cerebral fluid, nasal swab, urogenital swab, nasal aspirate, spinal fluid, etc. A biological sample can also include any preparation derived from a sample taken directly from an individual including, without limitation, a plasma fraction of a blood sample, a serum fraction of a blood sample, or an eluate from a purification process. A blood sample refers to any sample taken or derived from blood, such as a whole blood sample, a blood plasma sample or a blood serum sample.

A sample may be treated in a way to improve the detectability of a recombinant polypeptide disclosed herein or its activity within the sample. Such treatments may, e.g., reduce the viscosity of the sample or purify a component fraction of the sample. Methods of treatment can involve lysing, dilution, purification, extraction, filtration, distillation, separation, concentration, inactivation of interfering components, and the addition of reagents. In addition, a solid material suspected of containing a recombinant polypeptide disclosed herein may be used as a test sample once it is modified to form a liquid medium or to release the recombinant polypeptide. The selection and pretreatment of biological samples prior to testing is well known in the art and need not be described further.

In treatments involving extraction, an extraction buffer can comprise, in particular embodiments, from about 0.75 to about 1.125M of salt in a buffered solution although this is a non-limiting range and other molarities both below 0.75M and/or above 1.25M can also be used. In one embodiment, a salt in buffered solution is about 0.75M, 1M, 1.1M or 1.125M. In further embodiments, a zwitterionic agent (e.g., Zwittergent 3/12) is provided to enhance extraction of one or more modified compounds. For example, a zwitterion agent is provided in an extraction buffer at about 0.1% to about 1.5%. In yet further embodiments, a Zwittergent agent is at a concentration of about 0.1%, 0.15%, 0.175%, 0.2%, 0.225%, 0.25%, 0.275%, 0.3%, 0.325%, 0.350%, 0.375%, 0.4%, 0.425%, 0.450%, 0.475%, 0.5%, 0.525%, 0.550%, 0.575%, 0.6%, 0.7%, 0.75%, 1.0%, 1.1%, 1.2%, 1.3%, 1.4%, 1.5%, 1.6%, 1.7%, 1.8%, 1.9% or 2.0%. Examples of zwitterionic agent include Zwittergent 3/12; most amino acids at physiological pH used as buffering agents in Good's buffers: the amino-sulfonic acid based MES, MOPS, HEPES, PIPES or CHAPS (3-[(3-cholamidopropyl)dimethylammonio]-1-propanesulfonate); the amino-carboxylic acid (amino acid) based glycine, its derivatives bicine and tricine, and alanine; CHAPSO (3-[(3-cholamidopropyl)dimethylammonio]-2-hydroxy-1-propanesulfonate); CAPSO (3-cyclohexylamino)-2-Hydroxy-1-Propanesulfonic Acid); natural products like the alkaloids psilocybin and lysergic acid; betaines; Quinonoid zwitterions; drugs such as Fexofenadine (Allegra) and Cephaloridine; 2-(N Morpholino)ethanesulfonic acid, (3-[N-Morpholino])propanesulfonic acid, 2-[(2-Amino-2-oxoethyl)amino]-ethanesulfonic acid, piperazine-N,N'-bis (2-ethanesulfonic acid), 3-(N-Morpholino)-2-hydroxypropanesulfonic acid, N,N-Bis(2-hydroxyethyl)-2-aminoethanesulfonic acid, 3-(N-Morpholino) propanesulfonic acid, N-(2-Hydroxyethyl) piperazine-N'-(2-ethanesulfonic acid), N-Tris(hydroxymethyl)methyl-2 aminoethanesulfonic acid, 3-[N,N-Bis(2-hydroxyethyl) amino]-2-hydroxypropanesulfonic acid, 3-[N-Tris(hydroxymethyl)-methylamino)-2-hydroxypropanesulfonic acid, N-(2-hydroxyethyl)piperazine-N'-(2-hydroxypropanesulfonic acid), piperazine-N,N'-bis(2-hydroxypropanesulfonic acid), N-(2-Hydroxyethyl)piperazine-N'-(3-propanesulfonic acid), N-Tris(hydroxymethyl)methyl-3-aminopropanesulfonic acid, 3-[(1,1-Dimethyl-2-hydroxyethyl)amino]-2-hydroxypropanesulfonic, acid, 2-(N-Cyclohexylamino)ethanesulfonic acid, 3-(cyclohexylamino)-2-hydroxy-1-propanesulfonic acid, 2-Amino-2-methyl-1-propanol, 3-(cyclohexylamino)-1-propanesulfonic acid, or mixtures thereof. Chosen zwitterionic agents and/or detergents should not include the particular entity (i.e. PEG, HES, etc.) used to modify the compound measured in a particular assay.

Aspects of the present specification disclose a capture agent. A capture agent or modification-recognizing capture agent refers to any molecule capable of selective or substantially selective (that is with limited cross-reactivity) binding to a moiety present on a modification disclosed herein or otherwise associating with a modification disclosed herein. As used herein, the term “selectively” refers to having a unique effect or influence or reacting in only one way or with only one thing. As used herein, the term “selectively binds,” when made in reference to an capture agent, refers to the discriminatory binding of the capture agent to the indicated target epitope such that the antibody does not substantially cross react with non-target epitopes. Any capture agent that can selectively bind to a modification present on a recombinant polypeptide disclosed herein may be used in the methods disclosed herein. A capture agent generally has a single specificity although capture agents having multiple specificities for two or more recombinant polypeptides disclosed herein may be used. Non-limiting examples of a capture agent include an antibody, an aptamer, a synthetic peptide, a binding molecule, and a nucleic acid.

Selective binding of a capture agent includes binding properties such as, e.g., binding affinity, binding specificity, and binding avidity. Binding affinity refers to the length of time a capture agent resides at its binding site or moiety, and can be viewed as the strength with which a capture agent binds its binding site or moiety. Binding affinity can be described a capture agent's equilibrium dissociation constant (KD), which is defined as the ratio Kd/Ka at equilibrium. Where Ka is a capture agent's association rate constant and kd is a capture agent's dissociation rate constant. Binding affinity is determined by both the association and the dissociation and alone neither high association or low dissociation can ensure high affinity. The association rate constant (Ka), or on-rate constant (Kon), measures the number of binding events per unit time, or the propensity of a capture agent's and its binding site or moiety to associate reversibly into its agent-moiety complex. The association rate constant is expressed in $M^{-1} s^{-1}$, and is symbolized as follows: [CA]×[BS]×Kon. The larger the association rate constant, the more rapidly a capture agent binds to its binding site or moiety, or the higher the binding affinity between a capture agent and its binding site or moiety. The dissociation rate constant (Kd), or off-rate constant (Koff), measures the number of dissociation events per unit time propensity of agent-moiety complex to separate (dissociate) reversibly into its component molecules, namely the capture agent and its binding site or moiety. The dissociation rate constant is expressed in $s^{-1}$, and is symbolized as follows: [CA+BS]×Koff. The smaller the dissociation rate constant, the more tightly bound a capture agent is to its binding site or moiety, or the higher the binding affinity between capture agent and its binding site or moiety. The equilibrium dissociation constant (KD) measures the rate at which new agent-moiety complexes formed equals the rate at which agent-moiety complexes dissociate at equilibrium. The equilibrium dissociation constant is expressed in M, and is defined as Koff/Kon=[CA]×[BS]/[CA+BS], where [CA] is the molar concentration of a capture agent, [BS] is the molar concentration of the binding site or moiety, and [CA+BS] is the of molar concentration of the agent-moiety complex, where all concentrations are of such components when the system is at equilibrium. The smaller the equilibrium dissociation constant, the more tightly bound a capture agent is to its binding site or moiety, or the higher the binding affinity between a capture agent and its binding site or moiety.

In an embodiment, the binding affinity of a capture agent disclosed herein may have an association rate constant of, e.g., less than $1\times10^{5}$ $M^{-1}$ $s^{-1}$, less than $1\times10^{6}$ $M^{-1}$ $s^{-1}$, less than $1\times10^{7}$ $M^{-1}$ $s^{-1}$, or less than $1\times10^{8}$ $M^{-1}$ $s^{-1}$. In another embodiment, the binding affinity of a capture agent disclosed herein may have an association rate constant of, e.g., more than $1\times10^{5}$ $M^{-1}$ $s^{-1}$, more than $1\times10^{6}$ $M^{-1}$ $s^{-1}$, more than $1\times10^{7}$ $M^{-1}$ $s^{-1}$, or more than $1\times10^{8}$ $M^{-1}$ $s^{-1}$. In other aspects, the binding affinity of a capture agent disclosed herein may have an association rate constant between $1\times10^{5}$ $M^{-1}$ $s^{-1}$ to $1\times10^{8}$ $M^{-1}$ $s^{-1}$, $1\times10^{6}$ $M^{-1}$ $s^{-1}$ to $1\times10^{8}$ $M^{-1}$ $s^{-1}$, $1\times10^{5}$ $M^{-1}$ $s^{-1}$ to $1\times10^{7}$ $M^{-1}$ $s^{-1}$, or $1\times10^{6}$ $M^{-1}$ $s^{-1}$ to $1\times10^{7}$ $M^{-1}$ $s^{-1}$.

In another embodiment, the binding affinity of a capture agent disclosed herein may have a disassociation rate constant of less than $1\times10^{-3}$ $s^{-1}$, less than $1\times10^{-4}$ $s^{-1}$, or less than $1\times10^{-5}$ $s^{-1}$. In other aspects of this embodiment, the binding affinity of a capture agent disclosed herein may have a disassociation rate constant of, e.g., less than $1.0\times10^{-4}$ $s^{-1}$, less than $2.0\times10^{-4}$ $s^{-1}$, less than $3.0\times10^{4}$ $s^{-1}$, less than $4.0\times10^{-4}$ $s^{-1}$, less than $5.0\times10^{-4}$ $s^{-1}$, less than $6.0\times10^{-4}$ $s^{-1}$, less than $7.0\times10^{-4}$ $s^{-1}$, less than $8.0\times10^{-4}$ $s^{-1}$, or less than $9.0\times10^{-4}$ $s^{-1}$. In another embodiment, the binding affinity of a capture agent disclosed herein may have a disassociation rate constant of, e.g., more than $1\times10^{-3}$ $s^{-1}$, more than $1\times10^{-4}$ $s^{-1}$, or more than $1\times10^{-5}$ $s^{-1}$. In other aspects of this embodiment, the binding affinity of a capture agent disclosed herein may have a disassociation rate constant of, e.g., more than $1.0\times10^{-4}$ $s^{-1}$, more than $2.0\times10^{-4}$ $s^{-1}$, more than $3.0\times10^{-4}$ $s^{-1}$, more than $4.0\times10^{-4}$ $s^{-1}$, more than $5.0\times10^{-4}$ $s^{-1}$, more than $6.0\times10^{-4}$ $s^{-1}$, more than $7.0\times10^{-4}$ $s^{-1}$, more than $8.0\times10^{-4}$ $s^{-1}$, or more than $9.0\times10^{-4}$ $s^{-1}$.

In another embodiment, the binding affinity of a capture agent disclosed herein may have an equilibrium disassociation constant of less than 0.500 nM. In aspects of this embodiment, the binding affinity of a capture agent disclosed herein may have an equilibrium disassociation constant of, e.g., less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM. In another embodiment, the binding affinity of a capture agent disclosed herein may have an equilibrium disassociation constant of more than 0.500 nM. In aspects of this embodiment, the binding affinity of a capture agent disclosed herein may have an equilibrium disassociation constant of, e.g., more than 0.500 nM, more than 0.450 nM, more than 0.400 nM, more than 0.350 nM, more than 0.300 nM, more than 0.250 nM, more than 0.200 nM, more than 0.150 nM, more than 0.100 nM, or more than 0.050 nM.

In yet another embodiment, the binding affinity of a capture agent disclosed herein may have an association rate constant for a polypeptide without a modification or a polypeptide with a different pattern or degree of modification of, e.g., less than $1\times10^{0}$ $M^{-1}$ $s^{-1}$, less than $1\times10^{1}$ $M^{-1}$ $s^{-1}$, less than $1\times10^{2}$ $M^{-1}$ $s^{-1}$, less than $1\times10^{3}$ $M^{-1}$ $s^{-1}$, or less than $1\times10^{4}$ $M^{-1}$ $s^{-1}$. In another embodiment, the binding affinity of a capture agent disclosed herein may have an association rate constant for a polypeptide without a modification or a polypeptide with a different pattern or degree of modification of, e.g., at most $1\times10^{0}$ $M^{-1}$ $s^{-1}$, at most $1\times10^{1}$ $M^{-1}$ $s^{-1}$, at most $1\times10^{2}$ $M^{-1}$ $s^{-1}$, at most $1\times10^{3}$ $M^{-1}$ $s^{-1}$, or at most $1\times10^{4}$ $M^{-1}$ $s^{-1}$.

Binding specificity is the ability of a capture agent to discriminate between a molecule containing its binding site or moiety and a molecule that does not contain that binding site or moiety. One way to measure binding specificity is to compare the Kon association rate of a capture agent for a molecule containing its binding site or moiety relative to the Kon association rate of a capture agent for a molecule that does not contain that binding site or moiety. For example, comparing the association rate constant (Ka) of a capture agent for a recombinant polypeptide comprising a modification relative to a recombinant polypeptide without such a modification. In aspects of this embodiment, a capture agent that selectively binds to a recombinant polypeptide comprising a modification has an association rate constant (Ka) for a recombinant polypeptide without such a modification of, e.g., less than $1\times10^{0}$ $M^{-1}$ $s^{-1}$, less than $1\times10^{1}$ $M^{-1}$ $s^{-1}$, less than $1\times10^{2}$ $M^{-1}$ $s^{-1}$, less than $1\times10^{3}$ $M^{-1}$ $s^{-1}$ or less than $1\times10^{4}$ $M^{-1}$ $s^{-1}$ then the association rate constant (Ka) for a recombinant polypeptide without such a modification or a recombinant polypeptide with a different pattern or degree of modification. In other aspects of this embodiment, a capture agent that selectively binds to a recombinant polypeptide comprising a modification has an association rate constant (Ka) for a recombinant polypeptide without such a modification of, e.g., at most $1\times10^{0}$ $M^{-1}$ $s^{-1}$, at most $1\times10^{1}$ $M^{-1}$ $s^{-1}$, at most $1\times10^{2}$ $M^{-1}$ $s^{-1}$, at most $1\times10^{3}$ $M^{-1}$ $s^{-1}$ or at most $1\times10^{4}$ $M^{-1}$ $s^{-1}$. In yet other aspects of this embodiment, a capture agent that selectively binds to a recombinant polypeptide comprising a modification has an association rate constant (Ka) for the recombinant polypeptide comprising a modification that is more than $1\times10$ $M^{-1}$ $s^{-1}$, more than $1\times10^{1}$ $M^{-1}$ $s^{-1}$, more than $1\times10^{2}$ $M^{-1}$ $s^{-1}$, more than $1\times10^{3}$ $M^{-1}$ $s^{-1}$ or more than $1\times10^{4}$ $M^{-1}$ $s^{-1}$ relative to the association rate constant (Ka) of the capture agent for a recombinant polypeptide without such a modification and/or the association rate constant (Ka) of the capture agent for a recombinant polypeptide with a different pattern or degree of modification.

In yet aspects of this embodiment, a capture agent that selectively binds to a recombinant polypeptide comprising a modification has an association rate constant (Ka) for a recombinant polypeptide without such a modification of, e.g., at least 2-fold more, at least 3-fold more, at least 4-fold more, at least 5-fold more, at least 6-fold more, at least 7-fold more, at least 8-fold more, or at least 9-fold more. In further aspects of this embodiment, a capture agent that selectively binds to a recombinant polypeptide comprising a modification has an association rate constant (Ka) for a recombinant polypeptide without such a modification of, e.g., at least 10-fold more, at least 100-fold more, at least 1,000-fold more or at least 10,000-fold more. In yet other aspects of this embodiment, a capture agent that selectively binds to a recombinant polypeptide comprising a modification has an association rate constant (Ka) for a recombinant polypeptide without such a modification of, e.g., at most 1-fold more, at most 2-fold more, at most 3-fold more, at most 4-fold more, at most 5-fold more, at most 6-fold more, at most 7-fold more, at most 8-fold more, or at most 9-fold more. In yet other aspects of this embodiment, a capture agent that selectively binds to a recombinant polypeptide comprising a modification has an association rate constant (Ka) for a recombinant polypeptide without such a modification of, e.g., at most 10-fold more, at most 100-fold more, at most 1.000-fold more or at most 10.000-fold more.

The binding specificity of a capture agent can also be characterized as a binding specificity ratio of a recombinant polypeptide comprising a modification relative to a recombinant polypeptide without such a modification. In aspects of this embodiment, a capture agent has a binding specificity ratio for a recombinant polypeptide comprising a modification relative to a recombinant polypeptide without such a modification of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1. In yet other aspects of this embodiment, a capture agent has a binding specificity ratio for a recombinant polypeptide comprising a modification relative to a recombinant polypeptide without such a modification of, e.g., at least 2:1, at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, or at least 40:1. In still other aspects of this embodiment, a capture agent has a binding specificity ratio for a recombinant polypeptide comprising a modification relative to a recombinant polypeptide without such a modification of, e.g., at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1.

Binding avidity, also known as functional affinity, refers to the sum total of the functional binding strength between a multivalent capture agent and its binding site or moiety. A capture agent can have more than one binding site and many modifications contain more than one binding site or moiety. While binding avidity of a capture agent depends on the binding affinities of the individual capture agent binding sites, binding avidity is greater than the binding affinity as all the agent-moiety interactions must be broken simultaneously for a capture agent to dissociate completely. It is envisioned that a capture agent can selectively bind to any and all binding sites or moieties for that capture agent.

Typically, the capture agent can distinguish a recombinant polypeptide comprising a modification disclosed herein from the same polypeptide but without the modification or with a different pattern or degree of the same modification. A non-modified polypeptide, as well as, a polypeptide but without a modification, refers to a polypeptide not containing the modification present in a recombinant polypeptide disclosed herein. A non-modified polypeptide may be present in a sample but will not selectively bind to a capture agent disclosed herein as the polypeptide lacks the modification that is required for capturing. One non-limiting example of a non-modified polypeptide is a naturally-occurring or endogenous polypeptide expressed from the genome of the individual from which a sample was directly taken or derived from. Another non-limiting example of a non-modified polypeptide is a recombinant polypeptide expressed from a prokaryotic expression system.

A polypeptide comprising a different pattern or degree of modification refers to a polypeptide having the modification present in a recombinant polypeptide disclosed herein, but in a pattern or degree that allows the methods disclosed herein to distinguish the two types of polypeptides. For example, a polypeptide having a different pattern or degree of modification may be present in a sample but will not selectively bind to a capture agent disclosed herein as the polypeptide lacks the pattern or degree of modification that is required for capturing. One non-limiting example of a polypeptide having a different pattern or degree of modification is a naturally-occurring or endogenous polypeptide expressed from the genome of the individual from which a sample was directly taken or derived from. Another non-limiting example of a polypeptide having a different pattern or degree of modification is a recombinant polypeptide expressed from a prokaryotic expression system. Yet another non-limiting example of a polypeptide having a different pattern or degree of modification is a recombinant polypeptide expressed from cells of a cell culture line different from the cells of a cell culture line used to express a recombinant polypeptide disclosed herein. Still another non-limiting example of a polypeptide having a different pattern or degree of modification is a recombinant polypeptide expressed using a manufacturing process different from the manufacturing process used to express a recombinant polypeptide disclosed herein.

In an embodiment, a capture agent is an antibody. An antibody refers to a molecule generated by an immune system that was made in response to a particular antigen that specifically binds to that antigen, and includes both naturally occurring antibodies and non-naturally occurring antibodies. An antibody can be a polyclonal antibody, a monoclonal antibody, a dimer, a multimer, a monospecific antibody, a bispecific antibody, such as, e.g., disulfide stabilized Fv fragments, scFv tandems [(scFv)2 fragments], a multispecific antibody, a multivalent antibody, a humanized antibody, a camelized antibody, a chimeric antibody, bi-functional antibody, a cell-associated antibody like an Ig receptor, a linear antibody, a diabody, a tribody, a tetrabody, a minibody, or derivative or analog thereof, so long as the fragment exhibits the desired biological activity, and single chain derivatives of the same. An antibody can be a full-length immunoglobulin molecule comprising the $V_H$ and $V_L$ domains, as well as a light chain constant domain ($C_L$) and heavy chain constant domains, $C_{H1}$, $C_{H2}$ and $C_{H3}$, or an immunologically active fragment of a full-length immunoglobulin molecule, such as, e.g., a Fab fragment, a $F(ab')_2$ fragment, a Fc fragment, a Fd fragment, a Fv fragment, a single chain Fv (scFv). An antibody can be derived from any vertebrate species (e.g., human, goat, horse, donkey, murine, rat, rabbit, or chicken), and can be of any type (e.g., IgG, IgE, IgM, IgD, and IgA), class (e.g., IgA, IgD, IgE, IgG, and IgM) or subclass (IgG1, IgG2, IgG3, IgG4, IgA1 and IgA2).

Antibodies useful to practice the methods disclosed herein are commercially available or can be generated according to methods that are well-known in the art. For example, monoclonal antibodies can be generated by the hybridoma method. Antibody fragments can be generated via proteolytic digestion of intact antibodies or can be produced directly by recombinant host cells. For example, Fab' fragments can be directly recovered from *E. coli* and chemically coupled to form F(ab')2 fragments. In another embodiment, F(ab')2 can be formed using the leucine zipper GCN4 to promote assembly of the F(ab')2 molecule. According to another approach, Fv, Fab or F(ab')2 fragments can be isolated directly from recombinant host cell culture. Other techniques for the production of antibody fragments are apparent to a person with ordinary skill in the art.

Examples of an antibody suitable for the methods disclosed herein include, without limitation, an anti-acetate antibody, an anti-phosphate antibody, an anti-lipid antibody, or an anti-carbohydrate antibody, an anti-myristate antibody, an anti-palmitate antibody, an anti-isoprenoid antibody like an anti-farnesol antibody and geranylgeraniol antibody, an anti-glycosylphosphatidylinositol (GPI) antibody, an anti-lipoate antibody, an anti-flavin antibody, an anti-heme C antibody, an anti-4'-phosphopantetheinyl antibody, an anti-retinylidene antibody, an anti-diphthamide antibody, an anti-ethanolamine phosphoglycerol antibody, an anti-hypusine antibody, an anti-acetyl antibody, an anti-formyl antibody, an anti-alkyl antibody, an anti-methyl antibody, an anti-amide antibody, an anti-amino acid antibody, an anti-butyl antibody, an anti-carboxyl antibody, an anti-glycosyl antibody, an anti-polysialic acid antibody, an anti-hydroxyl antibody, an anti-malonyl antibody, an anti-iodine antibody, an anti-phosphate antibody, an anti-adenylyl antibody, an anti-succinyl antibody, an anti-sulfate antibody, an anti-selenium antibody, an anti-carbohydrate antibody, an anti-polysaccharide antibody, an anti-starch (anti-S) antibody, an anti-hydroxyl-ethyl starch (HES) antibody, an anti-sugar antibody, an anti-polyethelene glycol (PEG) antibody, an anti-ubiquitin antibody, an anti-pullulane antibody, an anti-chitosan antibody, an anti-hyaluronic acid antibody, an anti-chondroitin sulfate antibody, an anti-dermatan sulfate antibody, an anti-dextran antibody, an anti-carboxymethyl-dextran antibody, an anti-polyalkylene oxide (PAO) antibody, an anti-polyalkylene glycol (PAG) antibody, an anti-polypropylene glycol (PPG) antibody, an anti-polyoxazoline antibody, an anti-polyacryloylmorpholine antibody, an anti-polyvinyl alcohol (PVA) antibody, an anti-polycarboxylate antibody, an anti-polyvinylpyrrolidone (PVP) antibody, an anti-polyphosphazene antibody, an anti-polyoxazoline antibody, an anti-polyethylene-co-maleic acid anhydride antibody, an anti-polystyrene-co-maleic acid anhydride antibody, an anti-poly(1-hydroxymethylethylene hydroxymethylformal) (PHF) antibody, and an anti-2-methacryloyloxy-2'-ethyltrimethylammonium-phosphate (MPC) antibody.

A capture agent disclosed herein may be attached to a solid phase as a support for the capture agent. As used herein, the term "solid-phase support" is synonymous with "solid phase" and refers to any matrix that can be used for immobilizing capture agent disclosed herein. A solid phase may be constructed using any suitable material with sufficient surface affinity to bind a capture agent. The solid phase support selected can have a physical property that renders it readily separable from soluble or unbound material and generally allows unbound materials, such as, e.g., excess reagents, reaction by-products, or solvents, to be separated or otherwise removed (by, e.g., washing, filtration, centrifugation, etc.) from solid phase support-bound assay component. Non-limiting examples of how to make and use a solid phase supports are described in, e.g., Molecular Cloning, A Laboratory Manual, supra, (2001); and Current Protocols in Molecular Biology, supra, (2004), each of which is hereby incorporated by reference in its entirety.

Useful solid supports include: natural polymeric carbohydrates and their synthetically modified, crosslinked, or substituted derivatives, such as agar, agarose, cross-linked alginic acid, substituted and cross-linked guar gums, dextran, diazocellulose, carbohydrates, starch, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials can be used as filters with the above polymeric materials); and mixtures or copolymers of the above classes, such as graft copolymers obtained by initializing polymerization of synthetic polymers on a pre-existing natural polymer. Nitrocellulose and nylon can also be used. All of these materials can be used in suitable shapes, such as films, sheets, tubes, column; pins or "dipsticks"; a magnetic particle, particulates, microparticles, beads, or plates, or they can be coated onto, bonded, or laminated to appropriate inert carriers, such as paper, glass, plastic films, fabrics, or the like.

Alternatively, a solid phase can constitute microparticles. Appropriate microparticles include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field. Microparticles can be suspended in the mixture of soluble reagents and biological sample or can be retained and immobilized by a support material. In the latter case, the microparticles on or in the support material are not capable of substantial movement to positions elsewhere within the support material. Alternatively, the microparticles can be separated from suspension in the mixture of soluble reagents and biological sample by sedimentation or centrifugation. When the microparticles are magnetic or paramagnetic the microparticles can be separated from suspension in the mixture of soluble reagents and biological sample by a magnetic field.

A capture agent may be attached to the solid phase by adsorption, where it is retained by hydrophobic forces. Alternatively, the surface of a solid phase may be activated by chemical processes that cause covalent linkage of the capture agent to the support. A capture agent may be attached to the solid phase by ionic capture, where it is retained by a charged polymer.

After the incubation step disclosed herein, a purifying step is performed in order to enrich a capture agent complex such as, e.g., a recombinant polypeptide-agent complex, a coagulation factor-agent complex, a Factor VII-antibody complex, a Factor VIII-antibody complex, and a Factor IX-antibody complex. Generally, complex purification may include capture of the complex to a more concentrated form, intermediate purification steps to remove impurities, and/or polishing to remove additional impurities and protein variants. See, e.g., Current Protocols in Protein Science, "Conventional chromatographic Separations," Ch. 8-9, (John Wiley & Sons Inc., Hoboken, N.J., 1995). Common purification methods include, without limitation, affinity chromatography, gel filtration, precipitation, and/or size exclusion chromatography. Processes useful as intermediate or polishing steps include cation-exchange chromatography, anion-exchange chromatography, hydrophobic-interaction chromatography, and ceramic hydroxyapatite chromatography, reverse-phase HPLC, gel filtration, precipitation, diafiltration, affinity chromatography, or chromatofocusing.

Detecting the presence or an activity of a recombinant polypeptide disclosed herein can be accomplished by any assay that can qualitatively or quantitatively measure a characteristic indicative of the presence or an activity associated with the polypeptide being monitored, including, without limitation, an in vitro assay, a cell-based assay, or an in vivo assay. In addition, an assay may be a non-specific polypeptide assay, such as, e.g., UV absorption assay or a chemical-based assay like a Bradford assay or a biuret assay, or a specific polypeptide assay, such as, e.g., a chromogenic assay, a colorimetirc assay, a chronometric assay, a chemiluminescense assay, an electrochemiluminescence assay, a bioluminescence assay, a fluorogenic assay, a resonance energy transfer assay, a plane polarization assay, a flow cytometry assay, an immuno-based assay or an activity assay like an enzymatic activity, an inhibitory activity, a coagulation activity, or a polymerization activity. The actual assay used to detect a characteristic of a polypeptide as disclosed herein can be determined by a person of ordinary skill in the art by taking into account factors, including, without limitation, the polypeptide being assayed, the amount of polypeptide present, the characteristic being assayed, and the preference of the person of ordinary skill in the art. Detecting the presence or an activity of a recombinant polypeptide disclosed herein can be practiced in a singleplex or multiplex fashion.

Detection of the presence or activity of a polypeptide is indicative of the presence of the recombinant polypeptide comprising the modification.

Non-limiting examples of immuno-based assays include immunoblot analysis, like Western blotting and dot-blotting, immunoprecipitation analysis, enzyme-linked immunosorbent analysis (ELISA), and sandwich ELISA. The detection of the signal can be achieved using autoradiography with imaging or phosphorimaging (AU), chemiluminescense (CL), electrochemiluminescence (ECL), bioluminescence (BL), fluorescence, resonance energy transfer, plane polarization, colormetric, or flow cytometry (FC). Descriptions of immuno-based detection systems are disclosed in, e.g., Michael M. Rauhut, Chemiluminescence, In Kirk-Othmer Concise Encyclopedia of Chemical Technology (Ed. Grayson, 3rd ed, John Wiley and Sons, 1985); A. W. Knight, *A Review of Recent Trends in Analytical Applications of Electrogenerated Chemiluminescence*, Trends Anal. Chem. 18(1): 47-62 (1999); K. A. Fahnrich, et al., *Recent Applications of Electrogenerated Chemiluminescence in Chemical Analysis*, Talanta 54(4): 531-559 (2001); *Commonly Used Techniques in Molecular Cloning*, pp. A8.1-A8-55 (Sambrook & Russell, eds., Molecular Cloning A Laboratory Manual, Vol. 3, 3$^{rd}$ ed. 2001); Detection Systems, pp. A9.1-A9-49 (Sambrook & Russell, eds., Molecular Cloning A Laboratory Manual, Vol. 3, 3$^{rd}$ ed. 2001); Electrogenerated Chemiluminescence, (Ed. Allen J. Bard, Marcel Dekker, Inc., 2004), each of which is hereby incorporated by reference in its entirety.

A chromogenic assay using peptide substrates composed of a specific oligopeptide or polypeptide moiety and a chromophore (dye carrier) and are customarily used for determining factors possessing protease activity, for example for determining coagulation factors in blood and plasma samples. The chromogenic peptide substrate, which is initially colorless, is cleaved, in dependence on the quantity and/or activity of a recombinant polypeptide disclosed herein which is present in the sample, thereby releasing the chromophore. Cleavage changes the optical properties of the product, which are different from those of the uncleaved substrate and which can be measured by means of spectrophotometry. Non-limiting examples of chromogenic groups which can be coupled to a peptide substrate are para-nitroaniline (pNA), 5-amino-2-nitrobenzoic acid (ANBA), 7-amino-4-methoxycoumarin (ANC), quinonylamide (QUA), dimethyl 5-aminoisophthalate (DPA) and their derivatives. Fluorogenic substrates include, without limitation, Z-Gly-Pro-Arg-AMC [Z=Benzyloxycarbonyl; AMC=7-amino-4-methylcoumarin], homovanillic acid, 4-hydroxy-3-methoxyphenylacetic acid, reduced phenoxazines, reduced benzothiazines, Amplex®, resorufin β-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236, incorporated by reference), 4-methylumbelliferyl β-D-galactopyranoside, carboxyumbelliferyl β-D-galactopyranoside and fluorinated coumarin β-D-galactopyranosides (U.S. Pat. No. 5,830,912, incorporated by reference).

A non-limiting activity assay is a chromogenic assay based on the blood coagulation cascade can be used to detect FVIII activity. In this assay, thrombin activated Factor VIII forms a complex with Factor IXa, and this complex subsequently activates Factor X. Activated Factor X activity can be accessed by the hydrolysis of a chromogenic substrate which liberates a chromogenic group like p-nitro-aniline (pNA). The initial rate of pNA release, as determined by a change in absorbance per minute measured at 405 nm in dOD, is proportional to the Factor Xa activity and subsequently to the FVIII activity in the sample. By using excess of Factor IXa, and Factor X, the rate of activation of Factor X is solely proportional to the amount of thrombin cleaved Factor VIII present in the sample. Alternatively, Factor IXa activity can be determined by altering conditions so that Factor VIII and Factor X are in excess, and as such, Factor IXa is rate limiting. Similarly, Factor X activity can be determined by altering conditions so that Factor VIII and Factor IXa are in excess, and as such, Factor X is rate limiting. Thus, Factor VIII activity, as well as Factor IXa and Factor X, can be detected using a chromogenic assay based on the blood coagulation cascade.

Another non-limiting activity assay is a chromogenic assay based on the blood coagulation cascade can be used to detect thrombin activity. Such assays may use the pNA-coupled peptide substrate Ala-Gly-Arg-pNA (PEFACHROM®TG, Pentapharm Ltd., Basle, Switzerland) or the AMC-coupled peptide substrate Gly-Cly-Arg-AMC (Bachem). Other suitable peptide substrates which are cleaved by thrombin are those of the general formula Msc-Val-Xaa-$R_1$, in which Msc is methylsulfonyl-ethyloxycarbonyl, Val is the amino acid valine and Xaa is an amino acid residue, which comprises a terminal guanidino group or ureido group which is separated from the peptide backbone by at least two carbon atoms, and in which $R_1$ is a chromogenic group, with the peptide Msc-Val-Arg-$R_1$ or Msc-Val-Arg-pNA. Other examples of chromogenic peptide substrates having specificities for different proteases can be found, for example, in U.S. Pat. No. 4,508,644 which is hereby incorporated by reference in its entirety.

A non-limiting activity assay is a one-stage clotting assay that applies the Partial Activated Partial Thromboplastin Time (APTT) can be used to detect FVIII activity. In this chronometric assay, samples comprising Factor VIII, along with $CaCl_2$, are added to Factor VIII deficient plasma in order to promote coagulation and the effect of this sample on APTT clotting time of the plasma can be determined on a MDA-II apparatus (BioMerieux, Marcy-I'Etoile) and is a measure of the Factor VIII activity. Activities of unknown samples are calculated by comparing the Factor VIII activity observed with a standard curve generated from known Factor VIII activity samples. Coagulant activity can be measured by chronometric assay on a robotic platform and the chronometric activity of modified compounds can be compared to the activity of a wild-type FVIII used as an internal standard. This blood clotting assay may also be used for any other protein involved in the blood coagulation cascade by using a plasma deficient in the protein being assayed.

The methods disclosed herein may be evaluated by several parameters including, e.g., accuracy, precision, limit of detection (LOD), limits of quantitation (LOQ), range, specificity, selectivity, linearity, ruggedness, and system suitability. The accuracy of a method is the measure of exactness of an analytical method, or the closeness of agreement between the measured value and the value that is accepted as a conventional true value or an accepted reference value. The precision of a method is the degree of agreement among individual test results, when the procedure is applied repeatedly to multiple samplings of a homogeneous sample. As such, precision evaluates 1) within assay variability; 2) within-day variability (repeatability); and 3) between-day variability (intermediate precision); and 4) between-lab variability (reproducibility). Coefficient of variation (CV %) is a quantitative measure of precision expressed relative to the observed or theoretical mean value.

A method disclosed herein must be able to detect, over background, the presence or activity of a recombinant polypeptide disclosed herein. The limit of detection (LOD) of a method refers to the concentration of a recombinant polypeptide disclosed herein which gives rise to a signal that is significantly different from the negative control or blank and represents the lowest concentration of a recombinant polypeptide disclosed herein that can be distinguished from background.

Thus, in an embodiment, a method disclosed herein can detect the LOD of a recombinant polypeptide disclosed herein at an amount that is significantly different from a negative control or blank. In aspect of this embodiment, a method disclosed herein has an LOD of, e.g., 10 ng or less, 9 ng or less, 8 ng or less, 7 ng or less, 6 ng or less, 5 ng or less, 4 ng or less, 3 ng or less, 2 ng or less, 1 ng or less of a recombinant polypeptide disclosed herein. In still other aspects of this embodiment, a method disclosed herein has an LOD of, e.g., 900 pg or less, 800 pg or less, 700 pg or less, 600 pg or less, 500 pg or less, 400 pg or less, 300 pg or less, 200 pg or less, 100 pg or less of a recombinant polypeptide disclosed herein. In further aspects of this embodiment, a method disclosed herein has an LOD of, e.g., 90 pg or less, 80 pg or less, 70 pg or less, 60 pg or less, 50 pg or less, 40 pg or less, 30 pg or less, 20 pg or less, 10 pg or less of a recombinant polypeptide disclosed herein. In other aspects of this embodiment, a method disclosed herein has an LOD of, e.g., 9 pg or less, 8 pg or less, 7 pg or less, 6 pg or less, 5 pg or less, 4 pg or less, 3 pg or less, 2 pg or less, 1 pg or less of a recombinant polypeptide disclosed herein. In yet other aspects of this embodiment, a method disclosed herein has an LOD of, e.g., 0.9 pg or less, 0.8 pg or less, 0.7 pg or less, 0.6 pg or less, 0.5 pg or less, 0.4 pg or less, 0.3 pg or less, 0.2 pg or less, 0.1 pg or less of a recombinant polypeptide disclosed herein.

In another aspect of this embodiment, a method disclosed herein has an LOD of, e.g., 10 nM or less or less, 9 nM or less, 8 nM or less, 7 nM or less, 6 nM or less, 5 nM or less, 4 nM or less, 3 nM or less, 2 nM or less, or 1 nM or less of a recombinant polypeptide disclosed herein. In other aspects of this embodiment, a method disclosed herein has an LOD of, e.g., 900 pM or less, 800 pM or less, 700 pM or less, 600 pM or less, 500 pM or less, 400 pM or less, 300 pM or less, 200 pM or less, or 100 pM or less of a recombinant polypeptide disclosed herein. In other aspects of this embodiment, a method disclosed herein has an LOD of, e.g., 100 pM or less, 90 pM or less, 80 pM or less, 70 pM or less, 60 pM or less, 50 pM or less, 40 pM or less, 30 pM or less, 20 pM or less, or 10 pM or less of a recombinant polypeptide disclosed herein. In yet other aspects of this embodiment, a method disclosed herein has an LOD of, e.g., 10 pM or less of a BoNT/A, 9 pM or less, 8 pM or less, 7 pM or less, 6 pM or less, 5 pM or less, 4 pM or less, 3 pM or less, 2 pM or less, or 1 pM or less of a recombinant polypeptide disclosed herein. In still other aspects of this embodiment, a method disclosed herein has an LOD of, e.g., 1000 fM or less, 900 fM or less, 800 fM or less, 700 fM or less, 600 fM or less, 500 fM or less, 400 fM or less, 300 fM or less, 200 fM or less, or 100 fM or less of a recombinant polypeptide disclosed herein. In still other aspects of this embodiment, a method disclosed herein has an LOD of, e.g., 100 fM or less, 90 fM or less, 80 fM or less, 70 fM or less, 60 fM or less, 50 fM or less, 40 fM or less, 30 fM or less, 20 fM or less, or 10 fM or less of a recombinant polypeptide disclosed herein. In still other aspects of this embodiment, a method disclosed herein has an LOD of, e.g., 10 fM or less, 9 fM or less, 8 fM or less, 7 fM or less, 6 fM or less, 5 fM or less, 4 fM or less, 3 fM or less, 2 fM or less, or 1 fM or less of a recombinant polypeptide disclosed herein.

The limits of quantitation (LOQ) are the lowest and the highest concentrations of a recombinant polypeptide disclosed herein in a sample or specimen that can be measured with an acceptable level of accuracy and precision. The lower limit of quantitation refers to the lowest dose that a detection method can measure consistently from the background. The upper limit of quantitation is the highest dose that a detection method can measure consistently before saturation of the signal occurs. The linear range of the method is the area between the lower and the upper limits of quantitation. The linear range is calculated by subtracting lower limit of quantitation from the upper limit of quantitation. As used herein, the term "signal to noise ratio for the lower asymptote" refers to the signal detected in the method at the lower limit of detection divided by the background signal. As used herein, the term "signal to noise ratio for the upper asymptote" refers to the signal detected in the method at the upper limit of detection divided by the background signal.

Thus, in an embodiment, a method disclosed herein can detect the LOQ of a recombinant polypeptide disclosed herein at an amount that is significantly different from a negative control or blank. In aspect of this embodiment, a method disclosed herein has an LOQ of, e.g., 10 ng or less, 9 ng or less, 8 ng or less, 7 ng or less, 6 ng or less, 5 ng or less, 4 ng or less, 3 ng or less, 2 ng or less, 1 ng or less of a recombinant polypeptide disclosed herein. In still other aspects of this embodiment, a method disclosed herein has an LOQ of, e.g., 900 pg or less, 800 pg or less, 700 pg or less, 600 pg or less, 500 pg or less, 400 pg or less, 300 pg or less, 200 pg or less, 100 pg or less of a recombinant polypeptide disclosed herein. In further aspects of this embodiment, a method disclosed herein has an LOQ of, e.g., 90 pg or less, 80 pg or less, 70 pg or less, 60 pg or less, 50 pg or less, 40 pg or less, 30 pg or less, 20 pg or less, 10 pg or less of a recombinant polypeptide disclosed herein. In other aspects of this embodiment, a method disclosed herein has an LOQ of, e.g., 9 pg or less, 8 pg or less, 7 pg or less, 6 pg or less, 5 pg or less, 4 pg or less, 3 pg or less, 2 pg or less, 1 pg or less of a recombinant polypeptide disclosed herein. In yet other aspects of this embodiment, a method disclosed herein has an LOQ of, e.g., 0.9 pg or less, 0.8 pg or less, 0.7 pg or less, 0.6 pg or less, 0.5 pg or less, 0.4 pg or less, 0.3 pg or less, 0.2 pg or less, 0.1 pg or less of a recombinant polypeptide disclosed herein.

In another aspect of this embodiment, a method disclosed herein has an LOQ of, e.g., 10 nM or less, 9 nM or less, 8 nM or less, 7 nM or less, 6 nM or less, 5 nM or less, 4 nM or less, 3 nM or less, 2 nM or less, or 1 nM or less of a recombinant polypeptide disclosed herein. In other aspects of this embodiment, a method disclosed herein has an LOQ of, e.g., 900 pM or less, 800 pM or less, 700 pM or less, 600 pM or less, 500 pM or less, 400 pM or less, 300 pM or less, 200 pM or less, or 100 pM or less of a recombinant polypeptide disclosed herein. In other aspects of this embodiment, a method disclosed herein has an LOQ of, e.g., 100 pM or less, 90 pM or less, 80 pM or less, 70 pM or less, 60 pM or less, 50 pM or less, 40 pM or less, 30 pM or less, 20 pM or less, or 10 pM or less of a recombinant polypeptide disclosed herein. In yet other aspects of this embodiment, a method disclosed herein has an LOQ of, e.g., 10 pM or less of a recombinant polypeptide disclosed herein, 9 pM or less, 8 pM or less, 7 pM or less, 6 pM or less, 5 pM or less, 4 pM or less, 3 pM or less, 2 pM or less, or 1 pM or less of a recombinant polypeptide disclosed herein. In still other aspects of this embodiment, a method disclosed herein has an LOQ of, e.g., 1000 fM or less, 900 fM or less, 800 fM or less, 700 fM or less, 600 fM or less, 500 fM or less, 400 fM or less, 300 fM or less, 200 fM or less, or 100 fM or less of a recombinant polypeptide disclosed herein. In still other aspects of this embodiment, a method disclosed herein has an LOQ of, e.g., 100 fM or less, 90 fM or less, 80 fM or less, 70 fM or less, 60 fM or less, 50 fM or less, 40 fM or less, 30 fM or less, 20 fM or less, or 10 fM or less of a recombinant polypeptide disclosed herein. In still other aspects of this embodiment, a method disclosed herein has an LOQ of, e.g., 10 fM or less, 9 fM or less, 8 fM or less, 7 fM or less, 6 fM or less, 5 fM or less, 4 fM or less, 3 fM or less, 2 fM or less, or 1 fM or less of a recombinant polypeptide disclosed herein.

A method disclosed herein may have a precision of no more than 50%. In aspects of this embodiment, a method disclosed herein may have a precision of no more than 50%, no more than 40%, no more than 30%, or no more than 20%. In other aspects of this embodiment, a method disclosed herein has a precision of no more than 15%, no more than 10%, or no more than 5%. In other aspects of this embodiment, a method disclosed herein may have a precision of no more than 4%, no more than 3%, no more than 2%, or no more than 1%.

An method disclosed herein may have an accuracy of at least 50%. In aspects of this embodiment, a method disclosed herein may have an accuracy of at least 50%, at least 60%, at least 70%, or at least 80%. In other aspects of this embodiment, a method disclosed herein may have an accuracy of at least 85%, at least 90%, or at least 95%. In other aspects of this embodiment, a method disclosed herein may have an accuracy of at least 96%, at least 97%, at least 98%, or at least 99%.

A method disclosed herein may have a signal to noise ratio for the lower asymptote that is statistically significant and a signal to noise ratio for the upper asymptote that is statistically significant. In aspects of this embodiment, a method disclosed herein may have a signal to noise ratio for the lower asymptote of, e.g., at least 3:1, at least 4:1, at least 5:1, at least 6:1, at least 7:1, at least 8:1, at least 9:1, at least 10:1, at least 15:1 or at least 20:1. In other aspects of this embodiment, a method disclosed herein may have a signal to noise ratio for the upper asymptote of, e.g., at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1.

The specificity of a method disclosed herein defines the ability of the method to measure a recombinant polypeptide disclosed herein to the exclusion of other relevant components, such as, e.g., a partially-active or inactive recombinant polypeptide disclosed herein. The selectivity of a method disclosed herein describes the ability of the method to differentiate various substances in a sample. The linearity of a method disclosed herein describes the ability of the method to elicit results that are directly, or by a well defined mathematical transformation, proportional to the concentration of a recombinant polypeptide disclosed herein in the sample. Thus in an embodiment, a method disclosed herein may distinguish a recombinant polypeptide disclosed herein from a partially-active recombinant polypeptide disclosed herein having, e.g., 70 or less, 60% or less, 50% or less, 40% or less, 30% or less, 20% or less, or 10% or less the activity of a fully-active recombinant polypeptide.

The ruggedness of a method disclosed herein describes the reproducibility of the results obtained for identical samples under normal (but variable) conditions of the method. Robustness of a method disclosed herein describes the ability of the method to measure of its capacity to remain unaffected by small but deliberate variations in the method parameters and provides an indication of its reliability in normal usage. Thus, whereas ruggedness evaluates unavoidable changes, robustness evaluates deliberate changes. Typical parameters evaluated by ruggedness and robustness include the effects of freeze/thaw, incubation times, incubation temperature, longevity of reagent, sample preparation, sample storage, cell passage number, lots of toxin, variability between purifications, and variability between nicking reactions. Robustness parameters for a method disclosed herein include the cell bank (beginning, middle and end of freeze), cell passage level, cell seeding density, cell stock density (how many days in culture), cell age in flask (waiting time to seeding), incubation time, different plates, excessive amounts of serum, and source of reagents. The system suitability of a method disclosed herein describes the ability of the method to determine method performance, including the performance of reagents and instruments, over time by analysis of a reference standard. System suitability is refers to the fact that equipment, electronics, assay performance, and samples to be analyzed, constitute an integrated system. System suitability can be evaluated by testing for parallelism, which is when plotting the log dose versus the response, serial dilutions of the reference and serial dilutions of the samples should give rise to parallel curves.

Aspects of the present specification disclose kits comprising one or more components useful for practicing the methods disclosed herein. The one or more components of a kit may comprising one or more capture agents disclosed herein, one or more solid phase supports, and/or one or more reagents necessary to detect the presence and/or an activity of a recombinant polypeptide comprising a modification disclosed herein. A kit disclosed herein can include a solid phase and a capture agent affixed to the solid phase. A kit disclosed herein may also comprise a recombinant polypeptide comprising a modificaiton useful as a positive control for capture agent and/or the assaying step. If desired, this component can be included in the test kit in multiple concentrations to facilitate the generation of a standard curve to which the signal detected in the test sample can be compared.

A kit generally includes a package with one or more containers holding the components, as one or more separate compositions or, optionally, as admixture where the compatibility of the reagents will allow. A kit can also include other material(s), which can be desirable from a user standpoint, such as a buffer(s), a diluent(s), a standard(s), and/or any other material useful in sample processing, washing, or conducting any other step of the assay. A kit disclosed herein may also include instructions for carrying out one or more methods disclosed herein. Instructions included in kits disclosed herein can be affixed to packaging material or can be included as a package insert. While the instructions are typically written or printed materials they are not limited to such. Any medium capable of storing such instructions and communicating them to an end user is contemplated by the embodiments disclosed herein. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

Aspects of the present specification may also be described as follows:

1. A method for detecting the presence of a recombinant polypeptide comprising a modification, the method comprising the steps of: incubating a sample including the recombinant polypeptide comprising the modification with a capture agent that selectively binds the modification under conditions allowing the selective binding of the capture agent to the modification, thereby forming a polypeptide-agent complex; purifying the polypeptide-agent complex from the sample; and assaying for the presence of the recombinant polypeptide and/or a polypeptide activity, wherein detection of the recombinant polypeptide and/or the polypeptide activity is indicative of the presence of the recombinant polypeptide comprising the modification.
2. The method according to embodiment 1, wherein the sample includes a polypeptide without the modification and/or a polypeptide with a different pattern of degree of modification.
3. The method according to embodiment 2, wherein the recombinant polypeptide is a growth factor, a cytokine, an immunomodulating agent, a hormone, an antibody, an enzyme, an enzyme inhibitor, a protease, a protease inhibitor, an esterase, a transferase, an oxidoreductase, a hydrolase, an asparaginase, an adenosine deaminase, a neurotoxin, a liver protein, a pancreatic protein, a muscle protein, a brain protein, a lung protein, or a blood protein.
4. The method according to embodiment 3, wherein the esterase is a butyrylcholinesterase or a acetylcholinesterase.
5. The method according to embodiment 3, wherein the cytokine is a chemokine, a lymphokine, a tumor necrosis factor, a hematopoietic factor.
6. The method according to embodiment 3, wherein the immunomodulating agent is an interleukin or an interferon.
7. The method according to embodiment 3, wherein the blood protein is an erythropoiesis-stimulating agent, a protease, a protease inhibitor, or a coagulation factor.
8. The method according to embodiment 7, the erythropoiesis-stimulating agent is an erythropoietin, an erythropoietin, an erthropoyetin, or a darbepoetin.
9. The method according to embodiment 7, the protease is trypsin, chymotrypsin, elastase, pepsin, or ADAMTS13.
10. The method according to embodiment 7, the protease inhibitor is α1-antitrypsin, α1-antichymotrypsin, C1-inhibitor, or α2-antiplasmin, antithrombin.
11. The method according to embodiment 7, wherein the coagulation factor is a Factor II, a Factor IIa, a Factor VII, a Factor VIIa, a Factor VIII, a Factor VIIIa, a Factor IX, a Factor IXa, a Factor X, or a Factor Xa.
12. The method according to embodiment 3, wherein the blood protein is ADAMTS-13, α1-antiplasmin, α2-antiplasmin, antithrombin, antithrombin III, cancer procoagulant, erythropoietin, Factor II, Factor IIa, Factor V, Factor Va, Factor VI, Factor VIa, Factor VII, Factor VIIa, Factor VIII, Factor VIIIa, Factor IX, Factor IXa, Factor X, Factor Xa, Factor XI, Factor XIa, Factor XII, Factor XIIa, Factor XIII, Factor XIIIa, fibronectin, fibrinogen (Factor I), heparin cofactor II, high-molecular-weight kininogen (HMWK), intramuscular immunoglobulin, intravenous immunoglobulin, plasmin, plasminogen, plasminogen activator inhibitor-1 (PAI1), plasminogen activator inhibitor-2 (PAI2), prekallikrein, prostacyclin, protein C, active protein C (APC), protein S, protein Z, protein Z-related protease inhibitor, thrombomodulin, tissue factor (Factor III), Tissue factor pathway inhibitor (TFPI), tissue plasminogen activator (t-PA), urokinase, and Von Willebrand Factor.
13. A method for detecting the presence of a recombinant coagulation factor comprising a modification, the method comprising the steps of:
    incubating a sample including the recombinant coagulation factor comprising the modification with a capture agent that selectively binds the modification under conditions allowing the selective binding of the capture agent to the modification, thereby forming a factor-agent complex;
    purifying the factor-agent complex from the sample; and
    assaying for the presence of the recombinant coagulation factor and/or a coagulation factor activity, wherein detection of the recombinant coagulation factor and/or the coagulation factor activity is indicative of the presence of the recombinant coagulation factor comprising the modification.
14. The method according to embodiment 13, wherein the sample further includes a coagulation factor without the modification and/or a coagulation factor with a different pattern of degree of modification.
15. The method according to any one of embodiments 13-14, wherein the coagulation factor is a Factor II, a Factor IIa, a Factor VII, a Factor VIIa, a Factor VIII, a Factor VIIIa, a Factor IX, a Factor IXa, a Factor X, or a Factor Xa.
16. The method according to any one of embodiments 1-15, wherein the modification is an acetate group, a phosphate group, a lipid group, or a carbohydrate group, a myristate group, a palmitate group, an isoprenoid group like a farnesol group and geranylgeraniol group, a glycosylphosphatidylinositol (GPI) group, a lipoate group, a flavin group, a heme C group, a 4'-phosphopantetheinyl group, a retinylidene group, a diphthamide group, an ethanolamine phosphoglycerol group, a hypusine group, an acetyl group, a formyl group, an alkyl group, a methyl group, an amide group, an amino acid, a butyl group, a carboxyl group, a glycosyl group, a polysialic acid (PSA) group, a hydroxyl group, a malonyl group, an iodine group, a phosphate group, an adenylyl group, a succinyl group, a sulfate group, a selenium group, a carbohydrate group, a starch group, a hydroxyl-ethyl starch (HES) group, a polysaccharide group, a sugar group, a polyethylene glycol (PEG) group, an ubiquitin group, a pullulane group, a chitosan group, a hyaluronic acid group, a chondroitin sulfate group, a dermatan sulfate group, a dextran group, a carboxymethyl-dextran group, a polyalkylene oxide (PAO) group, a polyalkylene glycol (PAG) group, a polypropylene glycol (PPG) group, a polyoxazoline group, a polyacryloylmorpholine group, a polyvinyl alcohol (PVA) group, a polycarboxylate group, a polyvinylpyrrolidone (PVP) group, a polyphosphazene group, a polyoxazoline group, a polyethylene-co-maleic acid anhydride group, a polystyrene-co-maleic acid anhydride group, a poly(1-hydroxymethylethylene hydroxymethylformal) (PHF) group, or a 2-methacryloyloxy-2'-ethyltrimethylammonium-phosphate (MPC) group.

17. The method according to any one of embodiments 1-16, wherein the modification is associated with the recombinant polypeptide by myristoylation, palmitoylation, isoprenylation (prenylation), glypiation, lipoylation, flavinylation, phosphopantetheinylation, retinylidenylation, diphthamidylation, ethanolamine phosphoglycerylation, hypusinylation, acylation, acetylation, formylation, alkylation, amidation, arginylation, polyglutamylation, polyglycylation, butyrylation, gamma-carboxylation, glycosylation, polysialylation, malonylation, hydroxylation, iodination, nucleosylation, oxidation, phosphoroesterfication, phosphoramidation, phosphorylation, adenylylation, propionylation, pyroglutamate, S-glutathionylation, S-nitrosylation, succinylation, sulfation, selenoylation, glycation, biotinylation, acylation, PEGylation, HESylation, Sylation, citrullination, deamidation, eliminylation, carbamylation, deimination, pupylation, neddylation, ubiquitination, SUMOylation, or ISGylation.

18. The method according to any one of embodiments 1-17, wherein the sample includes a purified preparation of the recombinant polypeptide, a partially purified preparation of the recombinant polypeptide, an unpurified preparation of the recombinant polypeptide, a formulated preparation of the recombinant polypeptide; a crude extract of the recombinant polypeptide, a fractionated extract of the recombinant polypeptide, a cell lysate including the recombinant polypeptide, or a biological sample.

19. The method according to embodiment 18, wherein the biological sample comprises cells, a tissue sample, a blood sample, a body fluid sample, or an organ sample taken directly from an individual.

20. The method according to embodiment 19, wherein the body fluid is urine, sputum, semen, feces, saliva, bile, cerebral fluid, nasal swab, urogenital swab, nasal aspirate, or spinal fluid.

21. The method according to embodiment 18, wherein the biological sample is a preparation derived from a sample taken directly from an individual.

22. The method according to embodiment 21, wherein the preparation derived from the sample taken directly from the individual is a plasma fraction of a blood sample, a serum fraction of a blood sample, or an eluate from a purification process.

23. The method according to any one of embodiments 1-22, wherein the sample is treated to improve detectability of the recombinant polypeptide or improve activity of the recombinant polypeptide.

24. The method according to embodiment 23, wherein the treatment comprises lysing, dilution, purification, extraction, filtration, distillation, separation, concentration, inactivation of interfering components, the addition of reagents, or any combination thereof.

25. The method according to any one of embodiments 1-24, wherein the capture agent has an association rate constant for a polypeptide comprising the modification of more than $1\times10^5$ $M^{-1}$ $s^{-1}$, more than $1\times10^6$ $M^{-1}$ $s^{-1}$, more than $1\times10^7$ $M^{-1}$ $s^{-1}$, or more than $1\times10^8$ $M^{-1}$ $s^{-1}$.

26. The method according to any one of embodiments 1-25, wherein the capture agent has a disassociation rate constant for a polypeptide comprising the modification of less than $1\times10^{-3}$ $s^{-1}$, less than $1\times10^{-4}$ $s^{-1}$, or less than $1\times10^{-5}$ $s^{-1}$.

27. The method according to any one of embodiments 1-26, wherein the capture agent has an equilibrium disassociation constant for a polypeptide comprising the modification of less than 0.500 nM, less than 0.450 nM, less than 0.400 nM, less than 0.350 nM, less than 0.300 nM, less than 0.250 nM, less than 0.200 nM, less than 0.150 nM, less than 0.100 nM, or less than 0.050 nM.

28. The method according to any one of embodiments 1-27, wherein the capture agent has an association rate constant for a polypeptide without a modification or a polypeptide with a different pattern or degree of modification of less than $1\times10^0$ $M^{-1}$ $s^{-1}$, less than $1\times10^1$ $M^{-1}$ $s^{-1}$, less than $1\times10^2$ $M^{-1}$ $s^{-1}$, less than $1\times10^3$ $M^{-1}$ $s^{-1}$, or less than $1\times10^4$ $M^{-1}$ $s^{-1}$.

29. The method according to any one of embodiments 1-28, wherein the capture agent has an association rate constant (Ka) for the recombinant polypeptide comprising a modification that is more than $1\times10^0$ $M^{-1}$ $s^{-1}$, more than $1\times10^1$ $M^{-1}$ $s^{-1}$, more than $1\times10^2$ $M^{-1}$ $s^{-1}$, more than $1\times10^3$ $M^{-1}$ $s^{-1}$ or more than $1\times10^4$ $M^{-1}$ $s^{-1}$ relative to the association rate constant (Ka) of the capture agent for a recombinant polypeptide without such a modification and/or the association rate constant (Ka) of the capture agent for a recombinant polypeptide with a different pattern or degree of modification.

30. The method according to any one of embodiments 1-28, wherein the capture agent has an association rate constant (Ka) for the recombinant polypeptide comprising a modification that is at least 2-fold more, at least 3-fold more, at least 4-fold more, at least 5-fold more, at least 6-fold more, at least 7-fold more, at least 8-fold more, at least 9-fold more, at least 10-fold more, at least 100-fold more, at least 1.000-fold more or at least 10.000-fold more then the association rate constant (Ka) of the capture agent for a recombinant polypeptide without such a modification and/or then the association rate constant (Ka) of the capture agent for a recombinant polypeptide with a different pattern or degree of modification.

31. The method according to any one of embodiments 1-28, wherein the capture agent has a binding specificity ratio for a recombinant polypeptide comprising a modification relative to a recombinant polypeptide without such a modification and/or relative to a recombinant polypeptide with a different pattern or degree of modification of at least 2:1, at least 3:1, at least 4:1, at least 5:1, at least 64:1, at least 7:1, at least 8:1, at least 9:1, at least 10:1, at least 15:1, at least 20:1, at least 25:1, at least 30:1, at least 35:1, or at least 40:1

32. The method according to any one of embodiments 1-31, wherein the capture agent is a multivalent capture agent.

33. The method according to any one of embodiments 1-32, wherein the capture agent distinguishes the recombinant polypeptide comprising a modification from the same polypeptide but without the modification.

34. The method according to any one of embodiments 1-33, wherein the capture agent distinguishes the recombinant polypeptide comprising a modification from the same polypeptide but with a different pattern or degree of the same modification.

35. The method according to any one of embodiments 1-34, wherein the capture agent is an antibody.

36. The method according to embodiment 35, wherein the antibody is an anti-acetate antibody, an anti-phosphate antibody, an anti-lipid antibody, or an anti-carbohydrate antibody, an anti-myristate antibody, an anti-palmitate antibody, an anti-isoprenoid antibody like an anti-farnesol antibody and geranylgeraniol antibody, an anti-glycosylphosphatidylinositol (GPI) antibody, an anti-lipoate antibody, an anti-flavin antibody, an anti-heme C antibody, an anti-4'-phosphopantetheinyl antibody, an anti-retinylidene antibody, an anti-diphthamide antibody, an anti-ethanolamine phosphoglycerol antibody, an anti-hypusine antibody, an anti-acetyl antibody, an anti-formyl antibody, an anti-alkyl antibody, an anti-methyl antibody, an anti-amide antibody, an anti-amino acid antibody, an anti-butyl antibody, an anti-carboxyl antibody, an anti-glycosyl antibody, an anti-polysialic acid antibody, an anti-hydroxyl antibody, an anti-malonyl antibody, an anti-iodine antibody, an anti-phosphate antibody, an anti-adenylyl antibody, an anti-succinyl antibody, an anti-sulfate antibody, an anti-selenium antibody, an anti-carbohydrate antibody, an anti-polysaccharide antibody, an anti-starch antibody, an anti-hydroxyl-ethyl starch (HES) antibody, an anti-sugar antibody, an anti-polyethelene glycol (PEG) antibody, an anti-ubiquitin antibody, an anti-pullulane antibody, an anti-chitosan antibody, an anti-hyaluronic acid antibody, an anti-chondroitin sulfate antibody, an anti-dermatan sulfate antibody, an anti-dextran antibody, an anti-carboxymethyl-dextran antibody, an anti-polyalkylene oxide (PAO) antibody, an anti-polyalkylene glycol (PAG) antibody, an anti-polypropylene glycol (PPG) antibody, an anti-polyoxazoline antibody, an anti-polyacryloylmorpholine antibody, an anti-polyvinyl alcohol (PVA) antibody, an anti-polycarboxylate antibody, an anti-polyvinylpyrrolidone (PVP) antibody, an anti-polyphosphazene antibody, an anti-polyoxazoline antibody, an anti-polyethylene-co-maleic acid anhydride antibody, an anti-polystyrene-co-maleic acid anhydride antibody, an anti-poly(1-hydroxymethylethylene hydroxymethylformal) (PHF) antibody, or an anti-2-methacryloyloxy-2'-ethyltrimethylammonium-phosphate (MPC) antibody.

37. The method according to any one of embodiments 1-36, wherein the recombinant polypeptide comprising the modification or the recombinant coagulation factor comprising the modification is a PEGylation Factor II, a PEGylation Factor IIa, a polysialylation Factor II, a polysialylation Factor IIa, a HESylation Factor II, a HESylation Factor IIa, a Sylation Factor II, or a Sylation Factor IIa.

38. The method according to any one of embodiments 1-36, wherein the recombinant polypeptide comprising the modification or the recombinant coagulation factor comprising the modification is a PEGylation Factor VII, a PEGylation Factor VIIa, a polysialylation Factor VII, a polysialylation Factor VIIa, a HESylation Factor VII, a HESylation Factor VIIa, a Sylation Factor VII, or a Sylation Factor VIIa.

39. The method according to any one of embodiments 1-36, wherein the recombinant polypeptide comprising the modification or the recombinant coagulation factor comprising the modification is a PEGylation Factor VIII, a PEGylation Factor VIIIa, a polysialylation Factor VIII, a polysialylation Factor VIIIa, a HESylation Factor VIII, a HESylation Factor VIIIa, a Sylation Factor VIII, or a Sylation Factor VIIIa.

40. The method according to any one of embodiments 1-36, wherein the recombinant polypeptide comprising the modification or the recombinant coagulation factor comprising the modification is a PEGylation Factor IX, a PEGylation Factor IXa, a polysialylation Factor IX, a polysialylation Factor IXa, a HESylation Factor IX, a HESylation Factor IXa, a Sylation Factor IX, or a Sylation Factor IXa.

41. The method according to any one of embodiments 1-40, wherein the capture agent is attached to a solid support.

42. The method according to embodiment 41, wherein the solid support is a multi-well plate, a film, a tube, a sheet, a column, or a microparticle.

43. A method for detecting the presence of a PEGylated recombinant Factor VII, the method comprising the steps of: incubating a sample including the PEGylated recombinant Factor VII with an anti-PEG antibody under conditions allowing the selective binding of the anti-PEG antibody to the PEGylated recombinant Factor VII, thereby forming a Factor VII-antibody complex; purifying the Factor VII-antibody complex from the sample; and assaying for the presence of the recombinant Factor VII and/or a Factor VII activity, wherein detection of the Factor VII and/or the Factor VII activity is indicative of the presence of the PEGylated recombinant Factor VII, wherein the PEGylated recombinant Factor VII is a Factor VII and/or a Factor VIIa.

44. A method for detecting the presence of a polysialylated recombinant Factor VII, the method comprising the steps of: incubating a sample including the polysialylated recombinant Factor VII with an anti-PSA antibody under conditions allowing the selective binding of the anti-PSA antibody to the polysialylated recombinant Factor VII, thereby forming a Factor VII-antibody complex; purifying the Factor VII-antibody complex from the sample; and assaying for the presence of the recombinant Factor VII and/or a Factor VII activity, wherein detection of the Factor VII and/or the Factor VII activity is indicative of the presence of the polysialylated recombinant Factor VII, wherein the polysialylated recombinant Factor VII is a Factor VII and/or a Factor VIIa.

45. A method for detecting the presence of a HESylated recombinant Factor VII, the method comprising the steps of: incubating a sample including the HESylated recombinant Factor VII with an anti-S antibody under conditions allowing the selective binding of the anti-S antibody to the HESylated recombinant Factor VII, thereby forming a Factor VII-antibody complex; purifying the Factor VII-antibody complex from the sample; and assaying for the presence of the recombinant Factor VII and/or a Factor VII activity, wherein detection of the Factor VII and/or the Factor VII activity is indicative of the presence of the HESylated recombinant Factor VII, wherein the HESylated recombinant Factor VII is a Factor VII and/or a Factor VIIa.

46. A method for detecting the presence of a Sylated recombinant Factor VII, the method comprising the steps of: incubating a sample including the Sylated recombinant Factor VII with an anti-S antibody under conditions allowing the selective binding of the anti-S antibody to the Sylated recombinant Factor VII, thereby forming a Factor VII-antibody complex; purifying the Factor VII-antibody complex from the sample; and assaying for the presence of the recombinant Factor VII and/or a Factor VII activity, wherein detection of the Factor VII and/or the Factor VII activity is indicative of the presence of the Sylated recombinant Factor VII, wherein the Sylated recombinant Factor VII is a Factor VII and/or a Factor VIIa.

47. A method for detecting the presence of a PEGylated recombinant Factor VIII, the method comprising the steps of: incubating a sample including the PEGylated recombinant Factor VIII with an anti-PEG antibody under conditions allowing the selective binding of the anti-PEG antibody to the PEGylated recombinant Factor VIII, thereby forming a Factor VIII-antibody complex; purifying the Factor VIII-antibody complex from the sample; and assaying for the presence of the recombinant Factor VIII and/or a Factor VIII activity, wherein detection of the Factor VIII and/or the Factor VIII activity is indicative of the presence of the PEGylated recombinant Factor VIII, wherein the PEGylated recombinant Factor VIII is a Factor VII and/or a Factor VIIIa.

48. A method for detecting the presence of a polysialylated recombinant Factor VIII, the method comprising the steps of: incubating a sample including the polysialylated recombinant Factor VIII with an anti-PSA antibody under conditions allowing the selective binding of the anti-PSA antibody to the polysialylated recombinant Factor VIII, thereby forming a Factor VIII-antibody complex; purifying the Factor VIII-antibody complex from the sample; and assaying for the presence of the recombinant Factor VIII and/or a Factor VIII activity, wherein detection of the Factor VIII and/or the Factor VIII activity is indicative of the presence of the polysialylated recombinant Factor VIII, wherein the polysialylated recombinant Factor VIII is a Factor VII and/or a Factor VIIIa.

49. A method for detecting the presence of a HESylated recombinant Factor VIII, the method comprising the steps of: incubating a sample including the HESylated recombinant Factor VIII with an anti-S antibody under conditions allowing the selective binding of the anti-S antibody to the HESylated recombinant Factor VIII, thereby forming a Factor VIII-antibody complex; purifying the Factor VIII-antibody complex from the sample; and assaying for the presence of the recombinant Factor VIII and/or a Factor VIII activity, wherein detection of the Factor VIII and/or the Factor VIII activity is indicative of the presence of the HESylated recombinant Factor VIII, wherein the HESylated recombinant Factor VIII is a Factor VII and/or a Factor VIIIa.

50. A method for detecting the presence of a Sylated recombinant Factor VIII, the method comprising the steps of: incubating a sample including the Sylated recombinant Factor VIII with an anti-S antibody under conditions allowing the selective binding of the anti-S antibody to the Sylated recombinant Factor VIII, thereby forming a Factor VIII-antibody complex; purifying the Factor VIII-antibody complex from the sample; and assaying for the presence of the recombinant Factor VIII and/or a Factor VIII activity, wherein detection of the Factor VIII and/or the Factor VIII activity is indicative of the presence of the Sylated recombinant Factor VIII, wherein the Sylated recombinant Factor VIII is a Factor VII and/or a Factor VIIIa.

51. A method for detecting the presence of a PEGylated recombinant Factor IX, the method comprising the steps of: incubating a sample including the PEGylated recombinant Factor IX with an anti-PEG antibody under conditions allowing the selective binding of the anti-PEG antibody to the PEGylated recombinant Factor IX, thereby forming a Factor IX-antibody complex; purifying the Factor IX-antibody complex from the sample; and assaying for the presence of the recombinant Factor IX and/or a Factor IX activity, wherein detection of the Factor IX and/or the Factor IX activity is indicative of the presence of the PEGylated recombinant Factor IX, wherein the PEGylated recombinant Factor IX is a Factor IX and/or a Factor IXa.

52. A method for detecting the presence of a polysialylated recombinant Factor IX, the method comprising the steps of: incubating a sample including the polysialylated recombinant Factor IX with an anti-PSA antibody under conditions allowing the selective binding of the anti-PSA antibody to the polysialylated recombinant Factor IX, thereby forming a Factor IX-antibody complex; purifying the Factor IX-antibody complex from the sample; and assaying for the presence of the recombinant Factor IX and/or a Factor IX activity, wherein detection of the Factor IX and/or the Factor IX activity is indicative of the presence of the polysialylated recombinant Factor IX, wherein the polysialylated recombinant Factor IX is a Factor IX and/or a Factor IXa.

53. A method for detecting the presence of a HESylated recombinant Factor IX, the method comprising the steps of: incubating a sample including the HESylated recombinant Factor IX with an anti-S antibody under conditions allowing the selective binding of the anti-S antibody to the HESylated recombinant Factor FIX, thereby forming a Factor IX-antibody complex; purifying the Factor IX-antibody complex from the sample; and assaying for the presence of the recombinant Factor IX and/or a Factor IX activity, wherein detection of the Factor IX and/or the Factor IX activity is indicative of the presence of the HESylated recombinant Factor IX, wherein the HESylated recombinant Factor IX is a Factor IX and/or a Factor IXa.

54. A method for detecting the presence of a Sylated recombinant Factor IX, the method comprising the steps of: incubating a sample including the Sylated recombinant Factor IX with an anti-S antibody under conditions allowing the selective binding of the anti-S antibody to the Sylated recombinant Factor FIX, thereby forming a Factor IX-antibody complex; purifying the Factor IX-antibody complex from the sample; and assaying for the presence of the recombinant Factor IX and/or a Factor IX activity, wherein detection of the Factor IX and/or the Factor IX activity is indicative of the presence of the Sylated recombinant Factor IX, wherein the Sylated recombinant Factor IX is a Factor IX and/or a Factor IXa.

55. The method according to any one of embodiments 1-54, wherein the assaying step is performed using a qualitative assay or a quantitative assay.

56. The method according to any one of embodiments 1-55, wherein the assaying step is performed using an in vitro assay, a cell-based assay, or an in vivo assay.

57. The method according to any one of embodiments 1-56, wherein the assaying step is performed using a non-specific polypeptide assay or a specific polypeptide assay.

58. The method according to embodiment 57, wherein the non-specific polypeptide assay is a UV absorption assay, a biuret assay, or a Bradford assay.

59. The method according to embodiment 57, wherein the specific polypeptide assay is a chromogenic assay, a colorimetirc assay, a chronometric assay, a chemiluminescense assay, an electrochemiluminescence assay, a bioluminescence assay, a fluorogenic assay, a resonance energy transfer assay, a plane polarization assay, a flow cytometry assay, an immuno-based assay or an activity assay.

60. The method according to embodiment 59, wherein the activity assay is an enzymatic activity assay, an inhibitory activity assay, a coagulation activity assay, or a polymerization activity assay.

61. The method according to any one of embodiments 1-60, wherein selective binding of the capture agent occurs at a neutral to alkaline pH.

62. The method according to any one of embodiments 1-61, wherein the recombinant polypeptide is a therapeutic polypeptide.

63. The method according to embodiment 63, wherein the thereapeutic polypeptide is Factor IX (FIX), Factor VIII (FVIII), Factor VIIa (FVIIa), Von Willebrand Factor (VWF), Factor FV (FV), Factor X (FX), Factor XI (FXI), Factor XII (FXII), thrombin (FII), protein C, protein S, tPA, PAI-1, tissue factor (TF), ADAMTS 13 protease, IL-1 alpha, IL-1 beta, IL-3, IL-4, IL-5, IL-6, IL-11, colony stimulating factor-1 (CSF-1), M-CSF, SCF, GM-CSF, granulocyte colony stimulating factor (G-CSF), EPO, interferon-α (IFN-α), consensus interferon, IFN-β, IFN-γ, IFN-ω, IL-7, IL-8, IL-9, IL-10, IL-12, IL-13, IL-14, IL-15, IL-16, IL-17, IL-18, IL-19, IL-20, IL-21, IL-22, IL-23, IL-24, IL-31, IL-32 alpha, IL-33, thrombopoietin (TPO), Ang-1, Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, cytokine-induced neutrophil chemotactic factor 2β, endothelial cell growth factor, endothelin 1, epidermal growth factor, epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neuropoietin, neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, TNF0, TNF1, TNF2, transforming growth factor .alpha., transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, thymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator, IgG, IgE, IgM, IgA, and IgD, α-galactosidase, β-galactosidase, DNAse, fetuin, leutinizing hormone, estrogen, insulin, albumin, lipoproteins, fetoprotein, transferrin, thrombopoietin, urokinase, integrin, thrombin, leptin, Humira (adalimumab), Prolia (denosumab), Enbrel (etanercept), or a biologically active fragment, derivative or variant thereof.

64. A kit comprising one or more components useful for practicing a method according to any one of embodiments 1-64.

65. The kit according to claim 64, wherein the one or more components comprises one or more capture agents, one or more solid phase supports, and/or one or more reagents necessary to detect the presence and/or an activity of a recombinant polypeptide.

66. The kit according to claim 65, wherein the capture agent is affixed to the solid phase.

67. The kit according to any one of embodiments 64-66, wherein the kit further comprises a recombinant polypeptide comprising a modificaiton useful as a positive control for capture agent and/or the assaying step.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of modification-dependant activity assays disclosed herein and products processed using these methods.

Example 1

MDAA for PEGylated FVIII in PBS

This example illustrates that a MDAA for PEGylated FVIII can be conducted in a buffered solution.

To attach a modification-recognizing antibody to a solid support, 0.43 mg/mL of rabbit anti-PEG antibodies (B47-2061-1; Epitomics, Inc., Burlingame, Calif.) was diluted 1/50 in 0.1 M $NaHCO_3$—Na2CO3, pH 9.5 and incubated in the wells of a F96 Maxisorp plate (100 μL/well) at 0±10° C. overnight. The plates were then washed with Washing Buffer comprising phosphate-buffered saline (PBS; 8 g/L NaCl, 0.2 g/L KCl, 0.2 g/L KH2PO4, 1.26 g/L $Na_2$HPO4×2 H2O, native pH) and 0.05% Tween 20. The wells of the plate were then blocked by incubation 200 μL/well of Dilution Buffer comprising PBS and 10 mg/mL human serum albumin at 37±5° C. for 60±10 minutes. The blocked wells were then washed with Washing Buffer.

To selectively bind a sample to a solid support, 100 μL of the following samples were added to a well 1) a dilution series of PEGylated recombinant FVIII standard prepared using PBS containing 10 mg/mL human serum albumin (HSA) or 2) a dilution series of human reference plasma prepared using PBS containing 10 mg/mL HSA. PEGylated recombinant FVIII with a degree of PEGylation of about 2 was used and had an FVIII:C activity of 2333 IU FVIII/mL, measured with a chromogenic method, and contained 56.2 μg/mL bound PEG/mL. The samples were loaded to the plate and incubated at about 18° C. to about 26° C. for 60±10 minutes. Under these conditions, PEGylated recombinant FVIII selectively bound to the solid support by means of its PEG moiety using an anti-PEG antibody. The plate was then washed 6 times with Washing Buffer followed by incubation with 200 μL/well of a FVIII dilution buffer comprising 3.4 g/L imidazole, 5.85 g/L NaCl; 10 mg/mL HSA, pH 7.4. This equilibration was done at room temperature for 3 minutes. After a washing step with Washing Buffer, the wells were emptied and FVIII activity was measured with a chromogenic assay following the standard chromogenic procedure using the Immunochrom FVIII kit (Technoclone, GmbH, Vienna, Austria). The wells were filled with 20 μL FVIII dilution buffer followed by the sequential addition of 20 μL reagent A and reagent B. The plate was then incubated at 37±5° C. for 5 minutes. Then pre-warmed substrate solution was added (100 μL/well) and incubated at 37±5° C. for 5 minutes. Finally, the reaction was stopped by adding 20% acetic acid (40 μL/well). Subsequently, the plate was measured at 405 nm (reference wavelength 620 nm) with an ELISA reader.

FIG. 1 shows the concentration-response curves obtained for the PEGylated FVIII preparation and a human reference plasma preparation. The dose-response curve obtained for the PEGylated FVIII preparation, covering a FVIII activity range from 7.3 to 233 mIU/mL met accepted requirements for accuracy, precision and linearity and was thus deemed to be appropriate for extrapolating samples. In particular, the correlation coefficient of the log-log regression curve was 0.9993 with a mean accuracy of 100.1%, calculated as the mean relative agreement of the back-fitted concentrations with the nominal ones, and a precision of 4.9%, expressed as the standard deviation of this mean. Alternatively, a calibration curve based on a lin-lin regression analysis would be feasible as well. In this case, the 4-point calibration curve ranged only from 29.2 to 233 mIU/mL with a mean accuracy of 104.4% and a precision of 6.2%. These data favor the log-log approach for constructing the calibration curve because this approach provides a higher sensitivity together with higher accuracy and precision. Furthermore, the data demonstrated the absolute specificity of the approach for measuring modified FVIII only. Human reference plasma, containing non-modified, native human FVIII at a concentration of 1 IU/mL, did not elicit any substantial signal. These data demonstrated that the FVIII activity of PEGylated FVIII can be sensitively and specifically measured.

Example 2

MDAA for PEGylated FVIII in Human Plasma

This example illustrates that a MDAA for PEGylated FVIII can be conducted in the present of blood plasma.

A modification-recognizing antibody was attached to a solid support as described in Example 1, except that 100 μL/well coating antibody solution comprising 4 μg/mL rabbit anti-PEG antibodies (B47-2061-1; Epitomics, Inc., Burlingame, Calif.), 0.1 M $NaHCO_3$—Na2CO3, pH 9.5 was used.

Samples were selectively bound to a solid support and FVIII activity measured using the chromogenic assay as described in Example 1, except that 1) a first dilution series of recombinant PEGylated FVIII was prepared by diluting in PBS containing 30 mg/mL skimmed milk to obtain a dilution series from 1/10,000 to 1/320,000; 2) a second dilution series of recombinant PEGylated FVIII was prepared by diluting in human plasma; and 3) FVIII activity was measured in the chromogenic assay using an incubation time of 15 minutes for the substrate reaction at 37±5° C.

Figure 2:
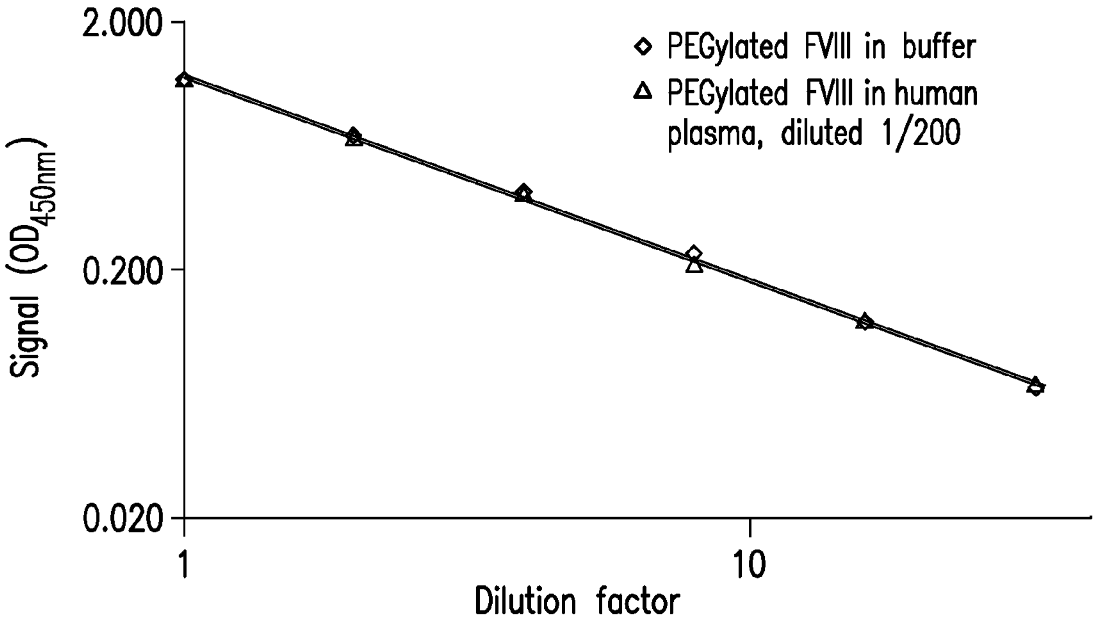
FIG. 2 shows a graph of the dose-response curves of a MDAA for PEGylated recombinant FVIII in sample matrices with different complexity (buffer vs plasma).

FIG. 2 shows the dose-response curves for the two preparations with different purities. The two concentration-response curves were very similar as shown by their slopes which differed by less than 1%. These data demonstrated that the modification-dependent activity assay for PEGylated FVIII performed adequately in human plasma, when diluted 1/200. Non-PEGylated FVIII, contained in plasma, did not contribute to the signal as shown by the overlapping concentration-response curves.

Example 3

Accuracy and Precision of MDAA for PEGylated FVIII

This example illustrates accuracy and precision of a MDAA for PEGylated FVIII.

To attach a modification-recognizing antibody to a solid support, 100 μL/well coating antibody solution comprising 4 μg/mL rabbit anti-PEG antibodies (B47-2061-1; Epitomics, Inc., Burlingame, Calif.), 0.1 M $NaHCO_3$—Na2CO3, pH 9.5 was incubated in the wells of a F96 Maxisorp plate at 0±10° C. overnight. The plates were then washed with Washing Buffer comprising PBS and 0.05% Tween 20. The wells of the plate were then blocked by incubation 200 μL/well of Blocking Buffer comprising PBS, 3% skimmed milk, and 50 mM benzamidine at about 18° C. to about 26° C. for 60±10 minutes. The blocked wells were then washed with Washing Buffer.

To selectively bind a sample to a solid support, 100 μL of the following samples were added to a well 1) a dilution series of PEGylated recombinant FVIII prepared using 1/10 human plasma solution diluted with PBS, 3% skimmed milk and 50 mM benzamidine and covered a FVIII concentration range from 2.2 mU/mL to 69 mU/mL; 2) a dilution series of human plasma prepared using 1/10 human plasma solution diluted with PBS, 3% skimmed milk and 50 mM benzamidine; or 3) a dilution series of a test control prepared using 1/10 human plasma solution diluted with PBS, 3% skimmed milk and 50 mM benzamidine PEGylated recombinant FVIII with a degree of PEGylation of about 2 was used and had an FVIII:C activity of 2333 IU FVIII/mL, measured with a chromogenic method, and contained 56.2 μg/mL bound PEG/mL. The samples were loaded to the plate and incubated at about 18° C. to about 26° C. for 120±10 minutes. Under these conditions, PEGylated recombinant FVIII selectively bound to the solid support by means of its PEG moiety using an anti-PEG antibody. The plate was then washed 6 times with Washing Buffer followed by incubation with 200 μL/well of a FVIII dilution buffer comprising 3.4 g/L imidazole, 5.85 g/L NaCl; 10 mg/mL HSA, pH 7.4. This equilibration was done at about 18° C. to about 26° C. for 5-10 minutes.

After a washing step with Washing Buffer, the wells were emptied and FVIII activity was measured with a chromogenic assay following the standard chromogenic procedure using the Immunochrom FVIII kit (Technoclone, GmbH, Vienna, Austria). The wells were filled with 20 μL FVIII dilution buffer followed by the sequential addition of 20 μL reagent A and reagent B. The plate was placed on a mixing device set at 500 rpm and incubated at about 18° C. to about 26° C. for 15 minutes. Then 100 μL/well of substrate solution was added and incubated at about 18° C. to about 26° C. for 45 minutes. Finally, the reaction was stopped by adding 40 μL/well of 20% acetic acid. The optical densities (ODs) are measured in an ELISA reader at 405 nm (reference wavelength 620 nm).

The quantitative evaluation is based on a double-logarithmic calibration curve. Blank-corrected mean ODs of the individual calibration curve standards will be correlated with their FVIII concentrations. The resulting calibration curve is used to calculate the samples' FVIII concentrations when their ODs are within the OD range covered by the calibration curve. Three different analysts participated in this study in order to check for an operator-dependent influence.

Figure 3:
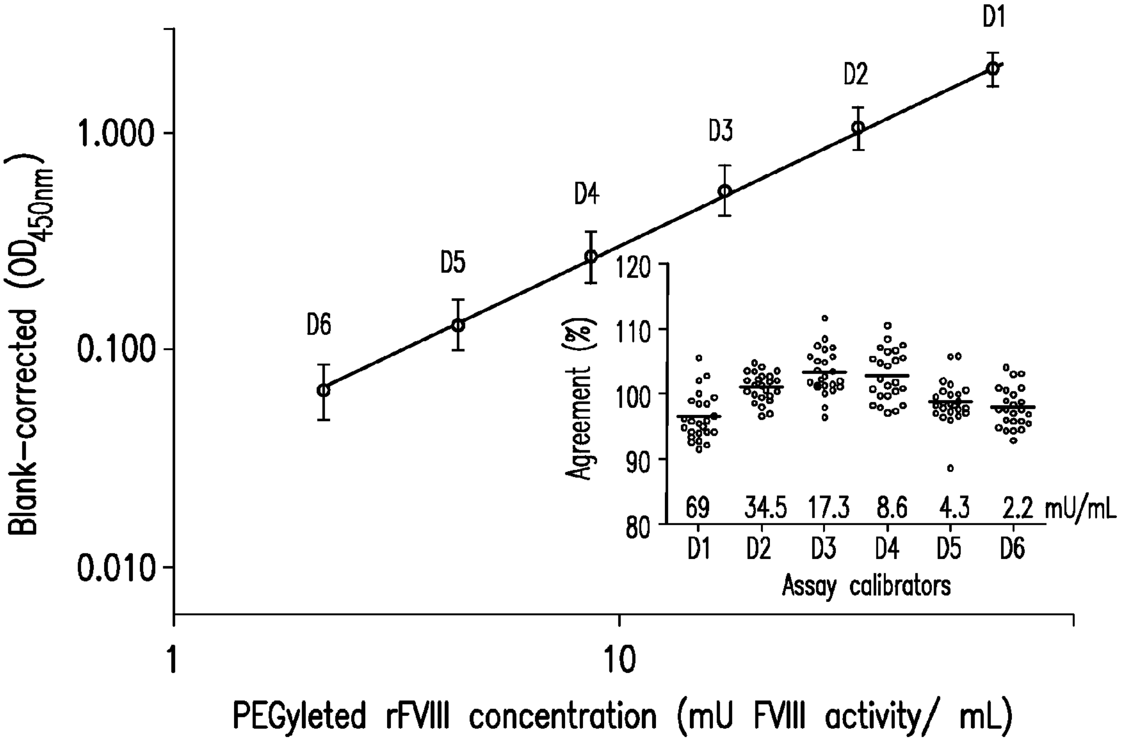
FIG. 3 shows a graph of the mean calibration curve and agreement of back-fitted assay standards demonstrating the accuracy and precision of a MDAA for PEGylated recombinant FVIII. Error bars mark the single standard deviation of the means.

Table 1 gives the means (n=24) of the original data of the calibration curves and their characteristics. In particular, it gives the mean blank-corrected ODs measured for the six calibration curve standards D1 to D6, which had FVIII concentrations ranging from 2.2 mU/mL to 69 mU/mL, and the corresponding blanks. Apart from these direct assay readouts, the calibration curve characteristics slope, y-intercept and correlation coefficient of the resulting calibration curves are shown. Finally, the relative total error (RTE), a combined measure of accuracy and precision of the curve fitting is given. RTE was calculated by back-fitting the ODs measured for each calibration curve standard. The concentrations thus obtained were multiplied with the dilution factor and finally averaged to obtain the mean back-fitted concentration. RTE was then the sum of the absolute difference between the nominal concentration and the mean back-fitted concentration of the assay standard and the double standard deviation of the back-fitted mean concentration, expressed as a percent of the nominal concentration ($RTE=(|x_n-\bar{x}_m|+2\times SD)/\bar{x}_m\times 100$; $\bar{x}_n$ and $\bar{x}_m$ represent the nominal and the measured mean, respectively, and SD the standard deviation of $\bar{x}_m$).

although combining only the pseudo-linear part of dose-response relationship, comprised six individual points. This design makes the calibration curve compliant with the EMA guideline on bioanalytical method validation which requires a minimum number of six calibration points for LBAs independent of the calibration model selected. Although we used a linear evaluation model with a narrow range, our calibration curves nevertheless complied with this request. FIG. 3 shows the mean calibration curve obtained for 24 runs. The insert gives the agreement of the back-fitted assay calibration standards as a percent of the respective nominal concentrations. The current guideline on bioanalytical method validation requires that 75% of the back-fitted concentrations have to be within a ±20% range.

The mean back-fitted concentrations differed by less than 5% for all six calibration curve standards. There was no trend for the relative errors dependent on the FVIII concentration but rather a steady distribution over the whole calibration curve range. Worth mentioning is that the mean RE determined for the standard D6, which has the lowest FVIII concentration of 2.2 mU/mL, did not differ from those determined for the other assay standards. This clearly supports the measurement of samples with PEGylated recombinant FVIII concentrations close to the lower limit of quantification where only one dilution of the sample will yield a signal within the range covered by the calibration curve. The individual REs were within a ±12% range and thus complied with the acceptance criterion of the validation protocol.

TABLE 1

Mean original data and calibration curve characteristics for MDAA of PEGylated FVIII

| Feature | D1 | D2 | D3 | D4 | D5 | D6 | Blank | Slope | Intercept | r | RTE |
|---|---|---|---|---|---|---|---|---|---|---|---|
| Mean | 1.984 | 1.051 | 0.540 | 0.270 | 0.130 | 0.065 | 0.176 | 0.9974 | −1.528 | 0.9994 | 8.3 |
| RSD | 18.3 | 22.9 | 25.0 | 26.5 | 27.1 | 27.8 | 6.6 | 3.7 | −8.3 | n.a. | n.a. |

n.a. stands for not applicable.

The individual direct readouts, i.e. the blank-corrected ODs, showed a certain but acceptable variability between the different assays with RSDs from 18.3% up to 27.8% for the blank-corrected ODs measured for the individual assay calibration standards D1 to D6, whereas the blank showed the low RSD of 6.6%. To compensate for these differences in the direct readout, the calibration curve is constructed on each single plate. Low RSDs determined for the mean slope and the mean y-intercept indicated that the resulting calibration curves were very similar in shape despite the differences in ODs measured for the assay standards and verified this procedure to be efficient in compensating differences between the absolute readouts. Thus, we found RSDs of 3.7% and 8.3% for the mean slope and the mean y-intercept of the calibration curves. Their linearity was adequate as shown by the mean correlation coefficient r=0.9994 with all individual values not lower than 0.9978. Since the correlation coefficient can be a deceptive measure for linearity and accuracy, we also calculated the RTE of the curves. The mean RTE of 8.3% confirmed the high correlation coefficients as an indicator for the accuracy and linearity of the calibration curves. The individual values for the RTE ranged from 2.0% to 17.6%. The fact that only 1 of 24 RTEs was higher than 15% and 16 of 24 RTEs were lower than 10% further illustrated the suitability of the double logarithmic calibration model selected to describe the relation between the signal and FVIII activity. In addition, it should be noted that the calibration curve, Overall, all data confirmed the accuracy, precision and the robustness of constructing the calibration curves for the MDAA for measuring PEGylated recombinant FVIII.

Example 4

Specificity of MDAA for PEGylated FVIII

This example illustrates how to confirm specificity of a MDAA for PEGylated FVIII using a competition assay.

A modification-recognizing antibody was attached to a solid support as described in Example 3.

Samples were selectively bound to a solid support and FVIII activity measured using the chromogenic assay as described in Example 3, except that recombinant PEGylated FVIII samples were diluted to a concentration of 69 mU/mL and then mixed 1+1 with PEG 5000 to achieve final PEG 5000 concentrations ranging from 100 μg/mL to 0.012 μg/mL (14 dilutions).

Figure 4:
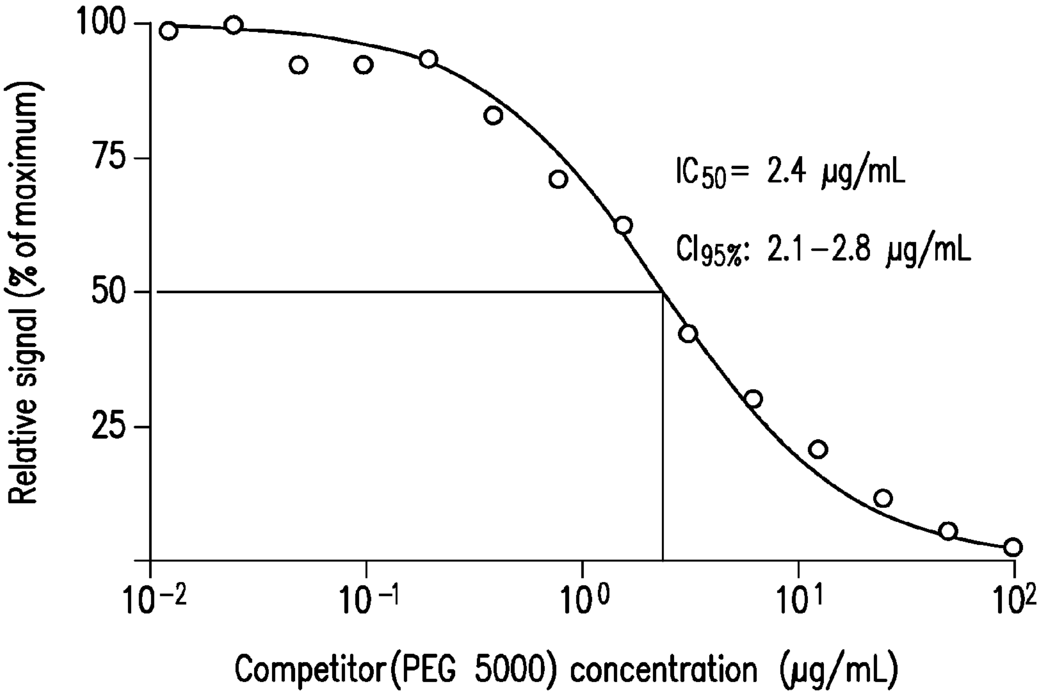
FIG. 4 shows a graph demonstrating the specificity of a MDAA for PEGylated recombinant FVIII using a competition with PEG 5000.

Each competition sample was measured four times in one run. The mean signals obtained were then related back to those obtained from samples containing no competitor to calculated relative signals. FIG. 4 shows the competition curve obtained by this approach and in addition gives the $IC_{50}$, i.e. the PEG 5000 concentration providing half-maximal competition, and the corresponding confidence interval $CI_{95\%}$, calculated for this $IC_{50}$ using GraphPad Prism version 5.00 for Windows, GraphPad Software. The data clearly confirmed the specificity of the capturing step because we determined a clearly dose-dependent reduction of the signal measured in presence of PEG 5000. Half maximal competition was reached under the given assay conditions by a PEG concentration of 2.4 μg/mL.

Example 5

Specificity of MDAA for PEGylated FVIII

This example illustrates specificity of a MDAA for PEGylated FVIII using a competition assay.

A modification-recognizing antibody was attached to a solid support as described in Example 3.

Samples were selectively bound to a solid support and FVIII activity measured using the chromogenic assay as described in Example 3, except that 1) recombinant PEGylated FVIII samples were diluted to a concentration of 40 mU/mL and then mixed 1+1 with rabbit anti-PEG antibodies (PEG-B-47; Epitomics, Inc., Burlingame, Calif.) to achieve final concentrations ranging from 605 μg/mL to 0.00007 μg/mL.

Figure 5:
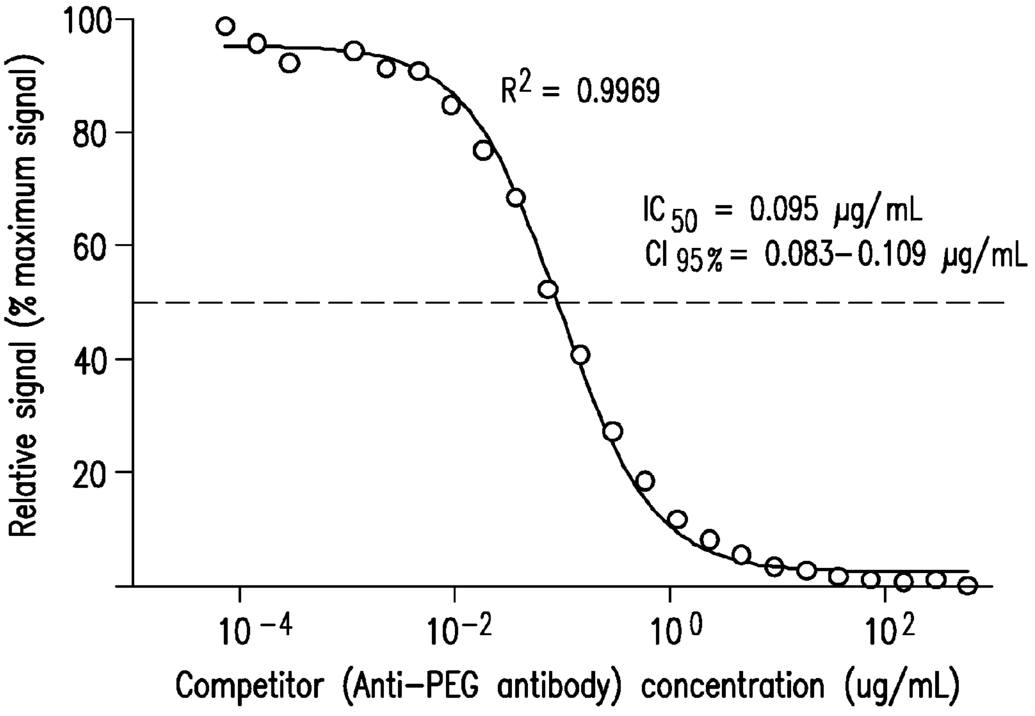
FIG. 5 shows a graph demonstrating the specificity of a MDAA for PEGylated recombinant FVIII using a competition with anti-PEG antibody.

Each competition sample was measured two times in one run. The mean signals obtained were then related back to those obtained from samples containing no competitor to calculated relative signals. FIG. 5 shows the competition curve obtained by this approach and in addition gives the $IC_{50}$, i.e. the antibody concentration providing half-maximal competition, and the corresponding confidence interval $CI_{95\%}$, calculated for this $IC_{50}$ using GraphPad Prism version 5.00 for Windows, GraphPad Software. We found a common competition curve, characterized by the good coefficient of determination $R^2$=0.9969. An anti-PEG concentration of 0.095 μg/mL caused half maximal reduction of the signal under the given assay conditions and confirmed the selectivity of the capturing step.

Example 6

Accuracy and Precision of MDAA for PEGylated FVIII in Plasma

This example illustrates accuracy and precision of a MDAA for PEGylated FVIII in plasma using a spike-recovery assay.

A modification-recognizing antibody was attached to a solid support as described in Example 3.

Samples were selectively bound to a solid support and FVIII activity measured using the chromogenic assay as described in Example 3, except that 1) samples comprised normal human plasma (NHP) was spiked with PEGylated recombinant FVIII a five concentrations ranging from 0.07 to 2 U/mL; or 2) samples comprised eight commercially available FVIII deficient plasma samples and measured before and after being spiked with PEGylated recombinant FVIII at 0.07 U/mL and 0.5 U/mL. The eight FVIII-deficient plasmas were obtained from George King Bio-Medical Inc. (Chelsea, Mass.): GK897-1966 (#1), GK892-2056 (#2), GK896-2031 (#3), Pool-1928 (#4), Pool-1930 (#5), GK893-1964 (#6), GK895-1959 (#7) and GK894-1965 (#8).

Intra-run (n=6) and inter-run precision (n=6) were determined for spiked plasma and buffer samples, while the assay's accuracy was determined by calculating the recovery of the spiked amounts. Finally, the total error was calculated as sum of inter-run precision and accuracy. The current EMA guideline devises that this total error should not exceed 30% or 40% at the assay's lower limit of quantification (LLOQ). Table 2 summarizes the data described above.

TABLE 2

Precision and accuracy of MDAA for PEGylated FVIII

| Nominal | Inter-run precison | | Intra-run precision | | Accuracy | | Total error | |
|---|---|---|---|---|---|---|---|---|
| Concentration | NHP | Buffer | NHP | Buffer | NHP | Buffer | NHP | Buffer |
| 0.07 | 9.3 | 13.2 | n.d. | n.d. | 91.5 | 101.4 | 17.7 | 14.7 |
| 0.25 | 10.0 | 6.5 | n.d. | n.d. | 95.4 | 99.3 | 14.6 | 7.1 |
| 0.5 | 7.2 | 5.6 | 5.1 | 3.7 | 95.0 | 105.8 | 12.2 | 11.4 |
| 1.0 | 8.4 | 6.5 | n.d. | n.d. | 96.9 | 103.2 | 11.6 | 9.7 |
| 2.0 | 7.8 | 7.1 | n.d. | n.d. | 99.6 | 107.2 | 8.2 | 14.2 |

n.d. stands for not done.

High-quality data was obtained by determining the assay's precision and accuracy in normal human plasma and in buffer matrix. Also, the total error of the MDAA for PEGylated recombinant FVIII was clearly lower than 20%, even at the assay's LLOQ of 0.07 U/mL. These data qualified the MDAA for PEGylated recombinant FVIII as an accurate and precise method, suitable for its use as a bioanaytical method.

Figure 6:
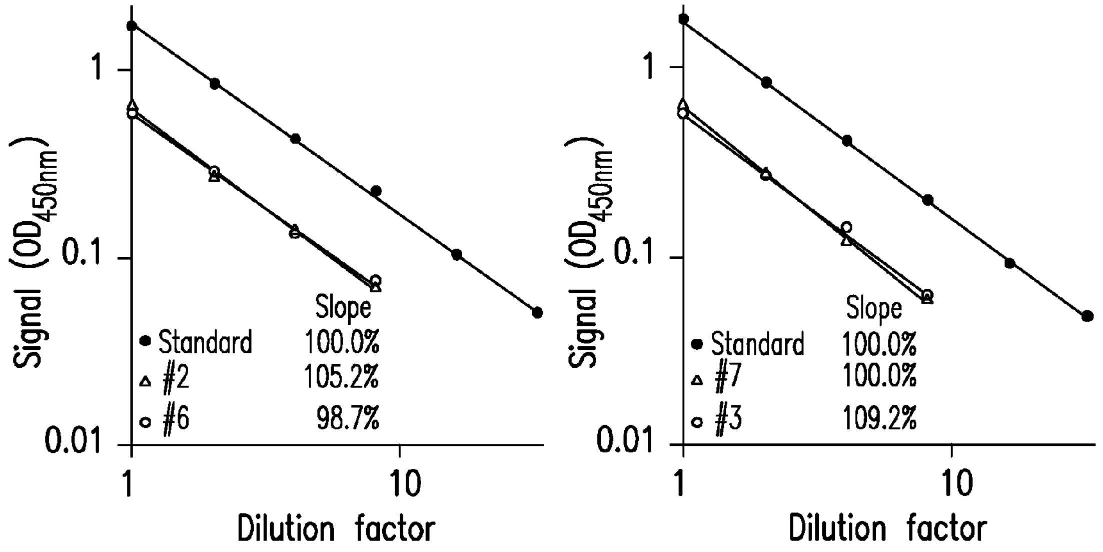
FIG. 6 shows a graph of dilutional linearity demonstrating the accuracy and precision of a MDAA for PEGylated recombinant FVIII.

Table 3 shows the results of the spike-recovery study done in eight FVIII-deficient plasma samples. The recovery of spiked PEGylated recombinant FVIII was also good in the FVIII-deficient plasma samples. Mean recoveries of 91.3% and 98.5% where detected when 0.07 U/mL and 0.5 U/mL PEGylated recombinant FVIII/mL were spiked, respectively. FIG. 6 shows the representative curves for four of the eight FVIII-deficient plasma samples, spiked with 0.5 U/mL. The high parallelism of the spiked samples' curves to those of the assay standard is evident: The slopes obtained for the curves of the spiked samples differed by less than ±10% from those of the assay calibration curves indicating excellent linearity of the dose-response curves obtained for the spiked FVIII-deficient plasma samples.

TABLE 3

Recovery in FVIII-deficient plasma samples

| Lot No. | Item | Spike 1 | Spike 2 |
|---|---|---|---|
| GK897-1966 | #1 | 85.5 | 100.0 |
| GK892-2056 | #2 | 98.6 | 95.9 |
| GK896-2031 | #3 | 89.9 | 93.9 |
| Pool-1928 | #4 | 88.4 | 104.1 |
| Pool-1930 | #5 | 92.8 | 110.2 |
| GK893-1964 | #6 | 87.0 | 93.9 |

TABLE 3-continued

| Recovery in FVIII-deficient plasma samples | | | |
|---|---|---|---|
| Lot No. | Item | Spike 1 | Spike 2 |
| GK895-1959 | #7 | 97.1 | 95.9 |
| GK894-1965 | #8 | 91.3 | 93.9 |

Example 7

MDAA for Polysialylated FVIII in PBS or Human Plasma

This example illustrates that a MDAA for polysialylated FVIII can be conducted in a buffered solution or in the present of blood plasma.

To attach a modification-recognizing antibody to a solid support, 100 μL/well coating antibody solution comprising 1/400 dilution of mouse anti-polysialic acid NCAM antibodies (MAB5324-clone 2-2B; Millipore, Inc.), 0.1 M $NaHCO_3$—Na2CO3, pH 9.5 was incubated in the wells of a F96 Maxisorp plate at 0±10° C. overnight. The plates were then washed with Washing Buffer comprising PBS and 0.05% Tween 20. The wells of the plate were then blocked by incubation 200 μL/well of Dilution Buffer comprising PBS and 10 mg/mL human serum albumin at 37±5° C. for 60±10 minutes. The blocked wells were then washed with Washing Buffer.

To selectively bind a sample to a solid support, 100 μL of the following samples were added to a well 1) a dilution series of 1/40,000 to 1/1,280,000 of polysialylated recombinant FVIII standard prepared using PBS containing 10 mg/mL HSA or 2) a dilution series of 1/20 to 1/320 of human reference plasma prepared using PBS containing 10 mg/mL HSA. Polysialylated recombinant FVIII was prepared by linking a 20 kDa polysialic acid reagent containing an active aminooxy group to the oxidized N-glycans of FVIII, see U.S. Publication Nos. 20110027350 and 20110028693, each of which is hereby incorporated by reference in its entirety. The preparation had a FVIII:C activity of 3110 IU FVIII/mL, measured with a chromogenic method, and contained 483 μg/mL N-acetylneuraminic acid resulting in a degree of polysialylation of about 7-8. The samples were loaded to the plate and incubated at about 18° C. to about 26° C. for 60±10 minutes. Under these conditions, Polysialylated recombinant FVIII selectively bound to the solid support by means of its polysialic acid (PSA) moiety using an anti-PSA antibody. The plate was then washed 6 times with Washing Buffer followed by incubation with 200 μL/well of a FVIII dilution buffer comprising 3.4 g/L imidazole, 5.85 g/L NaCl; 10 mg/mL HSA, pH 7.4. This equilibration was done at room temperature for 3 minutes. After a washing step with Washing Buffer, the wells were emptied and FVIII activity was measured with a chromogenic assay following the standard chromogenic procedure using the Immunochrom FVIII kit (Technoclone, GmbH, Vienna, Austria). The wells were filled with 20 μL FVIII dilution buffer followed by the sequential addition of 20 μL reagent A and reagent B. The plate was then incubated at 37±5° C. for 5 minutes. Then pre-warmed substrate solution was added (100 μL/well) and incubated at 37±5° C. for 15 minutes. Finally, the reaction was stopped by adding 20% acetic acid (40 μL/well). Subsequently, the plate was measured at 405 nm (reference wavelength 620 nm) with an ELISA reader.

Figure 7:
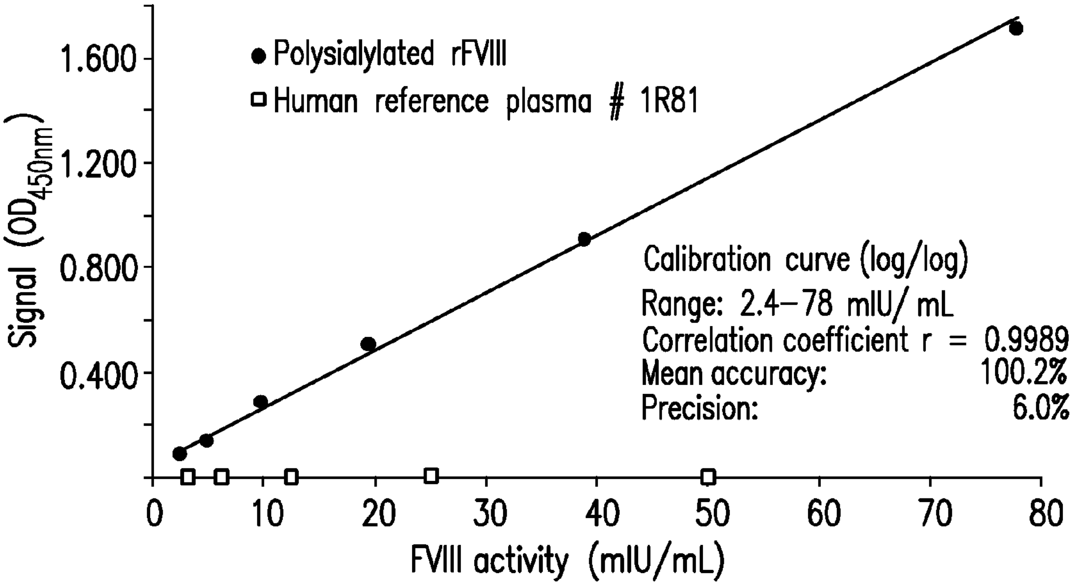
FIG. 7 shows a graph of the concentration-response curve of a MDAA for polysialylated recombinant FVIII using polysialylated FVIII preparation in a FVIII activity range from 78 to 2.4 mIU/mL and the missing response of human plasma containing non-modified FVIII.

FIG. 7 shows the concentration-response curve obtained for the polysialylated FVIII preparation in a FVIII activity range from 2.4 to 78 mIU/mL. The concentration-response curve for polysialylated FVIII showed a good linearity through the entire FVIII concentration range after logarithmic transformation. This was shown by the correlation coefficient r=0.9989 and supported by the back-fitted concentrations calculated for the individual points of the calibration curve, which differed by less than 12% (range: 89.8% to 108.5%; mean 100.2%) from the nominal ones over the whole range. The data furthermore confirmed the specificity of the MDAA because human plasma, containing non-modified FVIII, showed absolutely no response when measured at similar FVIII concentrations as done for the polysialylated FVIII.

The influence of human plasma on the MDAA was further investigated by measuring the response for polysialylated FVIII diluted in human plasma, which was pre-diluted 1/200. Table 4 directly compares the mean blank-corrected optical densities (ODs) measured for polysialylated FVIII diluted in buffer and in human plasma. It also gives the back-fitted FVIII concentrations for the two dilution series in buffer and human plasma, respectively, and the agreement with the nominal FVIII concentrations, given as a percent of the nominal concentrations.

TABLE 4

MDAA for polysialylated FVIII in buffer and in human plasma

| | | Polysialylated FVIII in Buffer | | | Polysialylated FVIII in Plasma | | |
|---|---|---|---|---|---|---|---|
| Dilution | mU/mL | OD | Backfitted (mIU/mL) | % nominal | OD | Read-off (mIU/mL) | % nominal |
| 40,000 | 77.7 | 1.715 | 79.8 | 102.6 | 1.786 | 83.6 | 107.6 |
| 80,000 | 38.9 | 0.911 | 38.1 | 98.1 | 1.016 | 43.3 | 111.4 |
| 160,000 | 19.4 | 0.510 | 19.4 | 99.7 | 0.532 | 20.3 | 104.7 |
| 320,000 | 9.7 | 0.290 | 10.0 | 103.2 | 0.274 | 9.4 | 96.6 |
| 640,000 | 4.9 | 0.142 | 4.4 | 89.8 | 0.157 | 4.9 | 100.9 |
| 1,280,000 | 2.4 | 0.092 | 2.6 | 107.5 | 0.089 | 2.5 | 104.1 |
| Slope | | | 0.8571 | | | 0.8762 | |
| % slope | | | 100.0 | | | 102.2 | |

The concentration-response curves obtained for the polysialylated FVIII preparation were very similar in buffer and in human plasma as shown by their slopes which differed by less than 3%. The recovery of polysialylated FVIII activity in human plasma was as good as in buffer. The mean recovery was 104.2% with individual values between 96.6 and 111.4% for the polysialylated preparation diluted in human plasma and 100.2% for the same preparation diluted in buffer. These data demonstrated that the modification-dependent activity assay for polysialylated FVIII performed adequately in human plasma, when diluted 1/200. Non-polysialylated FVIII, contained in plasma, did not contribute to the signal demonstrating the absolute specificity of the MDAA for polysialylated FVIII as expected.

Example 8

MDAA for Polysialylated FVIII in Plasma from Different Animal Species

This example illustrates that a MDAA for polysialylated FVIII can be conducted in the present of blood plasma.

A modification-recognizing antibody was attached to a solid support as described in Example 7.

Samples were selectively bound to a solid support and FVIII activity measured using the chromogenic assay as described in Example 7, except that 1) recombinant polysialylated FVIII was prepared by diluting 1/20,000 with PBS containing 10 mg/mL HSA and 50 mM benzamidine, then further 1+1 with the 1/5 pre-diluted plasma samples of different species and finally 1+1 directly on the plate (the final concentration of plasma corresponded to a dilution of 1/20); and 2) preparations were diluted with plasma from the following species: Rat, mouse, FVIII-deficient mouse, cynomolgus monkey and human reference plasma.

Figure 8:
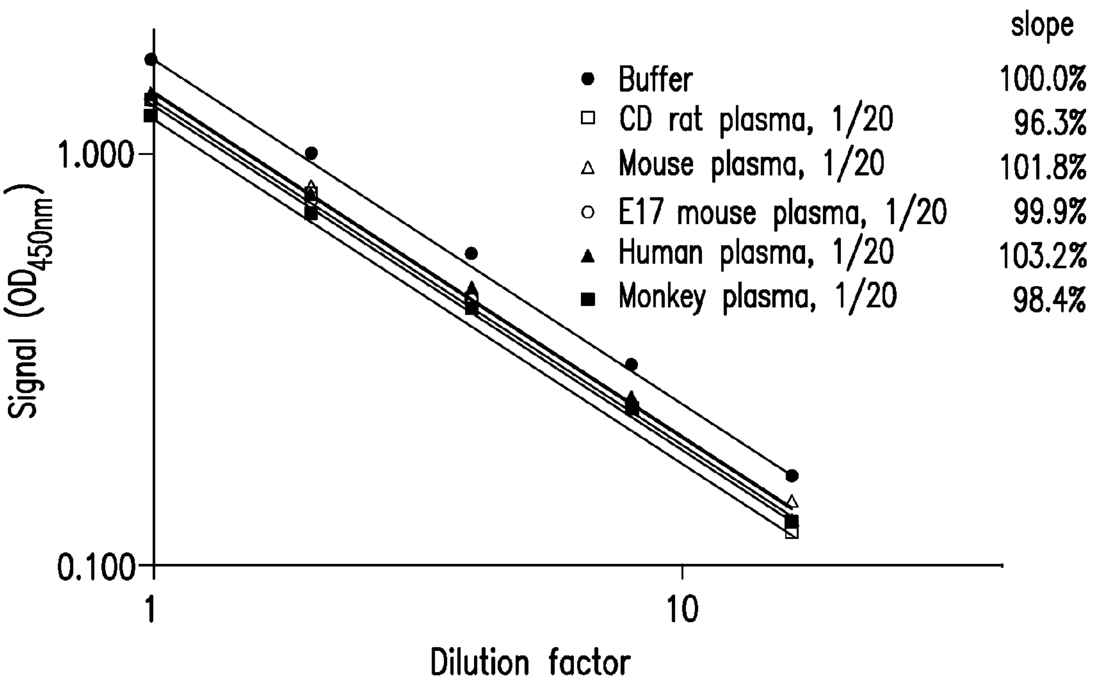
FIG. 8 shows a graph of the concentration-response curves of a MDAA for polysialylated recombinant FVIII using polysialylated recombinant FVIII spiked to plasma from different animal species relative to that determined in buffer.

FIG. 8 shows the concentration-response curves obtained for the polysialylated FVIII in the different plasma matrices and gives their slopes relative to that determined in buffer. Linear concentration-response curves were obtained for the plasma samples investigated. In addition, these curves were very parallel to that obtained in buffer and their slopes differed only marginally, i.e. less than 4% from that determined in buffer. These data therefore demonstrated that plasma from the different species investigated did not interfere with the MDAA for polysialylated FVIII when diluted 1/20. Furthermore, these data support preparation of the MDAA calibration curve in dilution buffer and use of this dilution series for measuring plasma samples.

Example 9

Performance and Sensitivity of MDAA for Polysialylated FVIII

This example illustrates performance and sensitivity of a MDAA for polysialylated FVIII using a spike-recovery assay.

A modification-recognizing antibody was attached to a solid support as described in Example 7.

Samples were selectively bound to a solid support and FVIII activity measured using the chromogenic assay as described in Example 7, except that lyophilized polysialylated recombinant FVIII was dissolved to yield a solution with 250 IU/mL and diluted with Dilution buffer comprising PBS, 0.05% Tween 20, 10 mg/mL HSA, and 50 mM benzamidine to nominal FVIII concentrations of 10, 5, 2.5, 1 and 0.5 IU/mL, then further 1/10 with rat plasma followed by a 1/10 dilution with buffer. These samples were then further diluted 1+1 directly on the plate yielding a final rat plasma concentration corresponded to a dilution of 1/20. In addition, FVIII activity was measured in the chromogenic assay using an incubation time of 15 minutes for the substrate reagents and an incubation time of 45 minutes for the substrate solution.

Figure 9:
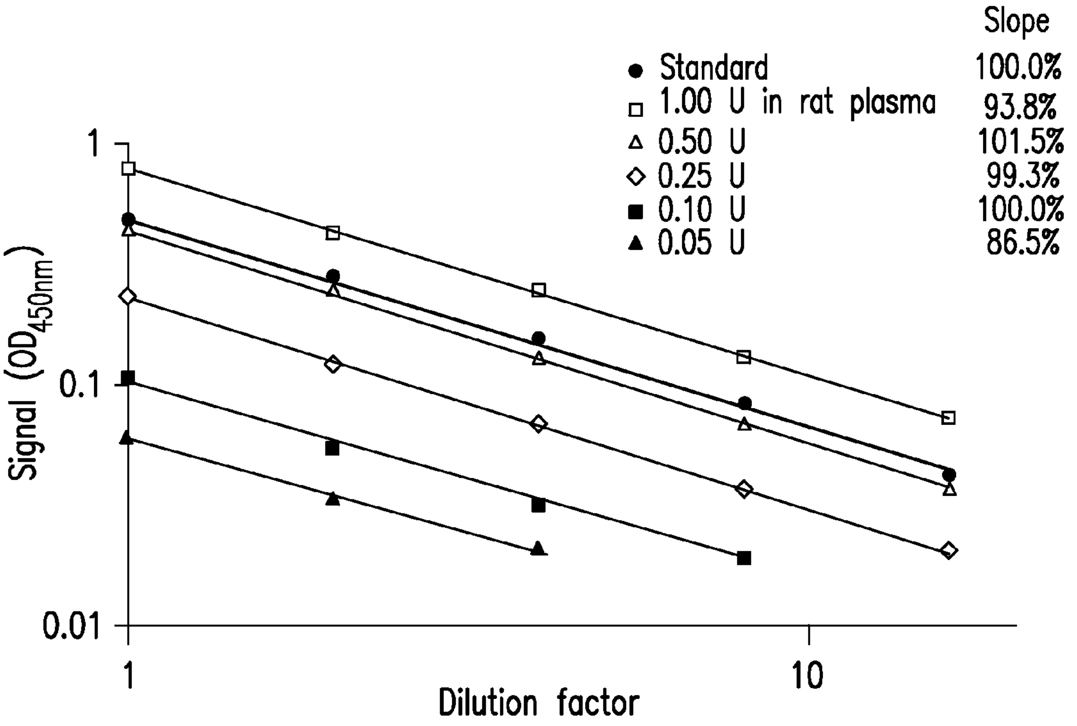
FIG. 9 shows a graph of the concentration-response curves demonstrating the performance and sensitivity of a MDAA for polysialylated recombinant FVIII.

FIG. 9 shows the concentration-response curves for these samples containing polysialylated FVIII concentrations ranging from 1 to 0.05 IU/mL. The concentration-response curves of the spiked rat plasma samples were linear and parallel to that obtained for the assay standard diluted in buffer when they contained more than three data points. In such cases, the slopes differed by less than 7% from that of the dilutions series determined for the sample containing buffer only. Even the sample spiked with 0.05 IU/mL polysialylated FVIII showed a linear concentration-response curve. Its slope differed only by 13.5% from that of the buffer sample demonstrating that the MDAA performed adequately in rat plasma also at very low concentrations of polysialylated FVIII, close to the presumably limit of quantification. The recoveries of spiked polysialylated FVIII were within a 100±20% range of the nominal concentrations. These data demonstrated that the MDAA for polysialylated FVIII performed acceptably in rat plasma samples at a minimal dilution of 1/20.

Example 10

Accuracy and Precision of MDAA for Polysialylated FVIII

This example illustrates accuracy and precision of a MDAA for polysialylated FVIII.

A modification-recognizing antibody was attached to a solid support as described in Example 7.

Samples were selectively bound to a solid support and FVIII activity measured using the chromogenic assay as described in Example 9.

Table 5 gives the original data and calibration curve characteristics, which were obtained for 16 calibration curves, constructed on different days. Blank-corrected optical densities (ODs) of the calibrators D1 to D5, covering the polysialylated FVIII activity range from 1.6 to 25 mIU/mL, blank, slope, y-intercept, correlation coefficient r and relative total error (RTE). RTE was calculated according to $RTE=(|\bar{x}_N-\bar{x}_M|+2SD)/\bar{x}M\times100$. $\bar{x}N$ and $\bar{x}M$ represent the nominal and the measured mean, respectively, and SD the standard deviation of $\bar{x}M$. In order to obtain the mean $\bar{x}M$, the mean ODs of the individual dilutions were back-fitted on the curve, normalized by multiplication with the respective dilution and finally averaged.

TABLE 5

Precision of the calibration curve

| Test No. | D1 | D2 | D3 | D4 | D5 | Blank | Slope | Intercept | r | RTE |
|---|---|---|---|---|---|---|---|---|---|---|
| AE-0501 | 0.488 | 0.256 | 0.135 | 0.067 | 0.029 | 0.137 | 1.0076 | −1.699 | 0.9983 | 12.8 |
| AE-0502 | 0.391 | 0.210 | 0.104 | 0.047 | 0.025 | 0.132 | 1.0145 | −1.809 | 0.9993 | 8.5 |
| AE-0503 | 0.386 | 0.212 | 0.110 | 0.048 | 0.024 | 0.129 | 1.0227 | −1.814 | 0.9983 | 13.0 |
| AE-0504 | 0.424 | 0.233 | 0.131 | 0.066 | 0.032 | 0.129 | 0.9272 | −1.651 | 0.9988 | 10.9 |
| AE-0491 | 0.480 | 0.270 | 0.146 | 0.074 | 0.039 | 0.139 | 0.9117 | −1.579 | 0.9995 | 6.7 |
| AE-0492 | 0.413 | 0.233 | 0.131 | 0.067 | 0.041 | 0.134 | 0.8460 | −1.566 | 0.9992 | 8.7 |
| AE-0493 | 0.448 | 0.228 | 0.127 | 0.064 | 0.034 | 0.134 | 0.9324 | −1.654 | 0.9998 | 4.7 |
| AE-0494 | 0.456 | 0.247 | 0.127 | 0.063 | 0.033 | 0.142 | 0.9604 | −1.672 | 0.9998 | 4.9 |
| AE-0521 | 0.403 | 0.221 | 0.125 | 0.069 | 0.036 | 0.142 | 0.8652 | −1.602 | 0.9998 | 4.4 |
| AE-0522 | 0.400 | 0.207 | 0.116 | 0.060 | 0.031 | 0.141 | 0.9221 | −1.686 | 0.9997 | 5.4 |
| AE-0523 | 0.427 | 0.237 | 0.129 | 0.062 | 0.038 | 0.140 | 0.8950 | −1.616 | 0.9988 | 10.6 |
| AE-0524 | 0.438 | 0.247 | 0.136 | 0.074 | 0.039 | 0.141 | 0.8727 | −1.570 | 0.9998 | 4.1 |
| AE-0531 | 0.488 | 0.283 | 0.161 | 0.087 | 0.049 | 0.143 | 0.8361 | −1.471 | 0.9998 | 4.6 |
| AE-0532 | 0.383 | 0.215 | 0.119 | 0.062 | 0.038 | 0.142 | 0.8468 | −1.602 | 0.9991 | 9.1 |
| AE-0533 | 0.454 | 0.252 | 0.138 | 0.071 | 0.039 | 0.144 | 0.8954 | −1.586 | 0.9997 | 5.0 |
| AE-0534 | 0.452 | 0.249 | 0.143 | 0.077 | 0.043 | 0.142 | 0.8521 | −1.535 | 0.9999 | 3.2 |

TABLE 5-continued

| Precision of the calibration curve | | | | | | | | | | |
|---|---|---|---|---|---|---|---|---|---|---|
| Test No. | D1 | D2 | D3 | D4 | D5 | Blank | Slope | Intercept | r | RTE |
| Mean | 0.433 | 0.237 | 0.130 | 0.066 | 0.035 | 0.138 | 0.9130 | −1.632 | 0.9994 | 7.3 |
| RSD | 8.2 | 9.3 | 10.8 | 15.2 | 18.6 | 3.6 | 6.8 | −5.6 | n.a. | n.a. |

n.a. stands for not applicable.

The mean ODs of the five calibrators showed acceptable RSDs that were inversely proportional to their concentrations but still not higher than 20% also for the lowest FVIII concentration. The calibration curves had mean RSDs of 6.8% and 5.6% for slope and y-intercept, respectively. In addition, their linearity was acceptably good with correlation coefficients higher than 0.9983 and RTEs lower than 13.0%.

Figure 10:
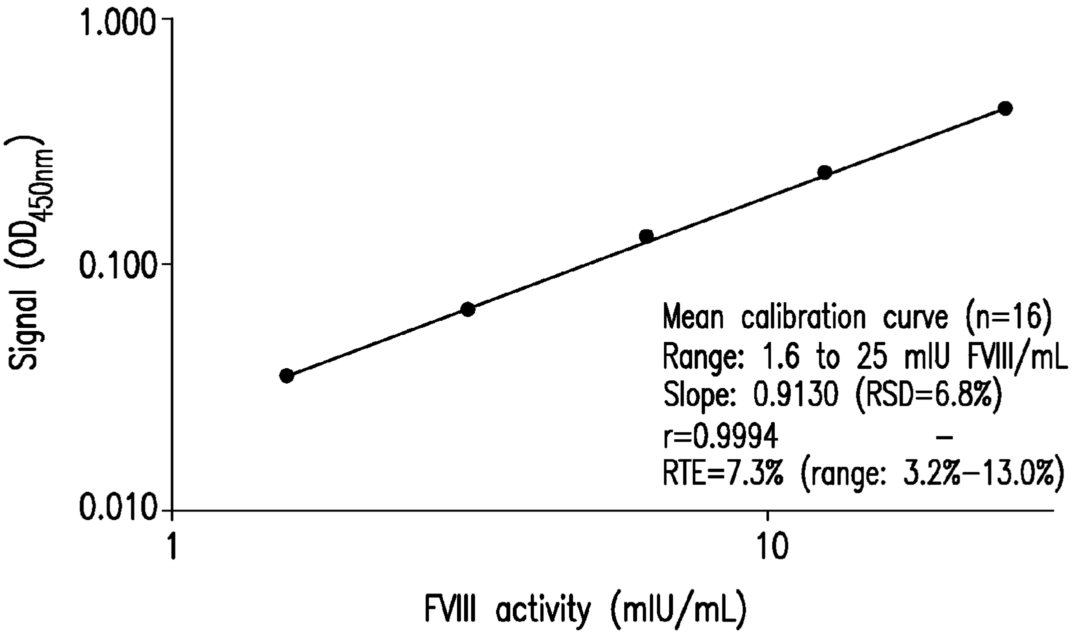
FIG. 10 shows a graph of the mean calibration curve demonstrating the accuracy and precision of a MDAA for polysialylated recombinant FVIII.
Figure 11:
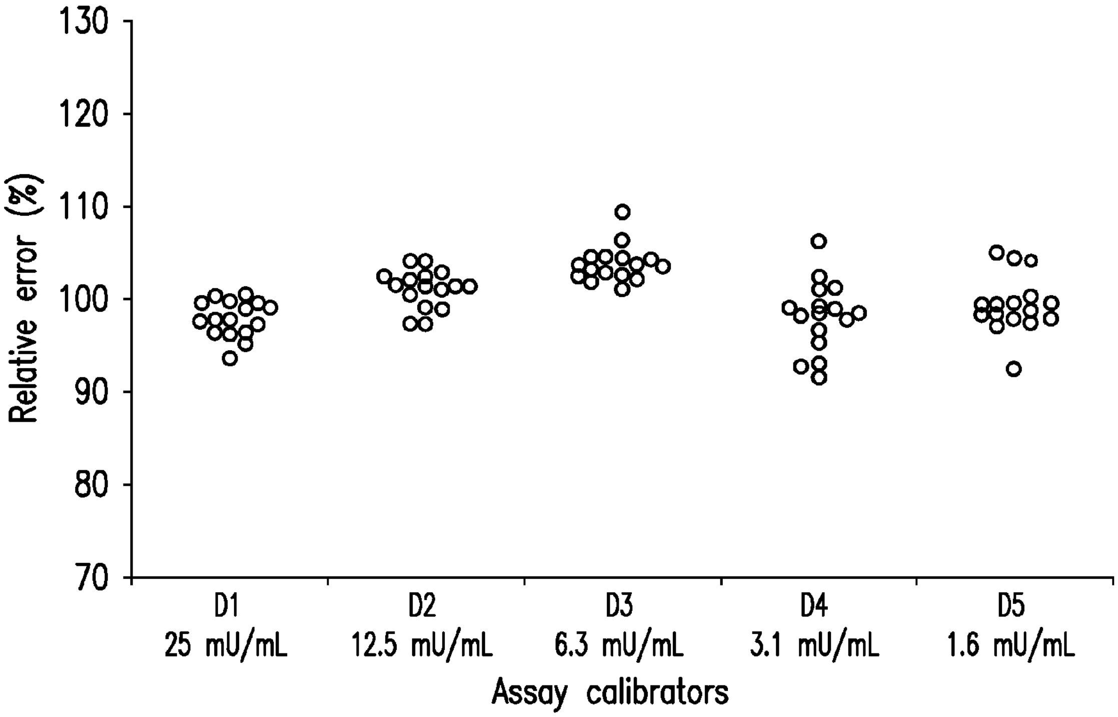
FIG. 11 shows a graph of the agreement of the back-fitted concentrations with the nominal ones for the five calibrators of the individual curves illustrating that back-fitted concentrations were within a ±10% range of the nominal ones over the whole range.

FIG. 10 shows the mean calibration curve. The data demonstrated the assay's robustness and showed that the calibration curve could be constructed with acceptable repeatability. The accuracy of these curves was further checked by back-fitting the ODs measured and calculating the agreement with the nominal values. FIG. 11 shows these data for the five calibrators of the individual curves illustrating that the back-fitted concentrations were within a ±10% range of the nominal ones over the whole range.

Example 11

Detection of Polysialylated FVIII from a Blood Sample Using MDAA

This example illustrated in vivo detection of a blood protein using a MDAA.

Polysialylated recombinant FVIII was prepared as described in Example 7. The preparation had a FVIII:C activity of 3110 IU FVIII/mL, measured with a chromogenic method, and contained 483 μg/mL N-acetylneuraminic acid resulting in a degree of polysialylation of about 7-8. The Polysialylated recombinant FVIII was administered to CD rats and FVIII activity was monitored with the MDAA for polysialylated FVIII in citrated rat plasma samples taken before and 0.08 hours, 0.5 hours, 2 hours, 6 hours, 12 hours, 24 hours, 36 hours, and 48 h after administration.

A modification-recognizing antibody was attached to a solid support as described in Example 7.

Samples were selectively bound to a solid support and FVIII activity measured using the chromogenic assay as described in Example 7.

Figure 12:
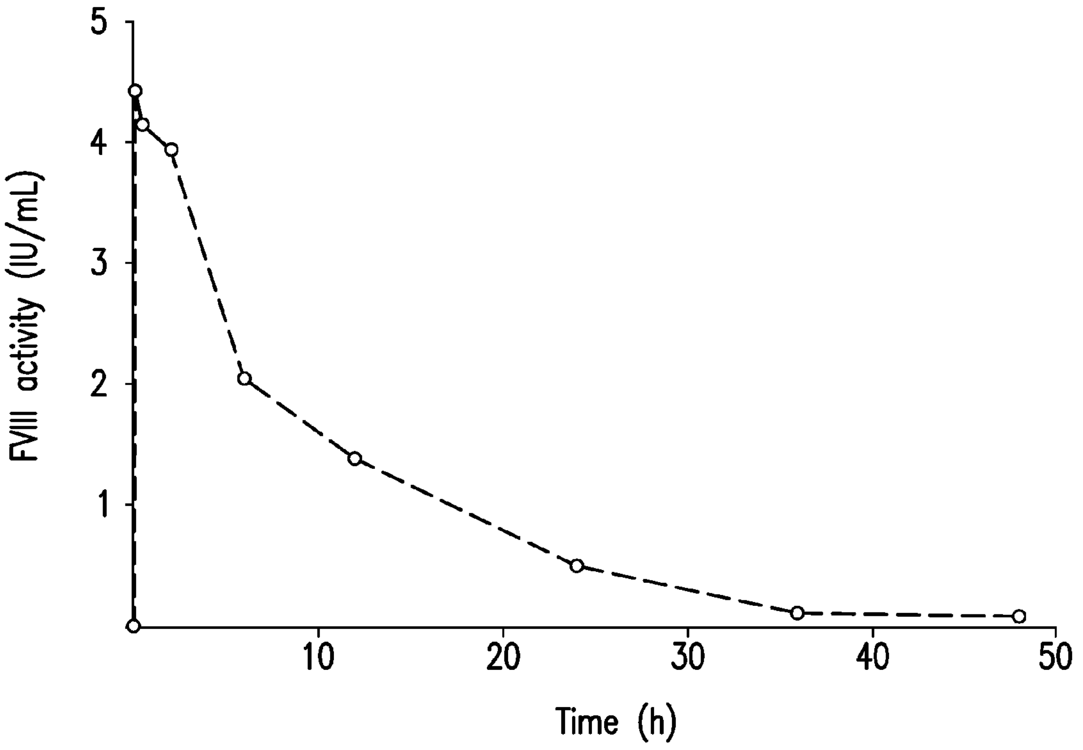
FIG. 12 shows a graph of the pharmacokinetic profile obtained with a MDAA for polysialylated recombinant FVIII administered to rats containing normal levels of endogenous FVIII.

FIG. 12 shows the pharmacokinetic profile obtained. The data demonstrated that the MDAA for polysialylated FVIII was suitable for determining the pharmacokinetic profile of polysialylated FVIII in an animal model containing endogenous FVIII. There was no interference from the endogenous, non-modified rat FVIII and polysialylated FVIII could be measured at very high sensitivity.

Example 12

Accuracy and Precision of MDAA for Polysialylated FVIII

This example illustrates accuracy and precision of a MDAA for polysialylated FVIII.

To attach a modification-recognizing antibody to a solid support, 100 μL/well coating antibody solution comprising 1/1,000 dilution of mouse anti-polysialic acid NCAM antibodies (MAB5324-clone 2-2B; Millipore, Inc.), 0.1 M $NaHCO_3$—Na2CO3, pH 9.5 was incubated in the wells of a F96 Maxisorp plate at 0±10° C. overnight. The plates were then washed with Washing Buffer comprising PBS and 0.05% Tween 20. The wells of the plate were then blocked by incubation 200 μL/well of Dilution Buffer comprising PBS and 10 mg/mL human serum albumin at 37±5° C. for 60±10 minutes. The blocked wells were then washed with Washing Buffer.

To selectively bind a sample to a solid support, 100 μL of the following samples were added to a well 1) a dilution series of six samples including a polysialylated recombinant FVIII standard prepared using 1/10 human plasma solution diluted with PBS, 3% skimmed milk and 50 mM benzamidine and covering a FVIII concentration range from 1.1 mU/mL to 34.2 mU/mL (representing dilution factors of 1/6,000 to 1/192,000); 2) a dilution series of human plasma prepared using 1/10 human plasma solution diluted with PBS, 3% skimmed milk and 50 mM benzamidine; or 3) a dilution series of a test control prepared using 1/10 human plasma solution diluted with PBS, 3% skimmed milk and 50 mM benzamidine Polysialylated recombinant FVIII was prepared by linking a 20 kDa polysialic acid reagent containing an active aminooxy group to the oxidized N-glycans of FVIII, see U.S. Publication Nos. 20110027350 and 20110028693, each of which is hereby incorporated by reference in its entirety. The preparation had a FVIII:C activity of 3110 IU FVIII/mL, measured with a chromogenic method, and contained 483 μg/mL N-acetylneuraminic acid resulting in a degree of polysialylation of about 7-8. The samples were loaded to the plate and incubated at about 18° C. to about 26° C. for 120±10 minutes. Under these conditions, polysialylated recombinant FVIII selectively bound to the solid support by means of its polysialic acid (PSA) moiety using an anti-PSA antibody. The plate was then washed 6 times with Washing Buffer followed by incubation with 200 μL/well of a FVIII dilution buffer comprising 3.4 g/L imidazole, 5.85 g/L NaCl; 10 mg/mL HSA, pH 7.4. This equilibration was done at about 18° C. to about 26° C. for 5-10 minutes.

After a washing step with Washing Buffer, the wells were emptied and FVIII activity was measured with a chromogenic assay following the standard chromogenic procedure using the Immunochrom FVIII kit (Technoclone, GmbH, Vienna, Austria). The wells were filled with 20 μL FVIII dilution buffer followed by the sequential addition of 20 μL reagent A and reagent B. The plate was placed on a mixing device set at 500 rpm and incubated at about 18° C. to about 26° C. for 15 minutes. Then 100 μL/well of substrate solution was added and incubated at about 18° C. to about 26° C. for 45 minutes. Finally, the reaction was stopped by adding 40 μL/well of 20% acetic acid. The optical densities (ODs) are measured in an ELISA reader at 405 nm (reference wavelength 620 nm). The quantitative evaluation is based on a double-logarithmic calibration curve. Blank-corrected mean ODs of the individual calibration curve standards will be correlated with their FVIII concentrations. The resulting calibration curve is used to calculate the samples' FVIII concentrations when their ODs are within the OD range covered by the calibration curve. Three different analysts participated in this study in order to check for an operator-dependent influence.

Table 6 shows the means (n=112) of the original data of the calibration curves and their characteristics. In particular, it gives the mean blank-corrected ODs measured for the six calibration curve standards D1 to D6, which had FVIII concentrations ranging from 34.2 to 1.1 mU/mL, and the corresponding blanks. Apart from these direct assay readouts, the calibration curve characteristics slope, y-intercept and correlation coefficient of the resulting calibration curves are shown. Finally, the relative total error (RTE), a combined measure of accuracy and precision of the curve fitting is given. RTE was calculated by back-fitting the ODs measured for each calibration curve standard. The concentrations thus obtained were multiplied with the dilution factor and finally averaged to obtain the mean back-fitted concentration. RTE was then the sum of the absolute difference between the nominal concentration and the mean back-fitted concentration of the assay standard and the double standard deviation of the back-fitted mean concentration, expressed as a percent of the nominal concentration ($RTE=(|\bar{x}_n-\bar{x}_m|+2\times SD)/\bar{x}_m\times 100$; $\bar{x}_n$ and $\bar{x}_m$ represent the nominal and the measured mean, respectively, and SD the standard deviation of $\bar{x}_m$).

TABLE 6

Mean calibration curve of MDAA for polysialylated recombinant FVIII (n = 112)

| Feature | D1 | D2 | D3 | D4 | D5 | D6 | Blank | Slope | Intercept | r | RTE |
|---|---|---|---|---|---|---|---|---|---|---|---|
| Mean | 1.348 | 0.758 | 0.400 | 0.203 | 0.097 | 0.049 | 0.127 | 0.9659 | −1.329 | 0.9990 | 11.2 |
| RSD | 16.3 | 18.0 | 18.3 | 18.6 | 20.0 | 18.9 | 14.7 | 2.6 | −6.7 | n.a. | n.a. |

n.a. stands for not applicable.

The direct readouts of the MDAA, the blank corrected ODs of the calibration curve standards, showed an acceptable variability, which was not higher than 20%, expressed as the RSD of the mean of 112 calibration curves. The RSDs measured for the individual calibration curve standards varied only marginally, ranging from 16.3% to 20.0%. Also the RSD determined for the assay blank (14.7%) differed not obviously from these RSDs. These data point to slight changes in the room temperature as being responsible for the alterations in the direct readouts because the whole procedure of the assay is done at room temperature. These slight alterations, however, are not expected to negatively influence the assay performance as shown by the following data. These data resulted in highly similar calibration curves: Their mean slope and y-intercept had RSDs from 2.6% and 6.7%, respectively, illustrating the parallelism of these curves constructed on different days by different operators. Furthermore, these curves were linear as demonstrated by their correlation coefficients that ranged from 0.9972 to 1.0000 with an average correlation coefficient of r=0.9990. Since the correlation coefficient can be a deceptive indicator of the accuracy of the calibration curve, we also calculated the RTE as a measure, which more adequately describes the performance of the calibration curve. Thus, we determined a mean RTE of 11.2% with individual values ranging from 2.4% to 19.7%. A closer examination showed that only 12 of 112 RTEs were higher than 15%, while 41 RTEs were lower than 10%. As a further testing for the quality of fit and to confirm the calibration model selected, we also calculated the agreement of the back-fitted assay calibration curve standards with their nominal concentrations. Table 7 gives the mean results obtained and the range.

TABLE 7

Agreement of back-fitted concentrations for calibration curves of MDAA for polysialylated recombinant FVIII

| Feature | D1 | D2 | D3 | D4 | D5 | D6 |
|---|---|---|---|---|---|---|
| Mean | 93.4 | 102.8 | 105.9 | 104.6 | 97.2 | 96.9 |
| RSD | 2.1 | 2.0 | 2.1 | 2.8 | 3.2 | 3.1 |
| Min | 88.8 | 98.1 | 100.6 | 97.2 | 86.7 | 90.1 |
| Max | 99.4 | 107.8 | 111.8 | 112.5 | 104.2 | 106.1 |

Figure 13:
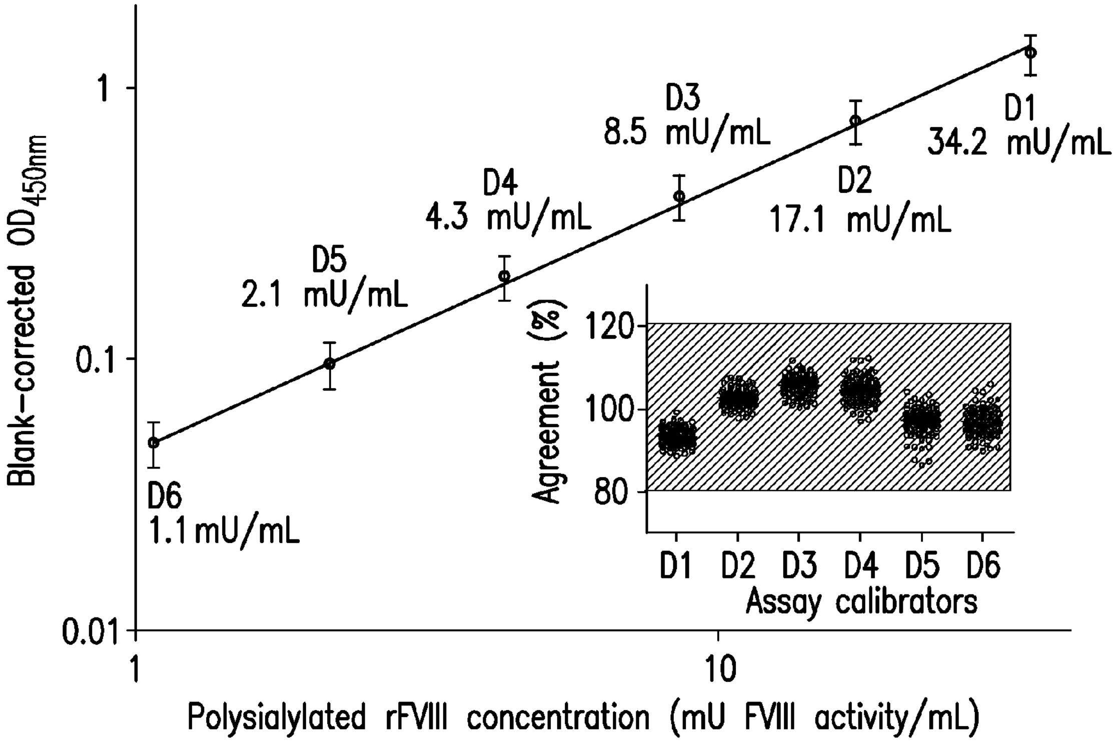
FIG. 13 shows a graph of the mean calibration curve demonstrating the accuracy and precision of a MDAA for polysialylated recombinant FVIII. Error bar gives the single standard deviation of the means.

The mean back-fitted concentrations of the assay calibration standards agreed well with the respective nominal concentrations. The assay standard D1 with the highest polysialylated recombinant FVIII concentration showed the highest deviation from the nominal concentration, whereas the lowest assay standard D6 differed less than the assay standards D3 and D4. This demonstrated that also samples with low polysialylated recombinant FVIII concentrations can be accurately extrapolated. All individual back-fitted concentrations, however, were within a range, which complies with current regulations requiring a ±20% agreement for at least 70% of the assay calibration standards after back-fitting. FIG. 13 shows the mean calibration curve obtained for 24 runs. The insert gives the agreement of the back-fitted assay calibration standards as a percent of the respective nominal concentrations.

Overall, all data confirmed the accuracy, precision and the robustness of constructing the calibration curves for the MDAA for measuring polysialylated FVIII.

Example 13

Specificity of MDAA for Polysialylated FVIII

This example illustrates specificity of a MDAA for polysialylated FVIII using a competition assay.

A modification-recognizing antibody was attached to a solid support as described in Example 12.

Samples were selectively bound to a solid support and FVIII activity measured using the chromogenic assay as described in Example 12, except that 1) recombinant PEGylated FVIII samples were diluted to a concentration of 68.4 mU/mL and then mixed 1+1 with 20 kDa polysialic acid (Lipoxen, UK) to achieve final concentrations ranging from 0.06 μg/mL to 1,000 μg/mL.

Figure 14:
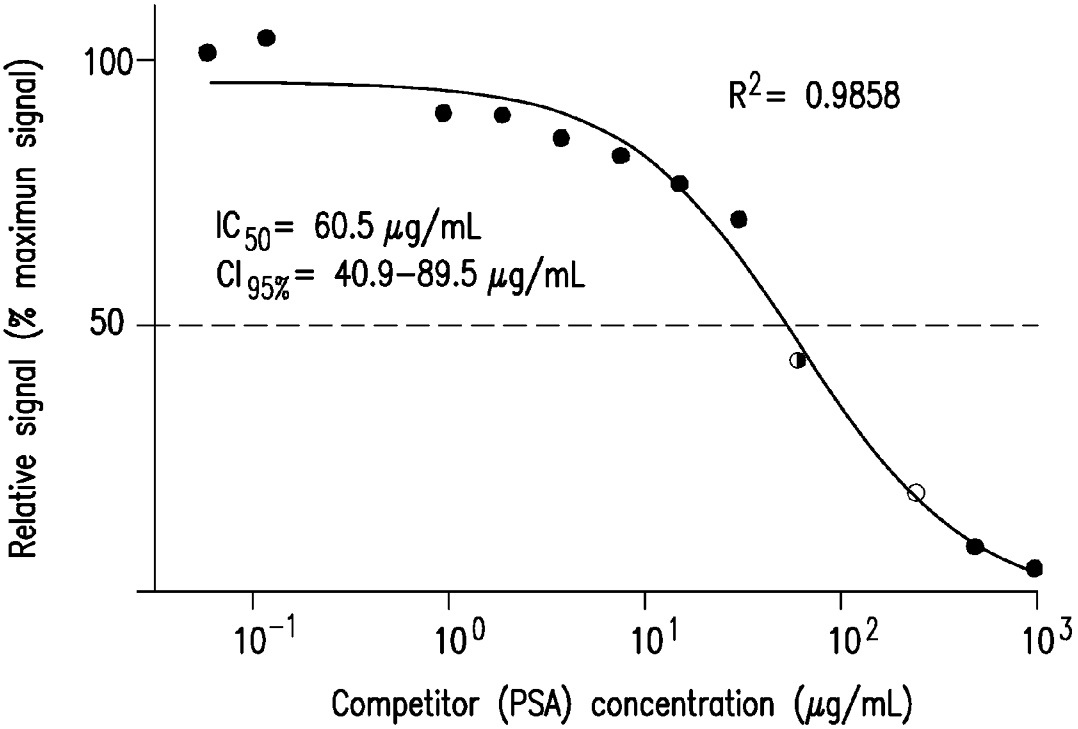
FIG. 14 shows a graph demonstrating the specificity of a MDAA for polysialylated recombinant FVIII using a competition with polysialic acid.

Each competition sample was measured two times in one run. The mean signals obtained were then related back to those obtained from samples containing no competitor to calculated relative signals. FIG. 14 shows the competition curve obtained by this approach and in addition gives the $IC_{50}$, i.e. the polysialic acid concentration providing half-maximal competition, and the corresponding confidence interval $CI_{95\%}$, calculated for this $IC_{50}$ using GraphPad Prism version 5.00 for Windows, GraphPad Software. The data obtained obviously confirmed the specificity of the capturing step because we determined a clearly dose-dependent reduction of the signal measured in the presence of polysialic acid. A half maximal competition was reached under the given assay conditions by a polysialic acid concentration of 60.5 μg/mL.

Example 14

Precision of MDAA for Polysialylated FVIII

This example illustrates precision of a MDAA for polysialylated FVIII.

A modification-recognizing antibody was attached to a solid support as described in Example 12.

Samples were selectively bound to a solid support and FVIII activity measured using the chromogenic assay as described in Example 12, except that 1) six serial 1+1 dilutions of recombinant PEGylated FVIII starting at the dilution of 1:5,000 were prepared.

Figure 15:
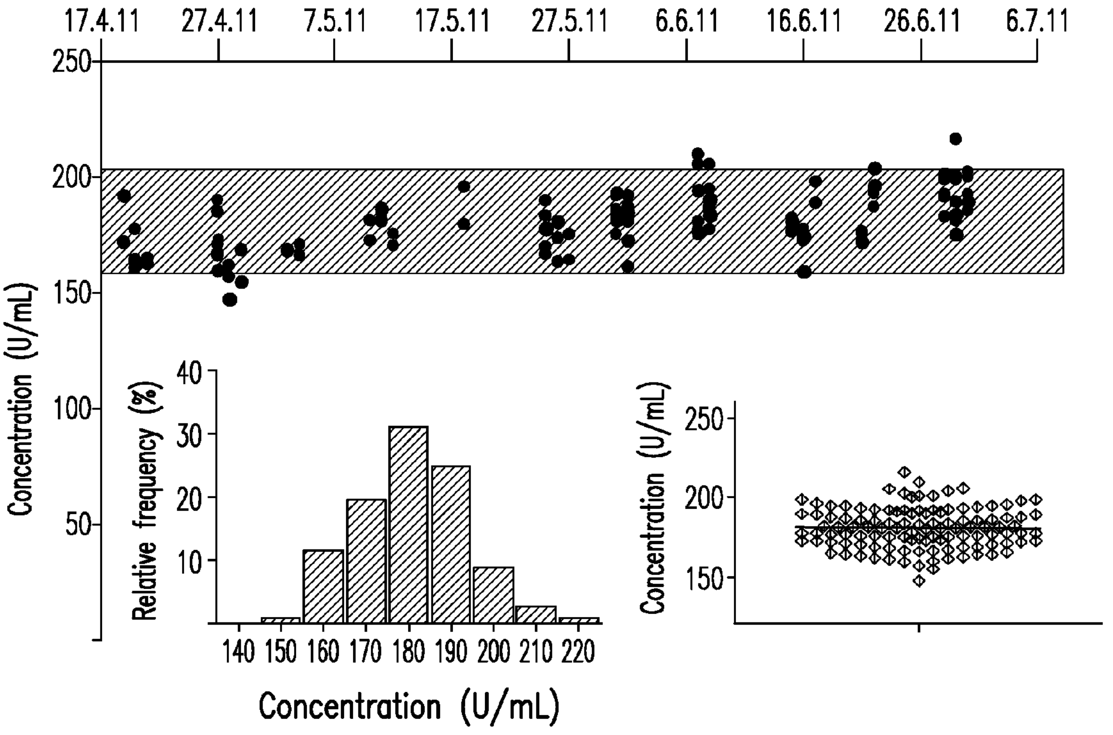
FIG. 15 shows a graph demonstrating the precision of a MDAA for polysialylated recombinant FVIII. The area highlighted gives the 2-SD range of the mean obtained.

The results extrapolated only those mean ODs that were within the range covered by the calibration curve and used at least three dilutions for that purpose. In most of the cases, however, the mean was calculated for five individual dilutions of the dilution series resulting in RSDs clearly lower than 15%. This confirmed that the dilution series of the assay control were parallel to that of the assay calibrator and also met the requirement of measuring several control samples with high, medium and low analyte concentrations. The results represent 39 runs performed by two operators resulting in a total of 113 measurements of polysialylated recombinant FVIII. A mean concentration of 180±11.2 U/mL translated to an RSD of 6.2% describing the inter-run precision of the assay. The mean inter-run precision, determined for two to four measurements per run, was 3.8% with values ranging from 0.3% to 7.4%. FIG. 15 shows these data and also gives the frequency distribution of the data.

The precision of MDAA for polysialylated recombinant FVIII was excellent given that this method combines the principles of a ligand binding assay with that of an activity assay. Thus, relatively high sample dilutions, namely dilution series starting at a dilution of 1/5,000 are required for the selective capture. The following chromogenic activity assay comprises several reagent transfer and incubation steps. Although the obvious complexity of the overall procedure, the RSD, describing the inter-run precision, was low. The mean of 39 runs had an RSD of 6.2%.

Example 15

Accuracy and Precision of MDAA for Polysialylated FVIII in Plasma

This example illustrates accuracy and precision of a MDAA for polysialylated FVIII in plasma using a spike-recovery assay.

A modification-recognizing antibody was attached to a solid support as described in Example 12.

Samples were selectively bound to a solid support and FVIII activity measured using the chromogenic assay as described in Example 12, except that samples comprising plasma from FVIII-deficient mice (E17), from rats, and from cynomolgus monkeys and measured before and after being spiked with polysialylated recombinant FVIII a five concentrations ranging from 0.05 U/mL to 15 U/mL.

Intra-run precision (n=6; determined for the polysialylated recombinant FVIII concentration 0.05, 0.5 and 15 U/mL) and inter-run precision (n=6; determined for 0.05, 0.25, 0.5, 1 and 15 U/mL) were determined for spiked plasma samples, while the assay's accuracy was determined by calculating the recovery of the spiked amounts. Finally, the total error was calculated as sum of inter-run precision and accuracy. The current EMA guideline devises that this total error should not exceed 30% or 40% at the assay's lower limit of quantification (LLOQ). Table 8 summarizes the precision data, expressed as the RSDs of the corresponding means, obtained for the spiked animal plasma and buffer samples.

TABLE 8

Precision of MDAA for polysialylated rFVIII in animal plasma samples

| | Inter-run precision (n = 6) | | | | Intra-run precision (n = 6) | | | |
|---|---|---|---|---|---|---|---|---|
| Nominal (U/mL) | Rat | E17 | Monkey | Buffer | Rat | E17 | Monkey | Buffer |
| 0.05 | 5.4 | 9.7 | 13.8 | 5.7 | 5.7 | 6.1 | 6.0 | 3.2 |
| 0.25 | 4.1 | 7.0 | 4.1 | 4.7 | n.d. | n.d. | n.d. | n.d. |
| 0.5 | 5.3 | 6.7 | 3.8 | 2.7 | 6.3 | 3.5 | 2.8 | 3.0 |
| 1 | 5.5 | 5.4 | 2.8 | 3.6 | n.d. | n.d. | n.d. | n.d. |
| 15 | 3.9 | 4.9 | 2.9 | 4.5 | 3.4 | 1.0 | 3.2 | 2.7 |
| Mean | 4.8 | 6.7 | 5.5 | 4.3 | 5.1 | 3.5 | 4.0 | 3.0 |

n.d. stands for not done.

We found RSDs of less than 10% for all but one sample. This particular monkey plasma sample, for which we determined an RSD of 13.8%, was spiked with 0.05 U/ml, representing the assay's lower limit of quantification. The mean RSDs, describing the inter- and intra-run precision over the range investigated were largely independent of the actual concentration and the respective animal plasma used for spiking. Thus, the precision profile qualified the MDAA for polysialylated recombinant FVIII as a very precise bioanalytical method suitable for the measurement of polysialylated recombinant FVIII in animal plasma samples as required for example to determine pharmacokinetic parameters. Table 9 gives the recoveries determined as a measure of the assay's accuracy and finally the total error, calculated for the individual polysialylated recombinant FVIII concentrations at the lower limit of quantification of 0.05 U/mL and the polysialylated recombinant FVIII concentrations ranging from 0.25 U/mL to 15 U/mL.

TABLE 9

Accuracy and total error of the polysialylated recombinant FVIII MDAA

| Nominal | Accuracy (% Recovery) | | | Nominal | Total error | | |
|---|---|---|---|---|---|---|---|
| (U/mL) | Rat | E17 | Monkey | (U/mL | Rat | E17 | Monkey |
| 0.05 | 98.3 | 98.0 | 99.0 | 0.05 | 7.1 | 11.7 | 14.8 |
| 0.25 | 95.3 | 96.0 | 101.3 | 0.25-15 | 8.9 | 11.0 | 5.8 |
| 0.5 | 95.0 | 97.0 | 100.0 | n.d. | n.d. | n.d. | n.d. |
| 1 | 97.4 | 93.2 | 99.5 | n.d. | n.d. | n.d. | n.d. |
| 15 | 96.2 | 96.6 | 98.0 | n.d. | n.d. | n.d. | n.d. |
| Mean | 96.0 | 95.7 | 99.7 | n.d. | n.d. | n.d. | n.d. |

n.d. stands for not done.

Figure 16:
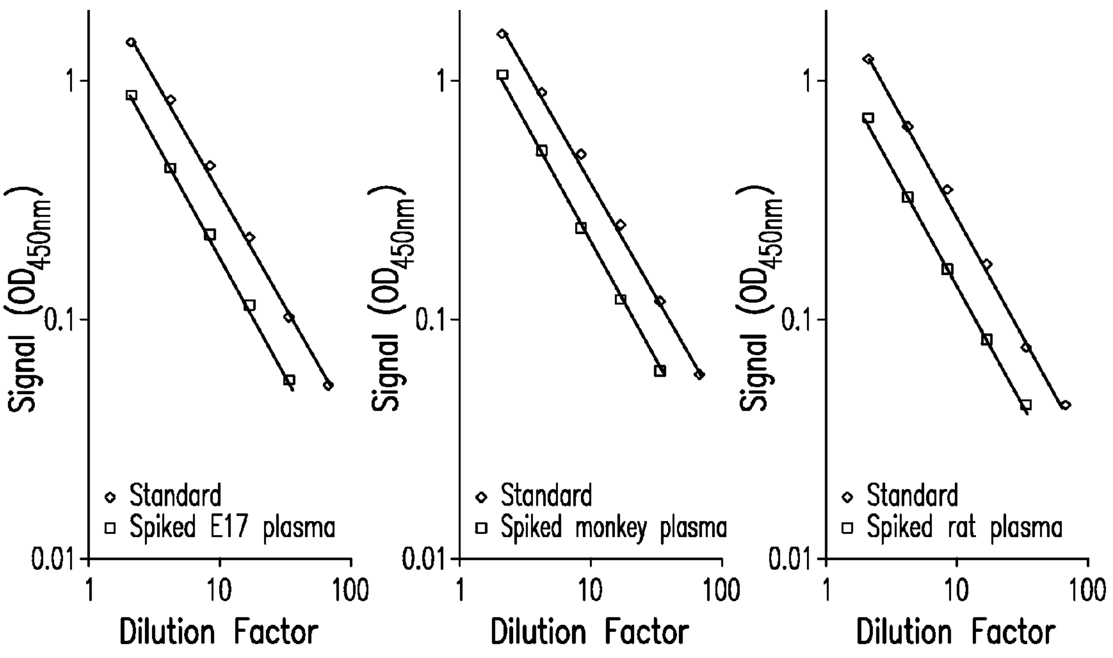
FIG. 16 shows a graph of dose-response curves in animal plasma samples demonstrating the accuracy and precision a MDAA for polysialylated recombinant FVIII.

The recovery of spiked polysialylated recombinant FVIII was excellent in all animal plasma samples tested here, even at the lowest concentration of 0.05 U/mL spiked. Also the total error was not higher than 15% in any of the cases investigated. These data, which easily meet the EMA guideline for bioanalytical assay validation, clearly qualify the MDAA for polysialylated recombinant FVIII to be used for the measurement of polysialylated recombinant FVIII in the plasma of laboratory animals. FIG. 16 finally shows the dose-response curves for all three animal plasma samples, diluted 1/20 and spiked with polysialylated recombinant FVIII (0.068 U/mL). This minimum dilution of 1/20 that also determined the assay's lower limit of quantification was defined as these data demonstrated that there was no substantial influence detectable.

The linearity of the dose response curves obtained in 1/20-diluted animal plasma was as good as that determined for the respective dilution series of the assay standard in buffer only. Moreover, the slopes were very similar and differed by less than 2% for the spiked E17 and rat plasma sample and by less than 9% for the spiked monkey plasma sample.

Example 16

MDAA for PEGylated FIX

This example illustrates a MDAA for PEGylated FIX.

To attach a modification-recognizing antibody to a solid support, 100 μL/well coating antibody solution comprising 4 μg/mL rabbit anti-PEG antibodies (B47-2061-1; Epitomics, Inc., Burlingame, Calif.), 0.1 M $NaHCO_3$—Na2CO3, pH 9.5 was incubated in the wells of a F96 Maxisorp plate at 0±10° C. overnight. The plates were then washed with Washing Buffer comprising PBS and 0.05% Tween 20. The wells of the plate were then blocked by incubation 200 μL/well of Blocking Buffer comprising PBS, 3% skimmed milk, and 50 mM benzamidine at about 18° C. to about 26° C. for 60±10 minutes. The blocked wells were then washed with Washing Buffer.

To selectively bind a sample to a solid support, 100 μL of the following samples were added to a well 1) a dilution series of PEGylated recombinant FIX standard prepared using PBS containing 10 mg/mL HAS and covered a FIX concentration range from 45.5 mU/mL to 0.28 mU/mL 1 or 2) a dilution series of non-modified recombinant FIX prepared using PBS containing 10 mg/mL HSA and covered a FIX concentration range from 350 mU/mL to 25,000 mU/mL. PEGylated recombinant FIX with a degree of PEGylation of about 1 was used. The samples were loaded to the plate and incubated at about 18° C. to about 26° C. for 60±10 minutes. Under these conditions, PEGylated recombinant FIX selectively bound to the solid support by means of its PEG moiety using an anti-PEG antibody. The plate was then washed 6 times with Washing Buffer followed by incubation with 200 μL/well of a FIX dilution buffer comprising 3.4 g/L imidazole, 5.85 g/L NaCl; 10 mg/mL HSA, pH 7.4. This equilibration was done at room temperature for 3 minutes. After a washing step with Washing Buffer, the wells were emptied and FIX activity was measured with a FIX chromogenic assay following the instructions of the manufacturer (HYPHEN Biomed, Vienna, Austria).

Figure 17:
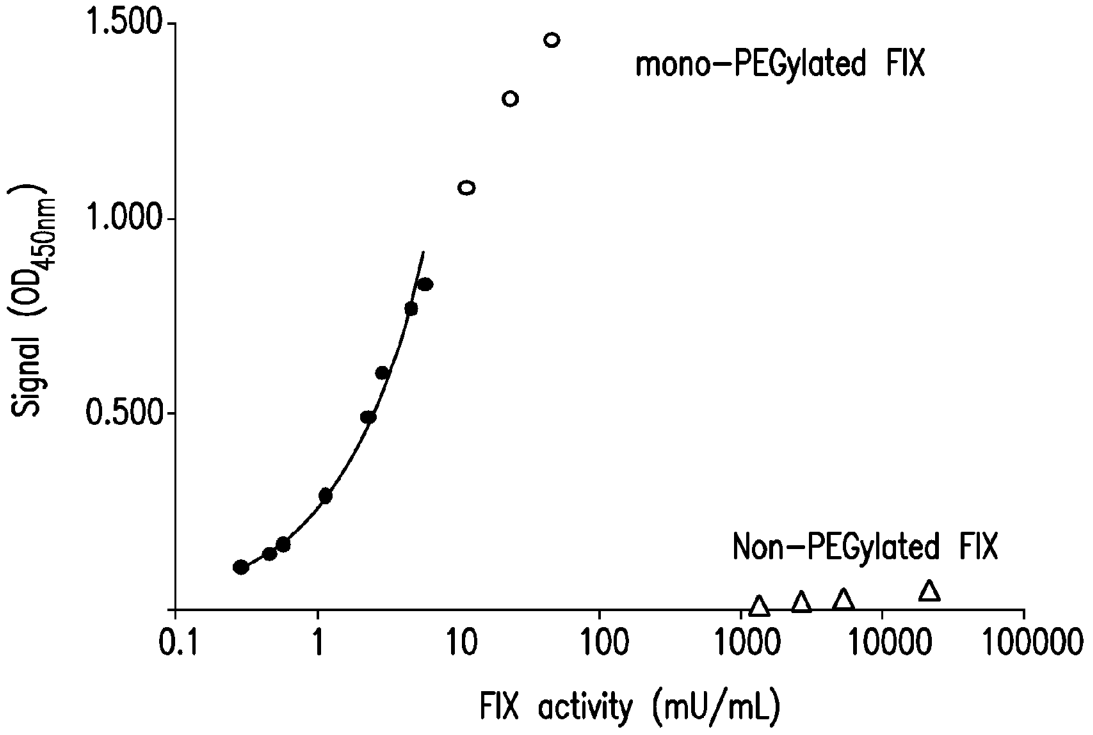
FIG. 17 shows a graph of the concentration-response curves of a MDAA for PEGylated recombinant FIX obtained using PEGylated FIX preparation and a human reference plasma preparation.

FIG. 17 shows the data obtained for the PEGylated FIX and non-modified FIX. PEGylated FIX demonstrated a clear concentration-dependent signal with a linear signal to concentration relation in the range of 5.7 to 0.28 mU FIX/mL. In contrast, non-PEGylated FIX did not show any substantial signal even at 1000-times higher concentrations.

Example 17

Coagulation Assay Format of MDAA for PEGylated FVIII

This example illustrates that a MDAA for PEGylated recombinant FVIII can also be done in the format of a coagulation assay.

To attach a modification-recognizing antibody to a solid support, MaxiSorp Startubes (Nunc) were incubated with 0.5 mL of a coating antibody solution comprising PBS and 20 μg/mL of affinity-purified rabbit anti-PEG antibody (#A151) at 0±10° C. for 18 hours. The tubes were then washed with Washing Buffer comprising PBS and 0.05% Tween 20. The wells of the plate were then blocked by incubation 1 mL of Blocking Buffer comprising PBS, 3% skimmed milk, and 50 mM benzamidine at about 18° C. to about 26° C. for 60±10 minutes. The blocked wells were then washed with Washing Buffer.

To selectively bind a sample to a solid support, 0.5 mL of 1) a dilution series of five samples including a PEGylated recombinant FVIII standard covering a FVIII concentration range from 0.04 mU/mL to 4 mU/mL; and 2) a dilution series of five samples including an Advate recombinant FVIII standard covering a FVIII concentration range from 0.04 mU/mL to 4 mU/mL. The dilution buffer served as a blank. The samples were loaded to the tube and incubated at about 18° C. to about 26° C. for 60±10 minutes. The plate was then washed 6 times with Washing Buffer followed by incubation with 0.5 mL of a FVIII dilution buffer comprising 3.4 g/L imidazole, 5.85 g/L NaCl; 10 mg/mL HSA, pH 7.4. This equilibration was done at about 18° C. to about 26° C. for 5-10 minutes. The tubes were then emptied and a clotting assay was performed by adding 200 μL FVIII dilution buffer and 100 μL FVIII deficiency plasma (#481C00D, Technoclone, GmbH, Vienna, Austria). The mixture was incubated at 37±5° C. for 3 minutes before adding 100 μL 25-mM $CaCl_2$ to start the coagulation. The tubes were kept in a water bath at 37±5° C. and visually checked for clot formation.

Figure 18:
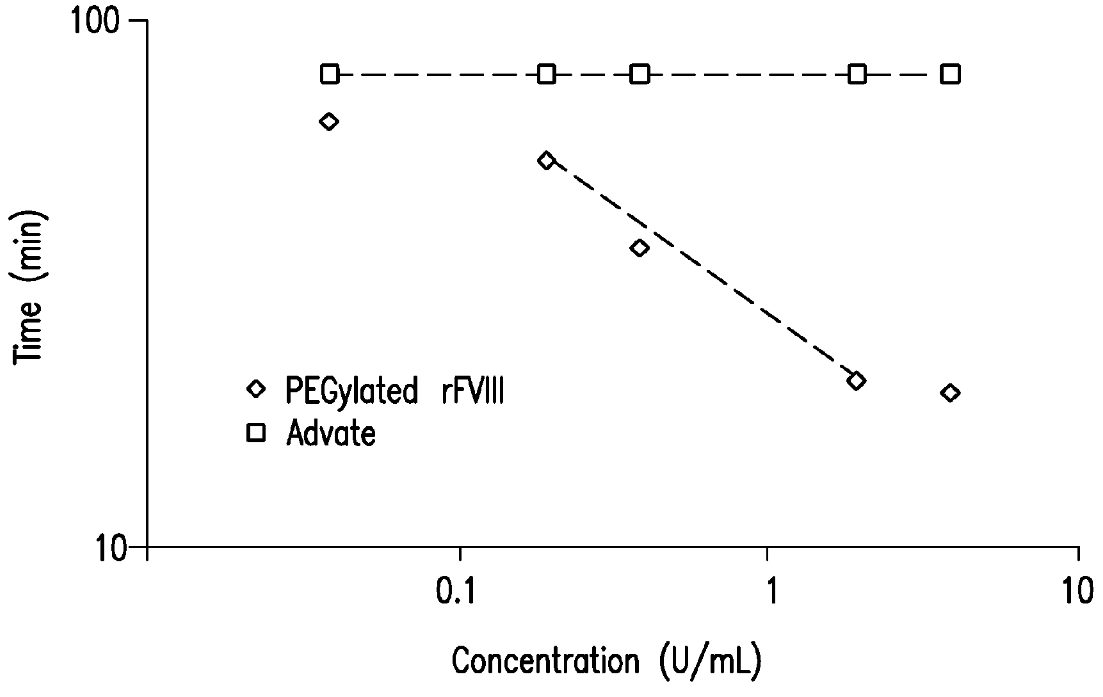
FIG. 18 shows a graph of a MDAA for PEGylated recombinant FVIII using a coagulation assay format.

FIG. 18 shows the results obtained. Clotting occurred only in the tubes that contained PEGylated recombinant FVIII, while the tubes containing Advate recombinant FVIII showed no signs of clot formation within 80 minutes. Moreover, there was a relation between the clotting time and the concentration of PEGylated recombinant FVIII. These data demonstrate that a technique other than chromogenic activity measurement can be used for a MDAA.

Example 18

Coagulation Assay Format of MDAA for Polysialylated FVIII

This example illustrates that a MDAA for polysialylated recombinant FVIII can also be done in the format of a coagulation assay.

To attach a modification-recognizing antibody to a solid support, MaxiSorp Startubes (Nunc) were incubated with 0.5 mL of a coating antibody solution comprising PBS and 20 μg/mL of mouse anti-PSA NCAM antibody (MAB5324) at 0±10° C. for 18 hours. The tubes were then washed with Washing Buffer comprising PBS and 0.05% Tween 20. The wells of the plate were then blocked by incubation 1 mL of Blocking Buffer comprising PBS, 3% skimmed milk, and 50 mM benzamidine at about 18° C. to about 26° C. for 60±10 minutes. The blocked wells were then washed with Washing Buffer.

To selectively bind a sample to a solid support, 0.5 mL of 1) a dilution series of five samples including a polysialylated recombinant FVIII standard covering a FVIII concentration range from 0.04 mU/mL to 4 mU/mL; and 2) a dilution series of five samples including an Advate recombinant FVIII standard covering a FVIII concentration range from 0.04 mU/mL to 4 mU/mL. The dilution buffer served as a blank. The samples were loaded to the tube and incubated at about 18° C.

to about 26° C. for 60±10 minutes. The plate was then washed 6 times with Washing Buffer followed by incubation with 0.5 mL of FVIII dilution buffer comprising 3.4 g/L imidazole, 5.85 g/L NaCl; 10 mg/mL HSA, pH 7.4. This equilibration was done at about 18° C. to about 26° C. for 5-10 minutes. The tubes were then emptied and a clotting assay was performed by adding 200 μL FVIII dilution buffer and 100 μL FVIII deficiency plasma (#481C00D, Technoclone, GmbH, Vienna, Austria). The mixture was incubated at 37±5° C. for 3 minutes before adding 100 μL of 25 mM $CaCl_2$ to start the coagulation. The tubes were kept in a water bath at 37±5° C. and visually checked for clot formation.

Figure 19:
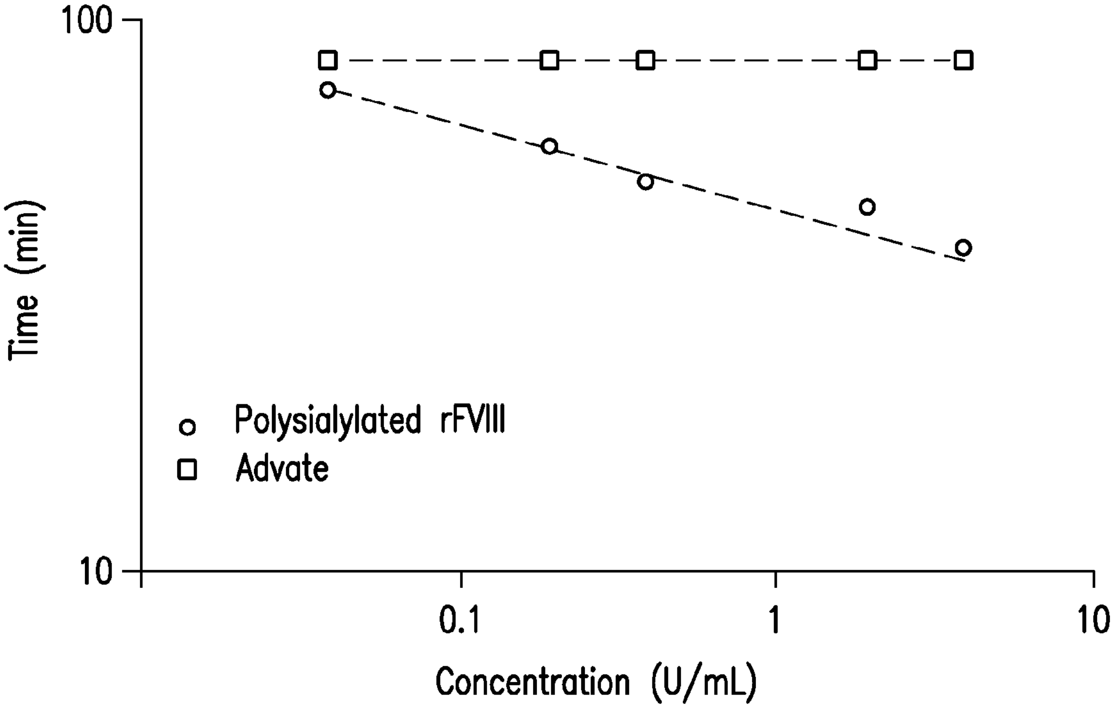
FIG. 19 shows a graph of a MDAA for polysialylated recombinant FVIII using a coagulation assay format.

FIG. 19 shows the results obtained. Clotting occurred only in the tubes that contained polysialylated recombinant FVIII, while the tubes containing Advate showed no signs of clot formation within 80 minutes. Moreover, there was a relation between the clotting time and the concentration of polysialylated rFVIII. These data demonstrate that also a technique other than chromogenic activity measurement can be used for the MDAA.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method for detecting the presence of a recombinant polypeptide comprising a modification, the method comprising the steps of:

incubating a sample including the recombinant polypeptide comprising the modification with a capture agent that selectively binds the modification under conditions allowing the selective binding of the capture agent to the modification, thereby forming a polypeptide-agent complex;

purifying the polypeptide-agent complex from the sample; and assaying for the presence of the recombinant polypeptide and/or a polypeptide activity, wherein detection of the recombinant polypeptide and/or the polypeptide activity is indicative of the presence of the recombinant polypeptide comprising the modification.

2. The method according to claim 1, wherein the sample includes a polypeptide without the modification and/or a polypeptide with a different pattern of degree of modification.

3. The method according to claim 1, wherein the recombinant polypeptide is a therapeutic polypeptide.

4. The method according to claim 1, wherein the recombinant polypeptide is a coagulation factor.

5. The method according to claim 1, wherein the coagulation factor is a Factor II, a Factor IIa, a Factor VII, a Factor VIIa, a Factor VIII, a Factor VIIIa, a Factor IX, a Factor IXa, a Factor X, or a Factor Xa.

6. The method according to claim 1, wherein the capture agent has an association rate constant for a polypeptide comprising the modification of more than $1\times10^5\ M^{-1}\ s^{-1}$.

7. The method according to claim 1, wherein the capture agent has a disassociation rate constant for a polypeptide comprising the modification of less than $1\times10^{-3}\ s^{-1}$.

8. The method according to claim 1, wherein the capture agent has an equilibrium disassociation constant for a polypeptide comprising the modification of less than 0.500 nM.

9. The method according to claim 1, wherein the capture agent has an association rate constant for a polypeptide without a modification or a polypeptide with a different pattern or degree of modification of less than $1\times10^4\ M^{-1}\ s^{-1}$.

10. The method according to claim 1, wherein the capture agent has an association rate constant (Ka) for the recombinant polypeptide comprising a modification that is more than $1\times10^0\ M^{-1}\ s^{-1}$ relative to the association rate constant (Ka) of the capture agent for a recombinant polypeptide without such a modification and/or the association rate constant (Ka) of the capture agent for a recombinant polypeptide with a different pattern or degree of modification.

11. The method according to claim 1, wherein the capture agent has an association rate constant (Ka) for the recombinant polypeptide comprising a modification that is at least 2-fold more then the association rate constant (Ka) of the capture agent for a recombinant polypeptide without such a modification and/or then the association rate constant (Ka) of the capture agent for a recombinant polypeptide with a different pattern or degree of modification.

12. The method according to claim 1, wherein the capture agent has a binding specificity ratio for a recombinant polypeptide comprising a modification relative to a recombinant polypeptide without such a modification and/or relative to a recombinant polypeptide with a different pattern or degree of modification of at least 2:1.

13. The method according to claim 1, wherein the capture agent distinguishes the recombinant polypeptide comprising a modification from the same polypeptide but without the modification.

14. The method according to claim 1, wherein the capture agent distinguishes the recombinant polypeptide comprising a modification from the same polypeptide but with a different pattern or degree of the same modification.

15. The method according to claim 1, wherein the recombinant polypeptide comprising the modification is a PEGylation Factor II, a PEGylation Factor IIa, a polysialylation Factor II, a polysialylation Factor IIa, a HESylation Factor II, a HESylation Factor IIa, a Sylation Factor II, or a Sylation Factor IIa.

16. The method according to claim 1, wherein the recombinant polypeptide comprising the modification is a PEGylation Factor VII, a PEGylation Factor VIIa, a polysialylation Factor VII, a polysialylation Factor VIIa, a HESylation Factor VII, a HESylation Factor VIIa, a Sylation Factor VII, or a Sylation Factor VIIa.

17. The method according to claim 1, wherein the recombinant polypeptide comprising the modification is a PEGylation Factor VIII, a PEGylation Factor Villa, a polysialylation Factor VIII, a polysialylation Factor Villa, a HESylation Factor VIII, a HESylation Factor Villa, a Sylation Factor VIII, or a Sylation Factor VIIIa.

18. The method according to claim 1, wherein the recombinant polypeptide comprising the modification is a PEGylation Factor IX, a PEGylation Factor IXa, a polysialylation Factor IX, a polysialylation Factor IXa, a HESylation Factor IX, a HESylation Factor IXa, a Sylation Factor IX, or a Sylation Factor IXa.

19. The method according to claim 1, wherein the capture agent is an anti-PEG antibody, an anti-PSA antibody, an anti-HES antibody, or an anti-S antibody.

20. The method according to claim 1, wherein the capture agent is attached to a solid support.

21. The method according to claim 20, wherein the solid support is a multi-well plate, a film, a tube, a sheet, a column, or a microparticle.

22. The method according to claim 1, wherein the assaying step is performed using a qualitative assay or a quantitative assay.

23. The method according to claim 1, wherein the assaying step is performed using an in vitro assay, a cell-based assay, or an in vivo assay.

24. The method according to claim 1, wherein the assaying step is performed using a non-specific polypeptide assay or a specific polypeptide assay.

25. The method according to claim 24, wherein the non-specific polypeptide assay is a UV absorption, a biuret assay, or a Bradford assay.

26. The method according to claim 24, wherein the specific polypeptide assay is a chromogenic assay, a colorimetirc assay, a chronometric assay, a chemiluminescense assay, an electrochemiluminescence assay, a bioluminescence assay, a fluorogenic assay, a resonance energy transfer assay, a plane polarization assay, a flow cytometry assay, an immuno-based assay or an activity assay.

27. The method according to claim 24, wherein the activity assay is an enzymatic activity assay, an inhibitory activity assay, a coagulation activity assay, or a polymerization activity assay.

28. The method according to claim 1, wherein selective binding of the capture agent occurs at a neutral to alkaline pH.

* * * * *